US011433118B2

(12) United States Patent
Ferrara

(10) Patent No.: US 11,433,118 B2
(45) Date of Patent: *Sep. 6, 2022

(54) LONG-ACTING VEGF INHIBITORS FOR INTRAOCULAR NEOVASCULARIZATION

(71) Applicant: The Regents of the University of California, Oakland, CA (US)

(72) Inventor: Napoleone Ferrara, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/522,318

(22) Filed: Nov. 9, 2021

(65) Prior Publication Data

US 2022/0088128 A1 Mar. 24, 2022

Related U.S. Application Data

(63) Continuation of application No. PCT/US2020/061519, filed on Nov. 20, 2020.

(60) Provisional application No. 62/939,756, filed on Nov. 25, 2019.

(51) Int. Cl.

| | |
|---|---|
| ***A61K 38/16*** | (2006.01) |
| ***A61K 38/18*** | (2006.01) |
| ***C07K 14/71*** | (2006.01) |
| ***C07K 16/00*** | (2006.01) |
| ***C12N 9/12*** | (2006.01) |
| ***A61K 39/395*** | (2006.01) |
| ***A61K 38/17*** | (2006.01) |
| ***A61P 27/02*** | (2006.01) |

(52) U.S. Cl.

CPC ............ *A61K 38/179* (2013.01); *A61P 27/02* (2018.01)

(58) Field of Classification Search

None

See application file for complete search history.

(56) References Cited

U.S. PATENT DOCUMENTS

| | | | |
|---|---|---|---|
| 5,595,760 | A | 1/1997 | Cherif-Cheikh |
| 5,672,659 | A | 9/1997 | Shalaby et al. |
| 5,712,380 | A | 1/1998 | Kendall et al. |

(Continued)

FOREIGN PATENT DOCUMENTS

| | | | |
|---|---|---|---|
| CN | 1793179 | A | 6/2006 |
| EP | 1183353 | B1 | 4/2005 |

(Continued)

OTHER PUBLICATIONS

Aiello, et al., Suppression of retinal neovascularization in vivo by inhibition of vascular endothelial growth factor (VEGF) using soluble VEGF-receptor chimeric proteins, Proc. Natl. Acad. Sci., USA, vol. 92, pp. 10457-10461, Nov. 1995, Medical Sciences.

(Continued)

*Primary Examiner* — Aurora M Fontainhas

(74) *Attorney, Agent, or Firm* — Eversheds Sutherland (US) LLP

(57) ABSTRACT

Compositions and methods for treating a VEGF-related ophthalmic disorder in a subject in need comprising, administering intravitreally to the subject a therapeutically effective amount of an anti-VEGF agent, comprising a VEGF binding portion operatively linked to a Fc-IgG, wherein the VEGF binding portion comprises at least one VEGF binding domain that is an IgG-like domain 2 of VEGFR-1.

6 Claims, 17 Drawing Sheets

Specification includes a Sequence Listing.

(56) References Cited

U.S. PATENT DOCUMENTS

| | | | |
|---|---|---|---|
| 5,861,484 | A | 1/1999 | Kendall et al. |
| 5,952,199 | A | 9/1999 | Davis-Smyth et al. |
| 5,959,760 | A | 9/1999 | Yamada et al. |
| 6,270,993 | B1 | 8/2001 | Shibuya et al. |
| 6,383,486 | B1 | 5/2002 | Davis-Smyth et al. |
| 6,833,349 | B2 | 12/2004 | Xia et al. |
| 7,070,959 | B1 | 7/2006 | Papadopoulos et al. |
| 7,071,159 | B2 | 7/2006 | Kendall et al. |
| 7,087,411 | B2 | 8/2006 | Daly et al. |
| 7,141,607 | B1 | 11/2006 | Si et al. |
| 7,279,159 | B2 | 10/2007 | Daly et al. |
| 7,303,746 | B2 | 12/2007 | Wiegand et al. |
| 7,303,747 | B2 | 12/2007 | Wiegand et al. |
| 7,303,748 | B2 | 12/2007 | Wiegand et al. |
| 7,306,799 | B2 | 12/2007 | Wiegand et al. |
| 7,354,578 | B2 | 4/2008 | Kandel et al. |
| 7,354,579 | B2 | 4/2008 | Holash et al. |
| 7,354,580 | B2 | 4/2008 | Cedarbaum |
| 7,354,581 | B2 | 4/2008 | Cedarbaum et al. |
| 7,354,582 | B2 | 4/2008 | Yung et al. |
| 7,374,757 | B2 | 5/2008 | Papadopoulos et al. |
| 7,374,758 | B2 | 5/2008 | Papadopoulos et al. |
| 7,396,664 | B2 | 7/2008 | Daly et al. |
| 7,399,612 | B2 | 7/2008 | Daly et al. |
| 7,449,182 | B2 | 11/2008 | Cedarbaum et al. |
| 7,479,272 | B2 | 1/2009 | Cedarbaum |
| 7,479,273 | B2 | 1/2009 | Cedarbaum |
| 7,479,274 | B2 | 1/2009 | Cedarbaum |
| 7,479,275 | B2 | 1/2009 | Cedarbaum |
| 7,482,001 | B2 | 1/2009 | Cedarbaum |
| 7,482,002 | B2 | 1/2009 | Cedarbaum |
| 7,521,049 | B2 | 4/2009 | Wiegand et al. |
| 7,531,172 | B2 | 5/2009 | Stahl et al. |
| 7,531,173 | B2 | 5/2009 | Wiegand et al. |
| 7,582,726 | B2 | 9/2009 | Chen et al. |
| 7,608,261 | B2 | 10/2009 | Furfine et al. |
| 7,635,474 | B2 | 12/2009 | Daly et al. |
| 7,704,500 | B2 | 4/2010 | Papadopoulos et al. |
| 7,807,164 | B2 | 10/2010 | Furfine et al. |
| 7,972,598 | B2 | 7/2011 | Daly et al. |
| 8,034,375 | B2 | 10/2011 | Desai et al. |
| 8,034,772 | B2 | 10/2011 | Kendall et al. |
| 8,048,418 | B2 | 11/2011 | Noguera-Troise et al. |
| 8,084,234 | B2 | 12/2011 | Papadopoulos et al. |
| 8,092,803 | B2 | 1/2012 | Furfine et al. |
| 8,110,546 | B2 | 2/2012 | Dix et al. |
| 8,324,169 | B2 | 12/2012 | Quinn |
| 8,350,010 | B2 | 1/2013 | Chuntharapai et al. |
| 8,404,638 | B2 | 3/2013 | Dix et al. |
| 8,481,046 | B2 | 7/2013 | Furfine et al. |
| 8,647,842 | B2 | 2/2014 | Papadopoulos et al. |
| 8,710,004 | B2 | 4/2014 | Dix et al. |
| 8,735,394 | B2 | 5/2014 | Desai et al. |
| 8,802,107 | B2 | 8/2014 | Furfine et al. |
| 8,921,316 | B2 | 12/2014 | Dix et al. |
| 9,056,102 | B2 | 6/2015 | Quinn |
| 9,139,644 | B2 | 9/2015 | Papadopoulos et al. |
| 9,254,338 | B2 | 2/2016 | Yancopoulos |
| 9,273,113 | B2 | 3/2016 | Davis-Smyth et al. |
| 9,284,369 | B2 | 3/2016 | Ferrara et al. |
| 9,340,594 | B2 | 5/2016 | Furfine et al. |
| 9,416,167 | B2 | 8/2016 | Dix et al. |
| 9,441,029 | B2 | 9/2016 | Stefano et al. |
| 9,511,140 | B2 | 12/2016 | Dix et al. |
| 9,561,288 | B2 | 2/2017 | Desai et al. |
| 9,580,489 | B2 | 2/2017 | Furfine et al. |
| 9,636,400 | B2 | 5/2017 | Dix et al. |
| 9,637,534 | B2 | 5/2017 | Pechan et al. |
| 9,657,084 | B2 | 5/2017 | Ke et al. |
| 9,669,069 | B2 | 6/2017 | Yancopoulos |
| 9,708,386 | B2 | 7/2017 | Papadopoulos et al. |
| 9,777,261 | B2 | 10/2017 | Kim et al. |
| 9,856,462 | B2 | 1/2018 | Kim et al. |
| 9,914,763 | B2 | 3/2018 | Furfine et al. |
| 9,931,330 | B2 | 4/2018 | Zarnitsyn et al. |
| 10,023,627 | B2 | 7/2018 | Kim et al. |
| 10,130,681 | B2 | 11/2018 | Yancopoulos |
| 10,183,983 | B2 | 1/2019 | Pechan et al. |
| 10,206,910 | B2 | 2/2019 | Beeharry et al. |
| 10,308,917 | B2 | 6/2019 | Stefano et al. |
| 10,342,669 | B2 | 7/2019 | Hopkins |
| 10,364,466 | B2 | 7/2019 | Bais et al. |
| 10,392,430 | B2 | 8/2019 | Papadopoulos et al. |
| 10,400,025 | B2 | 9/2019 | Furfine et al. |
| 10,406,226 | B2 | 9/2019 | Dix et al. |
| 2003/0017977 | A1 | 1/2003 | Xia et al. |
| 2007/0010442 | A1 | 1/2007 | Kendall et al. |
| 2008/0292628 | A1 | 11/2008 | Hui |
| 2010/0331250 | A1 | 12/2010 | Zhou et al. |
| 2013/0101557 | A1 | 4/2013 | Yun |
| 2013/0195984 | A1 | 8/2013 | Desai et al. |
| 2015/0175675 | A1 | 6/2015 | Kitajewski et al. |
| 2016/0024483 | A1 | 1/2016 | Kim et al. |
| 2016/0032259 | A1 | 2/2016 | Kim et al. |
| 2017/0232199 | A1 | 8/2017 | Fiedler |
| 2017/0281725 | A1 | 10/2017 | Sims et al. |
| 2017/0305996 | A1 | 10/2017 | Kim et al. |
| 2017/0342127 | A1 | 11/2017 | Pechan et al. |
| 2018/0015181 | A1 | 1/2018 | Desai et al. |
| 2018/0092747 | A1 | 4/2018 | Hopkins |
| 2018/0326126 | A1 | 11/2018 | Fiedler |
| 2018/0339018 | A1 | 11/2018 | Yancopoulos |
| 2019/0046609 | A1 | 2/2019 | Yancopoulos |
| 2019/0117767 | A1 | 4/2019 | Vitti et al. |
| 2019/0194271 | A1 | 6/2019 | Wu et al. |
| 2019/0201385 | A1 | 7/2019 | Beeharry et al. |
| 2019/0240208 | A1 | 8/2019 | Zarnitsyn et al. |
| 2019/0247463 | A1 | 8/2019 | Yancopoulos |
| 2019/0345223 | A1 | 11/2019 | Pechan et al. |
| 2020/0353041 | A1 | 11/2020 | Ferrara |

FOREIGN PATENT DOCUMENTS

| | | | |
|---|---|---|---|
| EP | 1962895 | A2 | 6/2007 |
| EP | 1261317 | B1 | 10/2007 |
| EP | 1544299 | B1 | 12/2008 |
| EP | 2364691 | B1 | 4/2013 |
| EP | 1938799 | B1 | 8/2013 |
| EP | 2663325 | A1 | 11/2013 |
| EP | 2097078 | B1 | 4/2014 |
| EP | 2099489 | B1 | 5/2014 |
| EP | 2916827 | A4 | 5/2014 |
| EP | 1989231 | B1 | 5/2015 |
| EP | 1861116 | B1 | 9/2015 |
| EP | 2944306 | A1 | 11/2015 |
| EP | 3143044 | A1 | 11/2015 |
| EP | 2203479 | B1 | 1/2016 |
| EP | 2481405 | B1 | 3/2016 |
| EP | 3108885 | A1 | 12/2016 |
| EP | 2601214 | B1 | 1/2017 |
| EP | 2586459 | B1 | 5/2017 |
| EP | 3377151 | A1 | 5/2017 |
| EP | 3195874 | A1 | 7/2017 |
| EP | 3222285 | A1 | 9/2017 |
| EP | 3327032 | A1 | 5/2018 |
| EP | 3224278 | A4 | 7/2018 |
| EP | 3412288 | A1 | 12/2018 |
| EP | 3215158 | B1 | 5/2019 |
| EP | 3492495 | A1 | 5/2019 |
| EP | 3194974 | B1 | 10/2019 |
| WO | 2007149334 | A2 | 12/2007 |
| WO | 2012097019 | A1 | 7/2012 |
| WO | 2013082511 | A1 | 6/2013 |
| WO | 2013106765 | A1 | 7/2013 |
| WO | 2015000181 | A1 | 1/2015 |
| WO | WO-2017001990 | A1 | 1/2017 |
| WO | 2018224614 | A1 | 12/2018 |
| WO | 2019004799 | A1 | 1/2019 |
| WO | 2019055902 | A1 | 3/2019 |
| WO | 2019062642 | A1 | 4/2019 |
| WO | 2019099921 | A2 | 5/2019 |
| WO | 2019147944 | A1 | 8/2019 |

(56) References Cited

FOREIGN PATENT DOCUMENTS

| | | | |
|---|---|---|---|
| WO | 2019154776 | A1 | 8/2019 |
| WO | 2021108255 | A1 | 6/2021 |

OTHER PUBLICATIONS

Davis-Smyth, et al., The second immunoglobulin-like domain of the VEGF tyrosine kinase receptor Flt-1 determines ligand binding and may initiate a signal transduction cascade, The EMBO Journal, vol. 15, No. 18, pp. 4919-4927, 1996.
Ferrara, et al., Vascular endothelial growth factor is essential for corpus luteum angiogenesis, Nature Medicine, vol. 4, No. 3, pp. 336-340, Mar. 1998.
Herley, et al., Characterization of the VEGF Binding Site on the Flt-1 Receptor, Biochemical and Biophysical Research Communications, 262, pp. 731-738, 1999.
Holash, et al., VEGF-Trap: A VEGF blocker with potent antitumor effects, PNAS, vol. 99, No. 17, pp. 11393-11398, Aug. 20, 2002.
Lee, et al., Novel Glycosylated VEGF Decoy Receptor Fusion Protein, VEGF-Grab, Efficiently Suppresses Tumor Angiogenesis and Progression, Mol. Cancer Ther., 14(2), pp. 470-479, 2015, Published OnlineFirst Dec. 22, 2014.
Li, et al., A fusion Fragment from Flt-1 and KDR, acted as VEGF decoy receptor and exhibited anti-tumor function, Biotechnol Lett, 32:1609-1613, 2010.
Ma, et al., Identification of the ligand-binding domain of human vascular-endothelial-growth-factor receptor Flt-I, Biotechnol. Appl. Biochem. 34, 199-204, 2001.
Park, et al., The Fourth Immunoglobulin-like Loop in the Extracellular Domain of FLT-1, a VEGF Receptor, Includes a Major Heparin-Binding Site, Biochemical and Biophysical Research Communications, 264, 730-734, 1999.
Pechan, et al., Novel anti-VEGF chimeric molecules delivered by AAV vectors in inhibition of retinal neovascularization, Gene Therapy, 16, 10-16, 2009.
Tan, et al., A small peptide derived from Flt-1 (VEGFR-1) functions as an angiogenic inhibitor, FEBS Letters, 494, 150-156, 2001.
Yu, et al., Soluble Vascular Endothelial Growth Factor Decoy Receptor FP3 Exerts Potent Antiangiogenic Effects, www.moleculartherapy.org, vol. 20, No. 5, 938-947, May 2012.
Olsson et al. "VEGF receptor signalling—In control of vascular function," Nature Reviews Molecular Cell Biology, May 2006, vol. 7, pp. 359-371.
Park et al., "Placenta Growth Factor," The Journal of Biological Chemistry, vol. 269, No. 41, Oct. 14, 1994, pp. 25646-25654.
Park et al., "The Vascular Endothelial Growth Factor (VEGF) Isoforms: Differential Deposition into the Subepithelial Extracellular Matrix and Bioactivity of Extracellular Matrix-bound VEGF," Molecular Biology of the Cell, vol. 4, Dec. 1993, pp. 1317-1326.
International Preliminary Report for WO Application No. PCT/US2019/015160, dated Jul. 28, 2020 (7 pages).
International Search Report and Written Opinion for WO Application No. PCT/US2020-061519, dated Feb. 12, 2021 (9 pages).
Plate et al., "Vascular endothelial growth factor is a potential tumour angiogenesis factor in human gliomas in vivo," Nature, vol. 359, Oct. 29, 1992, pp. 845-848.
Presta et al., "Humanization of an Anti-Vascular Endothelial Growth Factor Monoclonal Antibody for the Therapy of Solid Tumors and Other Disorders," Cancer Research, Oct. 15, 1997, pp. 4593-4599.
Qu-Hong et al., "Ultrastructural Localization of Vascular Permeability Factor/Vascular Endothelial Growth Factor (VPF/VEGF) to the Abluminal Plasma Membrane and Vesiculovacular Organelles of Tumor Microvascular Endothelium," The Journal of Histochemistry and Cytochemistry, vol. 43, No. 4, 1995, pp. 381-389.
Ratanji et al., "Immunogenicity of therapeuric proteins: Influence of aggregation," Journal of Immunotoxicology, vol. 11, No. 2, 2014, pp. 99-109.
Regula et al., "Targeting key angiogenic pathways with a bispecific CrossMAb optimized for neovascular eye diseases," EMBO Molecular Medicine, vol. 8, No. 11, 2016, pp. 1265-1288.
Roberts, Christopher J.,"Therapeutic Protein Aggregation: Mechanisms, Design, and Control." Trends Biotechnol., Jul. 2014, vol. 32 , No. 7, pp. 372-380.
Rodrigues et al., "Functional Characterization of Abicipar-Pegol, an Anti-VEGF DARPin Therpeutic That Potently Inhibits Angiogenesis and Vascular Permeability," IOVS, Dec. 2018, vol. 59, No. 15, pp. 5836-5846.
Ruhrberg et al., "Spatially restricted patterning cues provided by heparin-binding VEGF-A control blood vessel branching morphogenesis," Genes & Development, vol. 16, 2002, pp. 2684-2698.
Saishin et al., "VEGF-TRAP r1r2 Suppresses Choroidal Neovascularization and VEGF-Induced Breakdown of the Blood-Retinal Barrier," Journal of Cellular Physiology, vol. 195, 2003, pp. 241-248.
Sankar et al., Anti-vascular endothelial growth factor (VEGF) drugs for treatment of retinopathy of prematurity (Review), Cochrane Database of Systematic Reviews, 2018, Issue 1, pp. 1-45.
Sarrazin et al., "Heparan Sulfate Proteoglycans," Cold Spring Harb Perspect Biol, 2011, pp. 1-33.
Silva et al., "Tyrosine kinase blocking collagen IV-derived peptide suppresses ocular neovascularization and vascular leakage," Sci Transl Med., Jan. 18, 2017, vol. 9, No. 373, pp. 1-23.
Shibuya et al., "VEGFR and Type-V RTK Activation and Signaling," Cold Spring Harb Perspect Biol., 2013, pp. 1-13.
Smith et al., "Essential Role of Growth Hormone in Ischemia-Induced Retinal Neovascularization," Science, vol. 276, Jun. 13, 1997, pp. 1706-1710.
Smith et al., "Regulation of vascular endothelial growth factor-dependent retinal neovascularization by insulin-like growth factor-1 receptor," Nature Medicine, vol. 5, No. 12, Dec. 1999, pp. 1391-1395.
Terman et al., "Identification of the KDR Tyrosine Kinase as a Receptor for Vascular Endothelial Cell Growth Factor," Biochemical and Biophysical Research Communications, vol. 187, No. 3, 1992, pp. 1579-1586.
Tischer et al., "The Human Gene for Vascular Endothelial Growth Factor," The Journal of Biological Chemistry, vol. 266, No. 18, Jun. 25, 1991, pp. 11947-11954.
Non-Final Office Action for U.S. Appl. No. 16/962,529, dated Jan. 18, 2022 (18 pages).
Non-Final Office Action for U.S. Appl. No. 16/962,529, dated Nov. 5, 2021 (9 pages).
Non-Final Office Action for U.S. Appl. No. 17/526,929, dated Jan. 21, 2022 (9 pages).
Vorum et al., "Real word evidence of use of anti-VEGF therapy in Denmark," Current Medical Research and Opinion, vol. 32, No. 12, 2016, pp. 1943-1950.
Wang et al., "IgG Fc engineering to modulate antibody effector functions," Protein Cell, 2018, vol. 9, No. 1, pp. 63-73.
Wiesmann et al., "Crystal Structure at 1.7 A Resolution of VEGF in Complex with Domain 2 of the Flt-1 Receptor," Cell, vol. 91, Nov. 28, 1997, pp. 695-704.
Woodard et al., "Heparan Sulfate Binding Promotes Accumulation of Intravitreally Delivered Adeno-associated Viral Vectors at the Retina for Enhanced Transduction but Weakly Influences Tropism," Journal of Virology, Nov. 2016, vol. 90, No. 21, pp. 9878-9888.
Xiao et al., "Fully automated, deep learning segmentation of oxygen-induced retinopathy images," JCI Insight, 2017, vol. 2, No. 24, pp. 1-12.
Xin et al., "Evidence for Pro-angiogenic Functions of VEGF-Ax," Cell, vol. 167, 2016, pp. 275-284.
Xin et al., "Heparin-binding VEGFR1 variants as long-acting VEGF inhibitors for treatment of intraocular neovascular disorders," PNAS, 2021, vol. 118, No. 21, pp. 1-9.
Yang et al., "Comparison of Binding Characteristics and In Vivo Activities of Three Inhibitors of Vascular Endothelial Growth Factor A," Mol. Pharmaceutics, 2014, vol. 11, pp. 3421-3430.
Yang et al., "Comparison of biosensor platforms in the evaluation of high affinity antibody-antigen binding kinetics," Analytical Biochemistry, vol. 508, 2016, pp. 78-96.

(56) References Cited

OTHER PUBLICATIONS

Yu et al., "Interaction between Bevacizumab and Murine VEGF-A: A Reassessment," Investigative Opthalmology & Visual Science, Feb. 2008, vol. 49, No. 2, pp. 522-527.
Zheng et al., "Contribution of Vascular Endothelial Growth Factor in the Neovascularization Process during the Pathogenesis of Herpetic Stromal Keratitis," Journal of Virology, Oct. 2001, vol. 75, No. 20, pp. 9828-9835.
Harding et al., "Adeno-Associated Virus Serotype 6 (AAV-6) Vector Mediated Gene Transfer of Soluble VEGF Receptors for the Treatment of Glioblastoma Multiforme," Molecular Therapy, vol. 9, Supp. 1, May 2004, pages S405-S406.
Alitalo et al., "Lymphangiogenesis in development and human disease," Nature, vol. 438, Dec. 2005, pp. 946-953.
Apte et al.,"VEGF Signaling and Disease: Beyond Discovery and Development," Cell, vol. 176, No. 6, Mar. 7, 2019, pp. 1248-1264.
Bachmann et al., "The Role of Antibody Concentration and Avidity in Antiviral Protection," Science, vol. 276, Jun. 27, 1997, pp. 2024-2028.
Barleon et al., "Mapping of the Sites for Ligand Binding and Receptor Dimerization at the Extracellular Domain of the Vascular Endothelial Growth Factor Receptor FLT-1," The Journal of Biological Chemistry, vol. 272, No. 16, Apr. 18, 1997, pp. 10382-10388.
Bogdonovich et al., "Human IgG1 antibodies suppress angiogenesis in a target-independent manner," Signal Transduction and Targeted Therapy, 2016, pp. 1-14.
Brozzo et al., "Thermodynamic and structural description of allosterically regulated VEGFR-2 dimerization," Blood, Feb. 16, 2012, vol. 119, No. 7, pp. 1781-1788.
Campa et al., "Effects of an Anti-VEGF-A Monoclonal Antibody on Laser-Induced Choroidal Neovascularization in Mice: Optimizing Methods to Quantify Vascular Changes," Investigative Opthalmology & Visual Science, Mar. 2008, vol. 49, No. 3, pp. 1178-1183.
Capon et al., "Designing CD4 immunoadhesins for AIDS therapy," Nature, vol. 337, Feb. 9, 1989, pp. 525-531.
Chakrabarti et al., "Studies to Prevent Degradation of Recombinant Fc-Fusion Protein Expressed in Mammalian Cell Line and Protein Characterization," International Journal of Molecular Sciences, 2016, vol. 17, No. 913, pp. 1-22.
Chamow et al., "Immunoadhesins: principles and applications," Tibtech, Feb. 1996, vol. 14, pp. 52-60.
Chen et al., "Erythropoietin deficiency decreases vascular stability in mice," The Journal of Clinical Investigation, vol. 118, No. 2, Feb. 2008, pp. 526-533.
Chen et al., "Selection and Analysis of an Optimized Andi-VEGF Antibody: Crystal Structure of an Affinity-matured Fab in Complex with Antigen," J. Mol. Biol., 1999, vol. 293, pp. 865-881.
Chen et al., "Suppression of Retinal Neovascularization by Erythropoietin siRNA in a Mouse Model of Proliferative Retinopathy," Invest Opthalmol Vis Sci., Mar. 2009, vol. 50, No. 3, pp. 1329-1335.
Christinger et al., "The Crystal Structure of Placental Growth Factor in Complex with Domain 2 of Vascular Endothelial Growth Factor Receptor-1," The Journal of Biological Chemistry, vol. 279, No. 11, Mar. 12, 2004, pp. 10382-10388.
Devries et al., "The fms-Like Tyrosine Kinase, a Receptor for Vascular Endothelial Growth Factor," Science, Feb. 21, 1992, vol. 255, No. 5047, pp. 989-991.
Dvorak et al., "Distribution of Vascular Permeability Factor (Vascular Endothelial Growth Factor) in Tumors: Concentration in Tumor Blood Vessels," J. Exp Med., vol. 174, Nov. 1991, pp. 1275-1278.
Ellison et al., "The nucleotide sequence of a human immunoglobulin C 1 gene," Nucleic Acids Research, vol. 10, No. 13, 1982, pp. 4071-4079.
Extended European Search Report for WO Application No. PCT/US2019/015160, dated Nov. 12, 2021, (10 pages).
Ferrara, Napoleone, "Binding to the Extracellular Matrix and Proteolytic Processing: Two Key Mechanisms Regulating Vascular Endothelial Growth Factor Action," Molecular Biology of the Cell, vol. 21, Mar. 1, 2010, pp. 687-690.
Ferrara et al., "Ten years of anti-vascular endothelial growth factor therapy," Nature Reviews, Drug Discovery, vol. 15, Jun. 2016, pp. 385-403.
Ferrara et al., "The biology of VEGF and its receptors," Nature Medicine, vol. 9, No. 6, Jun. 2003, pp. 669-676.
Ferrara, Napoleone, "VEGF and the quest for tumour angiogenesis factors," Nature Review, Cancer, vol. 2, Oct. 2002, pp. 795-803.
Folkman et al., "Angiogenic Factors," Science, Jan. 23, 1987, vol. 235, No. 4787, pp. 442-447.
Freund et al., "Aflibercept: a review of its use in the treatment of choroidal neovascularization due to age-related macular degeneration," Clinical Opthalmology, 2015, vol. 9, pp. 2355-2371.
Gait, M. J., "Oligonucleotide synthesis: a practical approach," 1984, (9 pages).
Gardiner et al., "Inhibition of Tumor Necrosis Factor-x Improves Physiological Angiogenesis and Reduces Pathological Neovascularization in Ischemic Retinopathy," American Journal of Pathology, vol. 166, No. 2, Feb. 2005, pp. 637-644.
Gerber et al., "Complete Inhibition of Rhabdomyosarcoma Xenograft Growth and Neovascularization Requires Blockade of Both Tumor and Host Vascular Endothelial Growth Factor," Cancer Research, vol. 60, Nov. 15, 2000, pp. 6253-6258.
Gerber et al., "Mice expressing a humanized form of VEGF-A may provide insights into the safety and efficacy of anti-VEGF antibodies," PNAS Feb. 27, 2007, vol. 104, No. 9, pp. 3478-3483.
Gerber et al., "VEGF couples hypertrophic cartilage remodeling, ossification and angiogenesis during endochondral bone formation," Nature Medicine, vol. 5, No. 6, Jun. 1999, pp. 623-628.
Gerber et al., "VEGF is required for growth and survival in neonatal mice," Development, vol. 126, 1999, pp. 1149-1159.
Gerhardt et al., "VEGF guides angiogenic sprouting utilizing endothelial tip cell filopodia," The Journal of Cell Biology, vol. 161, No. 6, Jun. 23, 2003, pp. 1163-1177.
Rakoczy et al., "Gene therapy with recombinant adeno-associated vectors for neovascular age-related macular degeneration: 1 year follow-up of a phase 1 randomised clinical trial," The Lancet, vol. 386, Dec. 12, 2015, pp. 2395-2403.
Holz et al., "Multi-country real-life experience of anti-vascular endothelial growth factor therapy for wet age-related macular degeneration," Br J Opthalmol 2015, vol. 99, pp. 220-226.
Houck et al., "Dual Regulation of Vascular Endothelial Growth Factor Bioavailability by Genetic and Proteolytic Mechanisms," The Journal of Biological Chemistry, vol. 267, No. 36, Dec. 25, 1992, pp. 26031-26037.
Houck et al., "The Vascular Endothelial Growth Factor Family: Identification of a Fourth Molecular Species and Characterization of Alternative Splicing of RNA," Mol Endo., 1991, vol. 5, No. 12, pp. 1806-1814.
Joukov et al., "A novel vascular endothelial growth factor, VEGF-C, is a ligan for the Flt4 (VEGFR-3) and KDR (VEGFR-2) receptor tyrosine kinases," The EMBO Journal, vol. 15, No. 2, 1996, pp. 290-298.
Kim et al., "Potent VEGF blockade causes regression of coopted vessels in a model of neuroblastoma," PNAS, Aug. 20, 2002, vol. 99, No. 17, pp. 11399-11404.
Klagsbrun et al., "Regulators of Angiogenesis," Annu. Rev. Physiol., 1991, vol. 53, pp. 217-239.
Kwak et al., "VEGF Is Major Stimulator in Model of Choroidal Neovascularization," Investigative Opthalmology & Visual Science, Sep. 2000, vol. 41, No. 10, pp. 3157-3164.
Lambert et al. "Laser-induced choroidal neovascularization model to study age-related macular degeneration in mice," Nature Protocols, vol. 8, No. 11, 2013, pp. 2197-2211.
Lange et al., "Intravitreal injection of the heparin analog 5-amino-2-naphthalenesulfonate reduces retinal neovascularization in mice," Experimental Eye Research, vol. 85, 2007, pp. 323-327.

(56) References Cited

OTHER PUBLICATIONS

Lissbrant et al., “Neutralizing VEGF Bioactivity With a Solubel Chimeric VEGF-Receptor Protein flt(I-3)IgG Inhibits Testosterone-Stimulated Prostate Growth in Castrated Mice,” The Prostate, vol. 58, 2004, pp. 57-65.
Maguire et al., “Five-Year Outcomes with Anti-Vascular Endothelial Growth Factor Treatment of Neovascular Age-Related Macular Degeneration,” Opthalmology, vol. 123, No. 8, Aug. 2016, pp. 1751-1761.
Malyala et al., “Endotoxin Limits in Formulations for Preclinical Research,” Journal of Pharmaceutical Sciences, vol. 97, No. 6, Jun. 2008, pp. 2041-2044.
Markovic-Mueller et al., “Structure of the Full-length VEGFR-1 Extracellular Domain in Complex with VEGF-A,” Structure, vol. 25, Feb. 7, 2017, pp. 341-352.
Miller et al., “Vascular Endothelial Growth Factor A in Intraocular Vascular Disease,” Opthalmology, 2013, vol. 120, pp. 106-114.
Morin et al., “Neurodevelopmental Outcomes Following Bevacizumab Injections for Retinopathy of Prematurity,” Pediatrics, vol. 137, No. 4, Apr. 2016, pp. 1-8.
Nguyen et al., “Conbercept (KH-902) for the treatment of neovascular age-related macular degeneration,” Expert Rev. Clin. Pharmocol., vol. 8, No. 5, 2015, pp. 541-548.
Chamow, et al., Therapeutic FC-Fusion Proteins, Willey Blackwell, mAbs, vol. 6, Issue 4, pp. 210-811, Jul./Aug. 2014.
Singapore Patent Application No. SG11202007130R Written Opinion dated Mar. 1, 2022.

*p<0.01; p<0.05

$V_{123}$

Amino acid sequence

MVSYWDTGVLLCALLSCLLLTGSSSGSKLKDPELSLKGTQHIMQAGQTLHLQCRGEAAHKWSLPEMVS
KESERLSITKSACGRNGKQFCSTLTLNTAQANHTGFYSCKYLAVPTSKKKETESAIYIFISDTGR
FPLDTLIPDGKRIIWDSRKGFIISNATYKEIGL
LTCEATVNGHLYKTNYLTHRQTNTIIDVQISTPRPVKLLRGHTLVLNCTATTPLNTRVQMTWSYPDEK
NKRASVRRRIDQSNSHANIFYSVLTIDKMQNKDKGLYTCRVRSGPSFKSVNTSVHIYDKDKTHTCPPC
PAPELLGGPSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRWQQGNVFSCSVMHEALHNH
YTQKSLSLSPGK

Nucleic acid sequence

ATGGTCAGCTACTGGGACACCGGGGTCCTGCTGTGCGCGCTGCTCAGCTGTCTGCTTCTCACAGGATC
TAGTTCAGGTTCAAAATTAAAAGATCCTGAACTGAGTTTAAAAGGCACCCAGCACATCATGCAAGCAG
GCCAGACACTGCATCTCCAATGCAGGGGGGAAGCAGCCCATAAATGGTCTTTGCCTGAAATGGTGAGT
AAGGAAAGCGAAAGGCTGAGCATAACTAAATCTGCCTGTGGAAGAAATGGCAAACAATTCTGCAGTAC
TTTAACCTTGAACACAGCTCAAGCAAACCACACTGGCTTCTACAGCTGCAAATATCTAGCTGTACCTA
CTTCAAAGAAGAAGGAAACAGAATCTGCAATCTATATATTTATTAGTGATACAGGTAGACCTTTCGTA
GAGATGTACAGTGAAATCCCCGAAATTATACACATGACTGAAGGAAGGGAGCTCGTCATTCCCTGCCG
GGTTACGTCACCTAACATCACTGTTACTTTAAAAAAGTTTCCACTTGACACTTTGATCCCTGATGGAA
AACGCATAATCTGGGACAGTAGAAAGGGCTTCATCATATCAAATGCAACGTACAAAGAAATAGGGCTT
CTGACCTGTGAAGCAACAGTCAATGGGCATTTGTATAAGACAAACTATCTCACACATCGACAAACCAA
TACAATCATAGATGTCCAAATAAGCACACCACGCCCAGTCAAATTACTTAGAGGCCATACTCTTGTCC
TCAATTGTACTGCTACCACTCCCTTGAACACGAGAGTTCAAATGACCTGGAGTTACCCTGATGAAAAA
AATAAGAGAGCTTCCGTAAGGCGACGAATTGACCAAAGCAATTCCCATGCCAACATATTCTACAGTGT
TCTTACTATTGACAAAATGCAGAACAAAGACAAAGGACTTTATACTTGTCGTGTAAGGAGTGGACCAT
CATTCAAATCTGTTAACACCTCAGTGCATATATATGATAAAGACAAAACTCACACATGCCCACCGTGC
CCAGCACCTGAACTCCTGGGGGGACCGTCAGTCTTCCTCTTCCCCCCAAAACCCAAGGACACCCTCAT
GATCTCCCGGACCCCTGAGGTCACATGCGTGGTGGTGGACGTGAGCCACGAAGACCCTGAGGTCAAGT
TCAACTGGTACGTGGACGGCGTGGAGGTGCATAATGCCAAGACAAAGCCGCGGGAGGAGCAGTACAAC
AGCACGTACCGTGTGGTCAGCGTCCTCACCGTCCTGCACCAGGACTGGCTGAATGGCAAGGAGTACAA
GTGCAAGGTCTCCAACAAAGCCCTCCCAGCCCCCATCGAGAAAACCATCTCCAAAGCCAAAGGGCAGC
CCCGAGAACCACAGGTGTACACCCTGCCCCCATCCCGGGAGGAGATGACCAAGAACCAGGTCAGCCTG
ACCTGCCTGGTCAAAGGCTTCTATCCCAGCGACATCGCCGTGGAGTGGGAGAGCAATGGGCAGCCGGA
GAACAACTACAAGACCACGCCTCCCGTGCTGGACTCCGACGGCTCCTTCTTCCTCTACAGCAAGCTCA
CCGTGGACAAGAGCAGGTGGCAGCAGGGGAACGTCTTCTCATGCTCCGTGATGCACGAGGCTCTGCAC
AACCACTACACGCAGAAGAGCCTCTCCCTGTCTCCGGGTAAA

Grey with italic: signal peptide; Yellow: Ig-like domain 1; Blue: Ig-like domain 2

Grey: Ig-like domain 3; Black with underline: Human IgG1-Fc fragment

FIGURE 14

$V_{23}$ Amino acid sequence

MVSYWDTGVLLCALLSCLLLTGSSSGIFISDTGRPFVEMYSEIPEIIHMTEGRELVIPCRVTSPNITV
TLKKFPLDTLIPDGKRIIWDSRKGFIISNATYKEIGLLTCEATVNGHLYKTNYLTHRQTNTIIDVQIS
TPRPVKLLRGHTLVLNCTATTPLNTRVQMTWSYPDEKNKRASVRRRIDQSNSHANIFYSVLTIDKMQN
KDKGLYTCRVRSGPSFKSVNTSVHIYDKDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK

Nucleic acid sequence

ATGGTCAGCTACTGGGACACCGGGGTCCTGCTGTGCGCGCTGCTCAGCTGTCTGCTTCTCACAGGATC
TAGTTCAGGTATATTTATTAGTGATACAGGTAGACCTTTCGTAGAGATGTACAGTGAAATCCCCGAAA
TTATACACATGACTGAAGGAAGGGAGCTCGTCATTCCCTGCCGGGTTACGTCACCTAACATCACTGTT
ACTTTAAAAAAGTTTCCACTTGACACTTTGATCCCTGATGGAAAACGCATAATCTGGGACAGTAGAAA
GGGCTTCATCATATCAAATGCAACGTACAAAGAAATAGGGCTTCTGACCTGTGAAGCAACAGTCAATG
GGCATTTGTATAAGACAAACTATCTCACACATCGACAAACCAATACAATCATAGATGTCCAAATAAGC
ACACCACGCCCAGTCAAATTACTTAGAGGCCATACTCTTGTCCTCAATTGTACTGCTACCACTCCCTT
GAACACGAGAGTTCAAATGACCTGGAGTTACCCTGATGAAAAAAATAAGAGAGCTTCCGTAAGGCGAC
GAATTGACCAAAGCAATTCCCATGCCAACATATTCTACAGTGTTCTTACTATTGACAAAATGCAGAAC
AAAGACAAAGGACTTTATACTTGTCGTGTAAGGAGTGGACCATCATTCAAATCTGTTAACACCTCAGT
GCATATATATGATAAAGACAAAACTCACACATGCCCACCGTGCCCAGCACCTGAACTCCTGGGGGGAC
CGTCAGTCTTCCTCTTCCCCCCAAAACCCAAGGACACCCTCATGATCTCCCGGACCCCTGAGGTCACA
TGCGTGGTGGTGGACGTGAGCCACGAAGACCCTGAGGTCAAGTTCAACTGGTACGTGGACGGCGTGGA
GGTGCATAATGCCAAGACAAAGCCGCGGGAGGAGCAGTACAACAGCACGTACCGTGTGGTCAGCGTCC
TCACCGTCCTGCACCAGGACTGGCTGAATGGCAAGGAGTACAAGTGCAAGGTCTCCAACAAAGCCCTC
CCAGCCCCCATCGAGAAAACCATCTCCAAAGCCAAAGGGCAGCCCCGAGAACCACAGGTGTACACCCT
GCCCCCATCCCGGGAGGAGATGACCAAGAACCAGGTCAGCCTGACCTGCCTGGTCAAAGGCTTCTATC
CCAGCGACATCGCCGTGGAGTGGGAGAGCAATGGGCAGCCGGAGAACAACTACAAGACCACGCCTCCC
GTGCTGGACTCCGACGGCTCCTTCTTCCTCTACAGCAAGCTCACCGTGGACAAGAGCAGGTGGCAGCA
GGGGAACGTCTTCTCATGCTCCGTGATGCACGAGGCTCTGCACAACCACTACACGCAGAAGAGCCTCT
CCCTGTCTCCGGGTAAA

Grey with italic: signal peptide; Blue: Ig-like domain 2; Grey: Ig-like domain 3

Black with underline: Human IgG1-Fc fragment

Amino acid sequence

MVSYWDTGVLLCALLSCLLLTGSSSGSKLKDPELSLKGTQHIMQAGQTLHLQCRGEAAHKWSLPEMVS
KESERLSITKSACGRNGKQFCSTLTLNTAQANHTGFYSCKYLAVPTSKKKETESAIYIFISDTGRPFV
EMYSEIPEIIHMTEGRELVIPCRVTSPNITVTLKKFPLDTLIPDGKRIIWDSRKGFIISNATYKEIGL
LTCEATVNGHLYKTNYLTHRQTNTIIDVQISTPRPVKLLRGHTLVLNCTATTPLNTRVQMTWSYPDEK
NKRASVRRRIDQSNSHANIFYSVLTIDKMQNKDKGLYTCRVRSGPSFKSVNTSVHIYDKAVQISTPRP
VKLLRGHTLVLNCTATTPLNTRVQMTWSYPDEKNKRASVRRRIDQSNSHANIFYSVLTIDKMQNKDKG
LYTCRVRSGPSFKSVNTSVHIYDKDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

Nucleic acid sequence

ATGGTCAGCTACTGGGACACCGGGGTCCTGCTGTGCGCGCTGCTCAGCTGTCTGCTTCTCACAGGATC
TAGTTCAGGTTCAAAATTAAAAGATCCTGAACTGAGTTTAAAAGGCACCCAGCACATCATGCAAGCAG
GCCAGACACTGCATCTCCAATGCAGGGGGGAAGCAGCCCATAAATGGTCTTTGCCTGAAATGGTGAGT
AAGGAAAGCGAAAGGCTGAGCATAACTAAATCTGCCTGTGGAAGAAATGGCAAACAATTCTGCAGTAC
TTTAACCTTGAACACAGCTCAAGCAAACCACACTGGCTTCTACAGCTGCAAATATCTAGCTGTACCTA
CTTCAAAGAAGAAGGAAACAGAATCTGCAATCTATATATTTATTAGTGATACAGGTAGACCTTTCGTA
GAGATGTACAGTGAAATCCCCGAAATTATACACATGACTGAAGGAAGGGAGCTCGTCATTCCCTGCCG
GGTTACGTCACCTAACATCACTGTTACTTTAAAAAAGTTTCCACTTGACACTTTGATCCCTGATGGAA
AACGCATAATCTGGGACAGTAGAAAGGGCTTCATCATATCAAATGCAACGTACAAAGAAATAGGGCTT
CTGACCTGTGAAGCAACAGTCAATGGGCATTTGTATAAGACAAACTATCTCACACATCGACAAACCAA
TACAATCATAGATGTCCAAATAAGCACACCACGCCCAGTCAAATTACTTAGAGGCCATACTCTTGTCC
TCAATTGTACTGCTACCACTCCCTTGAACACGAGAGTTCAAATGACCTGGAGTTACCCTGATGAAAAA
AATAAGAGAGCTTCCGTAAGGCGACGAATTGACCAAAGCAATTCCCATGCCAACATATTCTACAGTGT
TCTTACTATTGACAAAATGCAGAACAAAGACAAAGGACTTTATACTTGTCGTGTAAGGAGTGGACCAT
CATTCAAATCTGTTAACACCTCAGTGCATATATATGATAAAGCAGTCCAAATAAGCACACCACGCCCA
GTCAAATTACTTAGAGGCCATACTCTTGTCCTCAATTGTACTGCTACCACTCCCTTGAACACGAGAGT
TCAAATGACCTGGAGTTACCCTGATGAAAAAAATAAGAGAGCTTCCGTAAGGCGACGAATTGACCAAA
GCAATTCCCATGCCAACATATTCTACAGTGTTCTTACTATTGACAAAATGCAGAACAAAGACAAAGGA
CTTTATACTTGTCGTGTAAGGAGTGGACCATCATTCAAATCTGTTAACACCTCAGTGCATATATATGA
TAAAGACAAAACTCACACATGCCCACCGTGCCCAGCACCTGAACTCCTGGGGGGACCGTCAGTCTTCC
TCTTCCCCCCAAAACCCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGTGGAGGTGCATAATGC
CAAGACAAAGCCGCGGGAGGAGCAGTACAACAGCACGTACCGTGTGGTCAGCGTCCTCACCGTCCTGC
ACCAGGACTGGCTGAATGGCAAGGAGTACAAGTGCAAGGTCTCCAACAAAGCCCTCCCAGCCCCCATC
GAGAAAACCATCTCCAAAGCCAAAGGGCAGCCCCGAGAACCACAGGTGTACACCCTGCCCCCATCCCG
GGAGGAGATGACCAAGAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGGAACGTCTT
CTCATGCTCCGTGATGCACGAGGCTCTGCACAACCACTACACGCAGAAGAGCCTCTCCCTGTCTCCGG
GTAAA

Grey with italic: signal peptide; Yellow: Ig-like domain 1; Blue: Ig-like domain 2

Grey: Ig-like domain 3; Black with underline: Human IgG1-Fc fragment

Amino acid sequence

MVSYWDTGVLLCALLSCLLLTGSSSGIFISDTGRPFVEMYSEIPEIIHMTEGRELVIPCRVTSPNITV
TLKKFPLDTLIPDGKRIIWDSRKGFIISNATYKEIGLLTCEATVNGHLYKTNYLTHRQTNTIIDVQIS
TPRPVKLLRGHTLVLNCTATTPLNTRVQMTWSYPDEKNKRASVRRRIDQSNSHANIFYSVLTIDKMQN
KDKGLYTCRVRSGPSFKSVNTSVHIYDKAVQISTPRPVKLLRGHTLVLNCTATTPLNTRVQMTWSYPD
EKNKRASVRRRIDQSNSHANIFYSVLTIDKMQNKDKGLYTCRVRSGPSFKSVNTSVHIYDKDKTHTCP
PCPAPELLGGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFSCSVMHEA
LHNHYTQKSLSLSPGK

Nucleic acid sequence

ATGGTCAGCTACTGGGACACCGGGGTCCTGCTGTGCGCGCTGCTCAGCTGTCTGCTTCTCACAGGATC
TAGTTCAGGTATATTTATTAGTGATACAGGTAGACCTTTCGTAGAGATGTACAGTGAAATCCCCGAAA
TTATACACATGACTGAAGGAAGGGAGCTCGTCATTCCCTGCCGGGTTACGTCACCTAACATCACTGTT
ACTTTAAAAAAGTTTCCACTTGACACTTTGATCCCTGATGGAAAACGCATAATCTGGGACAGTAGAAA
GGGCTTCATCATATCAAATGCAACGTACAAAGAAATAGGGCTTCTGACCTGTGAAGCAACAGTCAATG
GGCATTTGTATAAGACAAACTATCTCACACATCGACAAACCAATACAATCATAGATGTCCAAATAAGC
ACACCACGCCCAGTCAAATTACTTAGAGGCCATACTCTTGTCCTCAATTGTACTGCTACCACTCCCTT
GAACACGAGAGTTCAAATGACCTGGAGTTACCCTGATGAAAAAAATAAGAGAGCTTCCGTAAGGCGAC
GAATTGACCAAAGCAATTCCCATGCCAACATATTCTACAGTGTTCTTACTATTGACAAAATGCAGAAC
AAAGACAAAGGACTTTATACTTGTCGTGTAAGGAGTGGACCATCATTCAAATCTGTTAACACCTCAGT
GCATATATATGATAAAGCAGTCCAAATAAGCACACCACGCCCAGTCAAATTACTTAGAGGCCATACTC
TTGTCCTCAATTGTACTGCTACCACTCCCTTGAACACGAGAGTTCAAATGACCTGGAGTTACCCTGAT
GAAAAAAATAAGAGAGCTTCCGTAAGGCGACGAATTGACCAAAGCAATTCCCATGCCAACATATTCTA
CAGTGTTCTTACTATTGACAAAATGCAGAACAAAGACAAAGGACTTTATACTTGTCGTGTAAGGAGTG
GACCATCATTCAAATCTGTTAACACCTCAGTGCATATATATGATAAAGACAAAACTCACACATGCCCA
CCGTGCCCAGCACCTGAACTCCTGGGGGGACCGTCAGTCTTCCTCTTCCCCCCAAAACCCAAGGACAC
CCTCATGATCTCCCGGACCCCTGAGGTCACATGCGTGGTGGTGGACGTGAGCCACGAAGACCCTGAGG
TCAAGTTCAACTGGTACGTGGACGGCGTGGAGGTGCATAATGCCAAGACAAAGCCGCGGGAGGAGCAG
TACAACAGCACGTACCGTGTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAACCATCTCCAAAGCCAAAG
GGCAGCCCCGAGAACCACAGGTGTACACCCTGCCCCCATCCCGGGAGGAGATGACCAAGAACCAGGTC
AGCCTGACCTGCCTGGTCAAAGGCTTCTATCCCAGCGACATCGCCGTGGAGTGGGAGAGCAATGGGCA
GCCGGAGAACAACTACAAGACCACGCCTCCCGTGCTGGACTCCGACGGCTCCTTCTTCCTCTACAGCA
AGCTCACCGTGGACAAGAGCAGGTGGCAGCAGGGGAACGTCTTCTCATGCTCCGTGATGCACGAGGCT
CTGCACAACCACTACACGCAGAAGAGCCTCTCCCTGTCTCCGGGTAAA

Grey with italic: signal peptide; Blue: Ig-like domain 2; Grey: Ig-like domain 3

Black with underline: Human IgG1-Fc fragment

FIGURE 17

$V_{1234}$ Amino acid sequence

MVSYWDTGVLLCALLSCLLLTGSSSGSKLKDPELSLKGTQHIMQAGQTLHLQCRGEAAHKWSLPEMVS
KESERLSITKSACGRNGKQFCSTLTLNTAQANHTGFYSCKYLAVPTSKKKETESAIYIFISDTGRPFV
EMYSEIPEIIHMTEGRELVIPCRVTSPNITVTLKKFPLDTLIPDGKRIIWDSRKGFIISNATYKEIGL
LTCEATVNGHLYKTNYLTHRQTNTIIDVQISTPRPVKLLRGHTLVLNCTATTPLNTRVQMTWSYPDEK
NKRASVRRRIDQSNSHANIFYSVLTIDKMQNKDKGLYTCRVRSGPSFKSVNTSVHIYDKAFITVKHRK
QQVLETVAGKRSYRLSMKVKAFPSPEVVWLKDGLPATEKSARYLTRGYSLIIKDVTEEDAGNYTILLS
IKQSNVFKNLTATLIVNVKPDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK

Nucleic acid sequence

ATGGTCAGCTACTGGGACACCGGGGTCCTGCTGTGCGCGCTGCTCAGCTGTCTGCTTCTCACAGGATC
TAGTTCAGGTTCAAAATTAAAAGATCCTGAACTGAGTTTAAAAGGCACCCAGCACATCATGCAAGCAG
GCCAGACACTGCATCTCCAATGCAGGGGGGAAGCAGCCCATAAATGGTCTTTGCCTGAAATGGTGAGT
AAGGAAAGCGAAAGGCTGAGCATAACTAAATCTGCCTGTGGAAGAAATGGCAAACAATTCTGCAGTAC
TTTAACCTTGAACACAGCTCAAGCAAACCACACTGGCTTCTACAGCTGCAAATATCTAGCTGTACCTA
CTTCAAAGAAGAAGGAAACAGAATCTGCAATCTATATATTTATTAGTGATACAGGTAGACCTTTCGTA
GAGATGTACAGTGAAATCCCCGAAATTATACACATGACTGAAGGAAGGGAGCTCGTCATTCCCTGCCG
GGTTACGTCACCTAACATCACTGTTACTTTAAAAAAGTTTCCACTTGACACTTTGATCCCTGATGGAA
AACGCATAATCTGGGACAGTAGAAAGGGCTTCATCATATCAAATGCAACGTACAAAGAAATAGGGCTT
CTGACCTGTGAAGCAACAGTCAATGGGCATTTGTATAAGACAAACTATCTCACACATCGACAAACCAA
TACAATCATAGATGTCCAAATAAGCACACCACGCCCAGTCAAATTACTTAGAGGCCATACTCTTGTCC
TCAATTGTACTGCTACCACTCCCTTGAACACGAGAGTTCAAATGACCTGGAGTTACCCTGATGAAAAA
AATAAGAGAGCTTCCGTAAGGCGACGAATTGACCAAAGCAATTCCCATGCCAACATATTCTACAGTGT
TCTTACTATTGACAAAATGCAGAACAAAGACAAAGGACTTTATACTTGTCGTGTAAGGAGTGGACCAT
CATTCAAATCTGTTAACACCTCAGTGCATATATATGATAAAGCATTCATCACTGTGAAACATCGAAAA
CAGCAGGTGCTTGAAACCGTAGCTGGCAAGCGGTCTTACCGGCTCTCTATGAAAGTGAAGGCATTTCC
CTCGCCGGAAGTTGTATGGTTAAAAGATGGGTTACCTGCGACTGAGAAATCTGCTCGCTATTTGACTC
GTGGCTACTCGTTAATTATCAAGGACGTAACTGAAGAGGATGCAGGGAATTATACAATCTTGCTGAG
CATAAAACAGTCAAATGTGTTTAAAAACCTCACTGCCACTCTAATTGTCAATGTGAAACCCGACAAAAC
TCACACATGCCCACCGTGCCCAGCACCTGAACTCCTGGGGGGACCGTCAGTCTTCCTCTTCCCCCCAA
AACCCAAGGACACCCTCATGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCATAATGCCAAGACAAAGCC
GCGGGAGGAGCAGTACAACAGCACGTACCGTGTGGTCAGCGTCCTCACCGTCCTGCACCAGGACTGGC
TGAATGGCAAGGAGTACAAGTGCAAGGTCTCCAACAAAGCCCTCCCAGCCCCCATCGAGAAAACCATC
TCCAAAGCCAAAGGGCAGCCCCGAGAACCACAGGTGTACACCCTGCCCCCATCCCGGGAGGAGATGAC
CAAGAACCAGGTCAGCCTGACCTGCCTGGTCAAAGGCTTCTATCCCAGCGACATCGCCGTGGAGTGGG
AGAGCAATGGGCAGCCGGAGAACAACTACAAGACCACGCCTCCCGTGCTGGACTCCGACGGCTCCTTC
TTCCTCTACAGCAAGCTCACCGTGGACAAGAGCAGGTGGCAGCAGGGGAACGTCTTCTCATGCTCCGT
GATGCACGAGGCTCTGCACAACCACTACACGCAGAAGAGCCTCTCCCTGTCTCCGGGTAAA

Grey with italic: signal peptide, Yellow: Ig-like domain 1, Blue: Ig-like domain 2

Grey: Ig-like domain 3; Green: Ig-like domain 4, Black with underline: Human IgG1-Fc fragment

Amino acid sequence

MVSYWDTGVLLCALLSCLLLTGSSSGIFISDTGRPFVEMYSEIPEIIHMTEGRELVIPCRVTSPNITV
TLKKFPLDTLIPDGKRIIWDSRKGFIISNATYKEIGLLTCEATVNGHLYKTNYLTHRQTNTIIDVQIS
TPRPVKLLRGHTLVLNCTATTPLNTRVQMTWSYPDEKNKRASVRRRIDQSNSHANIFYSVLTIDKMQN
KDKGLYTCRVRSGPSFKSVNTSVHIYDKAFITVKHRKQQVLETVAGKRSYRLSMKVKAFPSPEVVWLK
DGLPATEKSARYLTRGYSLIIKDVTEEDAGNYTILLSIKQSNVFKNLTATLIVNVKP<u>DKTHTCPPCPA</u>
<u>PELLGGPSVFLFPPKPKDTLMISRTPEVTCVVVDVSHEDPEVKFNWYVDGVEVHNAKTKPREEQYNST</u>
<u>YRVVSVLTVLHQDWLNGKEYKCKVSNKALPAPIEKTISKAKGQPREPQVYTLPPSRDELTKNQVSLTC</u>
<u>LVKGFYPSDIAVEWESNGQPENNYKTTPPVLDSDGSFFLYSKLTVDKSRWQQGNVFSCSVMHEALHNH</u>
<u>YTQKSLSLSPGK</u>

Nucleic acid sequence

ATGGTCAGCTACTGGGACACCGGGGTCCTGCTGTGCGCGCTGCTCAGCTGTCTGCTTCTCACAGGATC
TAGTTCAGGTATATTTATTAGTGATACAGGTAGACCTTTCGTAGAGATGTACAGTGAAATCCCCGAAA
TTATACACATGACTGAAGGAAGGGAGCTCGTCATTCCCTGCCGGGTTACGTCACCTAACATCACTGTT
ACTTTAAAAAAGTTTCCACTTGACACTTTGATCCCTGATGGAAAACGCATAATCTGGGACAGTAGAAA
GGGCTTCATCATATCAAATGCAACGTACAAAGAAATAGGGCTTCTGACCTGTGAAGCAACAGTCAATG
GGCATTTGTATAAGACAAACTATCTCACACATCGACAAACCAATACAATCATAGATGTCCAAATAAGC
ACACCACGCCCAGTCAAATTACTTAGAGGCCATACTCTTGTCCTCAATTGTACTGCTACCACTCCCTT
GAACACGAGAGTTCAAATGACCTGGAGTTACCCTGATGAAAAAAATAAGAGAGCTTCCGTAAGGCGAC
GAATTGACCAAAGCAATTCCCATGCCAACATATTCTACAGTGTTCTTACTATTGACAAAATGCAGAAC
AAAGACAAAGGACTTTATACTTGTCGTGTAAGGAGTGGACCATCATTCAAATCTGTTAACACCTCAGT
GCATATATATGATAAAGCATTCATCACTGTGAAACATCGAAAACAGCAGGTGCTTGAAACCGTAGCTG
GCAAGCGGTCTTACCGGCTCTCTATGAAAGTGAAGGCATTTCCCTCGCCGGAAGTTGTATGGTTAAAA
GATGGGTTACCTGCGACTGAGAAATCTGCTCGCTATTTGACTCGTGGCTACTCGTTAATTATCAAGGA
CGTAACTGAAGAGGATGCAGGGAATTATACAATCTTGCTGAGCATAAAACAGTCAAATGTGTTTAAAA
ACCTCACTGCCACTCTAATTGTCAATGTGAAACCC<u>GACAAAACTCACACATGCCCACCGTGCCCAGCA</u>
<u>CCTGAACTCCTGGGGGGACCGTCAGTCTTCCTCTTCCCCCCAAAACCCAAGGACACCCTCATGATCTC</u>
<u>CCGGACCCCTGAGGTCACATGCGTGGTGGTGGACGTGAGCCACGAAGACCCTGAGGTCAAGTTCAACT</u>
<u>GGTACGTGGACGGCGTGGAGGTGCATAATGCCAAGACAAAGCCGCGGGAGGAGCAGTACAACAGCACG</u>
<u>TACCGTGTGGTCAGCGTCCTCACCGTCCTGCACCAGGACTGGCTGAATGGCAAGGAGTACAAGTGCAA</u>
<u>GGTCTCCAACAAAGCCCTCCCAGCCCCCATCGAGAAAACCATCTCCAAAGCCAAAGGGCAGCCCCGAG</u>
<u>AACCACAGGTGTACACCCTGCCCCCATCCCGGGAGGAGATGACCAAGAACCAGGTCAGCCTGACCTGC</u>
<u>CTGGTCAAAGGCTTCTATCCCAGCGACATCGCCGTGGAGTGGGAGAGCAATGGGCAGCCGGAGAACAA</u>
<u>CTACAAGACCACGCCTCCCGTGCTGGACTCCGACGGCTCCTTCTTCCTCTACAGCAAGCTCACCGTGG</u>
<u>ACAAGAGCAGGTGGCAGCAGGGGAACGTCTTCTCATGCTCCGTGATGCACGAGGCTCTGCACAACCAC</u>
<u>TACACGCAGAAGAGCCTCTCCCTGTCTCCGGGTAAA</u>

*Grey with italic*: signal peptide; Blue: Ig-like domain 2; Grey: Ig-like domain 3; Green: Ig-like domain 4;

<u>Black with underline</u>: Human IgG1-Fc fragment

Amino acid sequence

MVSYWDTGVLLCALLSCLLLTGSSSGIFISDTGRPFVEMYSEIPEIIHMTEGRELVIPCRVTSPNITV
TLKKFPLDTLIPDGKRIIWDSRKGFIISNATYKEIGLLTCEATVNGHLYKTNYLTHRQTNTIIDVFIT
VKHRKQQVLETVAGKRSYRLSMKVKAFPSPEVVWLKDGLPATEKSARYLTRGYSLIIKDVTEEDAGNY
TILLSIKQSNVFKNLTATLIVNVKPDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

Nucleic acid sequence

ATGGTCAGCTACTGGGACACCGGGGTCCTGCTGTGCGCGCTGCTCAGCTGTCTGCTTCTCACAGGATC
TAGTTCAGGTATATTTATTAGTGATACAGGTAGACCTTTCGTAGAGATGTACAGTGAAATCCCCGAAA
TTATACACATGACTGAAGGAAGGGAGCTCGTCATTCCCTGCCGGGTTACGTCACCTAACATCACTGTT
ACTTTAAAAAAGTTTCCACTTGACACTTTGATCCCTGATGGAAAACGCATAATCTGGGACAGTAGAAA
GGGCTTCATCATATCAAATGCAACGTACAAAGAAATAGGGCTTCTGACCTGTGAAGCAACAGTCAATG
GGCATTTGTATAAGACAAACTATCTCACACATCGACAAACCAATACAATCATAGATGTCTTCATCACT
GTGAAACATCGAAAACAGCAGGTGCTTGAAACCGTAGCTGGCAAGCGGTCTTACCGGCTCTCTATGAA
AGTGAAGGCATTTCCCTCGCCGGAAGTTGTATGGTTAAAAGATGGGTTACCTGCGACTGAGAAATCTG
CTCGCTATTTGACTCGTGGCTACTCGTTAATTATCAAGGACGTAACTGAAGAGGATGCAGGGAATTAT
ACAATCTTGCTGAGCATAAAACAGTCAAATGTGTTTAAAAACCTCACTGCCACTCTAATTGTCAATGT
GAAACCCGACAAAACTCACACATGCCCACCGTGCCCAGCACCTGAACTCCTGGGGGGACCGTCAGTCT
TCCTCTTCCCCCCAAAACCCAAGGACACCCTCATGATCTCCCGGACCCCTGAGGTCACATGCGTGGTG
GTGGACGTGAGCCACGAAGACCCTGAGGTCAAGTTCAACTGGTACGTGGACGGCGTGGAGGTGCATAA
TGCCAAGACAAAGCCGCGGGAGGAGCAGTACAACAGCACGTACCGTGTGGTCAGCGTCCTCACCGTCC
TGCACCAGGACTGGCTGAATGGCAAGGAGTACAAGTGCAAGGTCTCCAACAAAGCCCTCCCAGCCCCC
ATCGAGAAAACCATCTCCAAAGCCAAAGGGCAGCCCCGAGAACCACAGGTGTACACCCTGCCCCCATC
CCGGGAGGAGATGACCAAGAACCAGGTCAGCCTGACCTGCCTGGTCAAAGGCTTCTATCCCAGCGACA
TCGCCGTGGAGTGGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAGCAGGGGAACGT
CTTCTCATGCTCCGTGATGCACGAGGCTCTGCACAACCACTACACGCAGAAGAGCCTCTCCCTGTCTC
CGGGTAAA

Grey with italic: signal peptide; Blue: Ig-like domain 2; Green: Ig-like domain 4

Black with underline: Human IgG1-Fc fragment

FIGURE 20

LONG-ACTING VEGF INHIBITORS FOR INTRAOCULAR NEOVASCULARIZATION

CROSS REFERENCE TO RELATED APPLICATIONS

This application is a continuation of PCT Application No. PCT/US2020/061519, filed Nov. 20, 2020, which claims the benefit of U.S. Provisional Patent Application No. 62/939,756, filed on Nov. 25, 2019. The entire contents of which are incorporated by reference herewith.

GOVERNMENT SUPPORT

The invention was made with government support under Grant No. EY031345 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 19, 2020, is named 24978-0595_SL.txt and is 54,480 bytes in size.

TECHNICAL FIELD

The present invention relates to novel long-acting VEGF inhibitors for intraocular neovascularization.

BACKGROUND

The development of a neovascular supply or angiogenesis serves crucial homeostatic roles since the blood vessels carry nutrients to tissues and organs and remove catabolic products[1]. However, uncontrolled growth of blood vessels can promote or facilitate numerous disease processes, including tumors and intraocular vascular disorders[1]. Although numerous angiogenic factors were initially identified and characterized[2], work performed in many laboratories has established VEGF as a key regulator of normal and pathological angiogenesis as well as vascular permeability[3 4]. Alternative exon splicing results in the generation of multiple isoforms that differ in their affinity for heparin, including $VEGF_{121}$, $VEGF_{165}$ and $VEGF_{189}$. $VEGF_{121}$ lacks significant heparin binding. While $VEGF_{165}$ has a single, exon-7 encoded, heparin-binding domain, $VEGF_{189}$ has two heparin-binding domains encoded by exon 6- and exon 7[5 6]. Much experimental evidence documents the key role of the heparin-binding VEGF isoforms in the establishment of biochemical gradients required for angiogenesis[7-9]. VEGF is a member of a gene family that also includes P1GF, VEGF-B, VEGF-C and VEGF-D. Three related receptor tyrosine kinase (RTKs) have been reported to bind VEGF ligands: VEGFR1[10], VEGFR2[11] and VEGFR3[12]. VEGF binds both VEGFR1 and VEGFR2, while P1GF and VEGF-B interact selectively with VEGFR1. VEGFR3 binds VEGF-C and VEGF-D, which are implicated in lymphangiogenesis[13 14] Each member of this RTK class has seven immunoglobulin (Ig)-like domains in the extracellular portion[15]. There is agreement that VEGFR-2 is the main signaling receptor for VEGF[14], although VEGFR1 binds VEGF with substantially higher affinity than VEGFR2[15].

VEGF inhibitors have become a standard of therapy in multiple tumors and have transformed the treatment of intraocular neovascular disorders such as the neovascular form of age-related macular degeneration (AMD), proliferative diabetic retinopathy and retinal vein occlusion, which are leading causes of severe vision loss and legal blindness[16 3 17]. Currently, three anti-VEGF drugs are widely used in the USA for ophthalmological indications: bevacizumab, ranibizumab and aflibercept[3]. Bevacizumab is a full-length IgG antibody targeting VEGF[18]. Even though bevacizumab was not developed for ophthalmological indications, it is widely used off-label due to its low cost. Ranibizumab is an affinity-matured anti-VEGF Fab[19]. Aflibercept is an IgG-Fc fusion protein[20], with elements from VEGFR1 and VEGFR2, that binds VEGF, PIGF and VEGF-B[21]. Importantly, after five-year treatment with ranibizumab or bevacizumab, about half of neovascular AMD patients had good vision, i.e. visual acuity 20/40 or better, an outcome that would have not been possible before anti-VEGF agents were available[22]. However, in real-life clinical settings, many patients receive fewer anti-VEGF injections than in clinical trials and it has been hypothesized that this correlates with less satisfactory visual outcomes[23]. Therefore, there is a need to develop agents with longer duration after intraocular injection, thus reducing the frequency of injections and a number of approaches to this end have been attempted[24 25]. Aflibercept (EYLEA) was approved based on clinical trials showing that every 8-week administration of the dose of 2 mg could match the efficacy of monthly ranibizumab (0.5 mg). However, despite the prediction that a switch to aflibercept would reduce the number of intravitreal injections, recent studies suggest that it is not the case[26]. Therefore, there is still an unmet medical need for intravitreal anti-VEGF agents with improved half-life.

In 1996, in the course of structure-function studies aiming to identify VEGF binding elements in VEGFR1, we found that deletion of Ig-like domain (D) 2, but not of other Ds, abolished VEGF or PIGF binding 27. Replacing D2 of VEGFR3 with VEGFR1 D2 conferred on VEGFR3 the ligand specificity of VEGFR127. Subsequent studies documented the interaction between D2 and VEGF (or P1GF) by X-ray crystallography[28-30]. However, D3 was important for optimal VEGF binding[27 28]. These initial studies led to the design of a construct comprising the first three lg-like Ds of VEGFR1, fused to an Fc-lgG (Flt-1-3-IgG)[27]. Flt-1-3-lgG showed a potent ability to neutralize VEGF in vitro and in several in vivo models of physiological and pathological angiogenesis[31-34 35 36]. However, the half-life of this molecule following systemic administration was relatively short due to the presence of clusters of basic residues in D3, which resulted in binding to heparan sulfate proteoglycans (HSPG) and sequestration in various tissues.

In 2002 Holash et al[21] described an IgG fusion construct comprising of VEGFR1 D2 and VEGFR2 D3, which has much lower heparin-affinity than VEGFR1 D3. This molecule, known today as aflibercept, ziv-aflibercept or EYLEA, was reported to have a significantly longer systemic half-life than Flt-(1-3-lgG)[21]. These PK characteristics, combined with high binding affinity for VEGF and the ability to bind P1GF and VEGF-B, led to the prediction that aflibercept would be a more effective anti-tumor agent than other VEGF inhibitors[21 37]. However, aflibercept has gained FDA approval only for 2nd line treatment of colorectal cancer, while bevacizumab and the anti-VEGFR2 antibody ramucirumab received several FDA approvals in multiple cancer types[3 17], suggesting that the above mentioned characteristics did not provide a therapeutic advantage. Clearly, aflibercept has had its major clinical impact as an intravitreal treatment for ocular vascular disorders.

SUMMARY OF THE INVENTION

The present invention provides compositions and methods for inhibiting angiogenesis and for treating VEGF-associated conditions, such as ocular disease, including but not limited to, age-related macular degeneration, proliferative diabetic retinopathy, retinal vein occlusion, choroidal neovascularization secondary to myopia, retinopathy of prematurity, diabetic macular edema, polypoidal choroidal vasculopathy, comprising administering an anti-VEGF agent that inhibits the activity of VEGF and, at the same time, has strong heparin-binding characteristics, thereby providing superior pharmacokinetics, namely having a longer half-life of the therapeutic agent following intravitreal administration.

In embodiments, the present invention provides compositions and methods for treating a VEGF-related ophthalmic disorder in a subject in need comprising, administering intravitreally to the subject a first therapeutically effective amount of an anti-VEGF agent, and administering intravitreally to the subject a second therapeutically effective amount of the anti-VEGF agent within 10 to 30 weeks of the earlier administration. In embodiments, the anti-VEGF agent comprises a VEGF binding portion operatively linked to a Fc-IgG, wherein the VEGF binding portion comprises at least one VEGF binding domain that is an IgG-like domain 2 of VEGFR-1.

In embodiments, the second therapeutically effective amount of the anti-VEGF agent is administered intravitreally within 16 to 24 weeks of the earlier administration. In embodiments, the method comprises subsequent administrations of the therapeutically effective amount of the anti-VEGF agent administered intravitreally within 10 to 30 weeks of a prior administration for a period of at least one year.

In embodiments, the therapeutically effective amount of the anti-VEGF agent is about 1 to 10 mg. In embodiments, the therapeutically effective amount of the anti-VEGF agent is about 3 to 6 mg. In embodiments, the first, second and subsequent therapeutically effective amounts are the same. In embodiments, the first, second and subsequent therapeutically effective amounts are different.

In embodiments, the present invention provides an anti-VEGF agent, wherein the anti-VEGF agent is an Fc-IgG construct fusing domains with VEGF binding characteristics and domains that bind heparin proteoglycans. In embodiments, the present invention provides an anti-VEGF agent, wherein the anti-VEGF agent is an Fc-IgG construct having the ability to bind heparin and contains one or more domains with VEGF binding characteristics. In embodiments, the present invention provides an anti-VEGF agent, wherein the anti-VEGF agent is a fusion protein with improved efficacy for binding to VEGF and heparin. In embodiments, the present invention provides an anti-VEGF agent, wherein the anti-VEGF agent is a fusion protein with very low endotoxin levels.

In embodiments, the present invention provides an anti-VEGF agent, wherein the anti-VEGF agent is an IgG chimeric protein comprising elements of VEGF receptors. In embodiments, the present invention provides an IgG chimeric protein, wherein the IgG chimeric protein comprises one or more fragments of the seven immunoglobulin (Ig)-like domains in the extracellular portion of VEGF tyrosine kinase receptors. In embodiments, the present invention provides an IgG chimeric protein, wherein the IgG chimeric protein comprises one or more extracellular domain fragments of VEGFR-1 fused with Fc-IgG. In embodiments, the present invention provides an IgG chimeric protein comprising at least one VEGF binding domain VEGFR-1 domain 2 and at least one additional VEGFR-1 domain 1 or 3, and not including domain 4. In embodiments, the present invention provides an IgG chimeric protein, wherein the IgG chimeric protein comprises one or more extracellular domain fragments of VEGFR-2 fused with Fc-IgG. In embodiments, the present invention provides an IgG chimeric protein, wherein the IgG chimeric protein comprises one or more extracellular domain fragments of VEGFR-1 and VEGFR-2 fused with Fc-IgG.

In embodiments, the present invention provides an anti-VEGF agent comprising a VEGF binding portion operatively linked to a Fc-IgG, wherein the VEGF binding portion comprises at least one VEGF binding domain that is an IgG-like domain 2 of VEGFR-1, and wherein the anti-VEGF agent has a VEGF-stimulated mitogenesis-inhibiting ability greater than aflibercept. In embodiments, the present invention provides that the anti-VEGF agent has a vitreous binding ability greater than aflibercept. In embodiments, the present invention provides that the anti-VEGF agent has a vitreous bound VEGF-stimulated endothelial cell proliferation-inhibiting ability greater than aflibercept. In embodiments, the present invention provides that the agent has an increased half-life in vivo compared to aflibercept.

In embodiments, the present invention provides that the VEGF binding portion consists essentially of IgG-like domains 1, 2, and 3 of VEGFR-1 ($V_{1-2-3}$).

In embodiments, the present invention provides that the VEGF binding portion consists essentially of IgG-like domains 2 and 3 of VEGFR-1 ($V_{2-3}$).

In embodiments, the present invention provides that the VEGF binding portion consists essentially of IgG-like domains 1, 2, 3 and 3 of VEGFR-1 ($V_{1-2-3-3}$).

In embodiments, the present invention provides that the VEGF binding portion consists essentially of IgG-like domains 2, 3 and 3 of VEGFR-1 ($V_{2-3-3}$).

In embodiments, the present invention provides pharmaceutical compositions comprising a therapeutically effective amount of an anti-VEGF agent as defined claims and a pharmaceutically acceptable excipient. In embodiments, the present invention provides methods of treating a VEGF-related disorder in a subject in need comprising administering to the subject a therapeutically effective amount of an anti-VEGF agent as defined. The anti-VEGF agent can be directly injected into the affected tissue or organ, such as an eye.

In embodiments, the present invention provides a method for treating ocular disease, wherein an anti-VEGF agent is administered locally to the eye at a dosage corresponding to a molar ratio of 2:1 compared to VEGF. In embodiments, the present invention provides a method for treating ocular disease, wherein an anti-VEGF agent is administered by intravitreous injection.

In embodiments, the present invention provides a method for treating ocular disease, wherein an anti-VEGF agent is administered intravitreally once every 10-30 weeks. In embodiments, the anti-VEGF agent is administered intravitreally once every 16 to 24 weeks. In embodiments, the treatment is continued for a period of at least one year.

According to one embodiment, the present invention provides a method for treating ocular disease comprising administering a therapeutically effective amount of an anti-VEGF agent locally into the eye wherein the treatment is effective to treat occult, minimally classic, and predominantly classic forms of wet macular degeneration, wherein the agent is a fusion protein.

In embodiments the invention can be used to treat a wide variety of VEGF-related disorders including neovascular age related macular degeneration, choroidal neovascularization secondary to myopia, proliferative diabetic retinopathy, diabetic macular edema, retinal vascular obstruction such as retinal vein occlusion, ocular tumors, von Hippel Lindau syndrome, retinopathy of prematurity, polypoid choroidal vasculopathy, or non-neoplastic disorders that benefit from anti-VEGF therapy.

According to another aspect, the present invention provides a pharmaceutical formulation comprising an anti-VEGF agent in a pharmaceutically acceptable carrier formulation for local administration such as into the eye.

In embodiments, the present invention discloses novel constructs, wherein the constructs potently neutralize the activity of VEGF while, at the same time, have strong heparin-binding characteristics.

BRIEF DESCRIPTION OF THE DRAWINGS

FIG. 2A shows silver-stained SDS/PAGE (4-20% Tris) of our purified recombinant fusion proteins and EYLEA. 200 ng of each protein were subjected to electrophoresis under reducing conditions. Staining was performed by SilverQuest Silver Staining kit (Invitrogen). FIG. 2B shows an analytical size-exclusion chromatography (SEC) of V23, V233, V1233 and EYLEA, 25 μg of each. The Y-axis represents intensity of absorbance (A280) in milli-absorbance unit, and X-axis represents elution time in minutes.

FIG. 5A shows each protein was injected intravitreally in the mouse at the dose of 2.5 μg one day before laser treatment. EYLEA was tested also at 25 μg. Asterisks denote significant differences (Student's t test) compared to the appropriate IgG control groups (**p<0.01, *p<0.05). Data are based on three independent experiments with at least 5 mice per group. Note that the efficacy of EYLEA is in line with the published literature in the same model. FIG. 5B shows effect of the time of injection prior to injury on CNV area. EYLEA at the dose of 2.5 μg had a significant reduction only when injected at day −1. In contrast, V1233 at the same dose significantly reduced CNV area even when injected 7 days or 14 prior to the injection. The left panel show representative CD31 immunofluorescence images. Asterisks denote significant differences (Student's t test) compared to the appropriate IgG control groups (**p<0.01, *p<0.05). n=5. Similar results were obtained in two independent experiments. FIG. 5C shows V23, V233 and V1233, tested at equimolar doses (4.8 μg of EYLEA and V23, 6.3 μg of V233 and 7.2 μg of V1233), show greater efficacy compared to EYLEA. All agents were administered 14 days prior to the laser treatment. Seven days later, eyes were harvested, and data were analyzed. Asterisks denote significant differences (Student's t test) compared to the appropriate IgG control groups (**p<0.01, *p<0.05). FIG. 5D shows serum levels of EYLEA, V23, V233 or V1233 in mice at different time points after intravitreal injection. Each molecule was injected in both eyes in equimolar amounts: 2.4 mg of EYLEA and V23, 3.15 mg of V233 and 3.6 mg of V1233. After 1 day, 3 days, 7 days, 14 days and 21 days, peripheral blood was collected from the tail vein. Human Fc levels were measured by ELISA. Values shown are means±SEM. *, p<0.05; , p<0.01; *, p<0.001. n=8 per point.

FIG. 6A shows intravitreal injections were performed at P7 in C57BL/6j mice using aflibercept, V1233, and control (IgG). A volume of 0.5 pl aflibercept (E) at a dose of 12.5 μg, 2.5 μg, or 1.25 μg versus control IgG at a dose of 3.25 μg injected into the fellow eyes. Littermates were injected with V1233 (3.8 μg or 1.65 pg) and control. The concentrations of IgG control, aflibercept 2.5 μg and V1233 3.8 μg were equimolar (see also FIG. 10 legend). Animals were then exposed to 75% oxygen from P7 to P12 followed by return to room air. At P17, the animals were perfusion fixed, and the eyes were enucleated, dissected, stained with BSL-FITC and flat mounted. FIG. 6B shows vasoobliteration and neovascularization were analyzed using automated software as described by Xiao et al. (ref. 116). The vasoobliterative areas are shown in yellow, and neovascular tufts are shown in red. FIG. 6C shows quantification of neovascularization shows a significant reduction (p<0.05 t-test with Welch's correction) in neovascularization relative to control with V1233 (3.8 and 1.65 pg) or high dose aflibercept (12.5 μg), but not with aflibercept at 2.5 or 1.25 μg.

FIG. 14 depicts the amino acid sequence and nucleic acid sequence of the entire human IgG1-Fc fragment and VEGFR-1 domain of construct V1-2-3. SEQ ID No: 1 and SEQ ID No: 2, respectively Amino acid sequences and nucleic acid sequences for the IgG-like domains of VEGFR-1 are provided within the Figure, as described. The amino acid sequence of $V_1$ is SEQ ID No: 15, the amino acid sequence of construct $V_2$ is SEQ ID No: 16, and the amino acid sequence of construct $V_3$ is SEQ ID No: 17.

FIG. 15 depicts the amino acid sequence and nucleic acid sequence of the entire human IgG1-Fc fragment and VEGFR-1 domain of construct $V_{2-3}$. SEQ ID No: 3 and SEQ ID No: 4, respectively Amino acid sequences and nucleic acid sequences for the IgG-like domains of VEGFR-1 are provided within the Figure, as described. The amino acid sequence of $V_2$ is SEQ ID No: 16, and the amino acid sequence of $V_3$ is SEQ ID No: 17.

FIG. 16 depicts the amino acid sequence and nucleic acid sequence of the entire human IgG1-Fc fragment and VEGFR-1 domain of construct $V_{1-2-3-3}$. SEQ ID No: 5 and SEQ ID No: 6, respectively Amino acid sequences and nucleic acid sequences for the IgG-like domains of VEGFR-1 are provided within the Figure, as described. The amino acid sequence of $V_1$ is SEQ ID No: 15, the amino acid sequence of $V_2$ is SEQ ID No: 16, and the amino acid sequence of $V_3$ is SEQ ID No: 17.

FIG. 17 depicts the amino acid sequence and nucleic acid sequence of the entire human IgG1-Fc fragment and VEGFR-1 domain of construct $V_{2-3-3}$. SEQ ID No: 7 and SEQ ID No: 8, respectively Amino acid sequences and nucleic acid sequences for the IgG-like domains of VEGFR-1 are provided within the Figure, as described. The amino acid sequence of $V_2$ is SEQ ID No: 16, and the amino acid sequence of $V_3$ is SEQ ID No: 17.

FIG. 18 depicts the amino acid sequence and nucleic acid sequence of the entire human IgG1-Fc fragment and VEGFR-1 domain of construct $V_{1-2-3-3-4}$. SEQ ID No: 9 and SEQ ID No: 10, respectively Amino acid sequences and nucleic acid sequences for the IgG-like domains of VEGFR-1 are provided within the Figure, as described. The amino acid sequence of $V_1$ is SEQ ID No: 15, the amino acid sequence of $V_2$ is SEQ ID No: 16, the amino acid sequence of $V_3$ is SEQ ID No: 17, and the amino acid sequence of $V_4$ is SEQ ID No: 18.

FIG. 19 depicts the amino acid sequence and nucleic acid sequence of the entire human IgG1-Fc fragment and VEGFR-1 domain of construct $V_{2-3-4}$. SEQ ID No: 11 and SEQ ID No: 12, respectively. The amino acid sequence of construct $V_2$ is SEQ ID No: 16, the amino acid sequence of $V_3$ is SEQ ID No: 17, and the amino acid sequence of $V_4$ is SEQ ID No: 18.

FIG. 20 depicts the amino acid sequence and nucleic acid sequence of the entire human IgG1-Fc fragment and VEGFR-1 domain of construct $V_{2-4}$. SEQ ID No: 13 and SEQ ID No: 14, respectively. The amino acid sequence of $V_2$ is SEQ ID No: 16, and the amino acid sequence of $V_4$ is SEQ ID No: 18.

DETAILED DESCRIPTION

Figure 1:
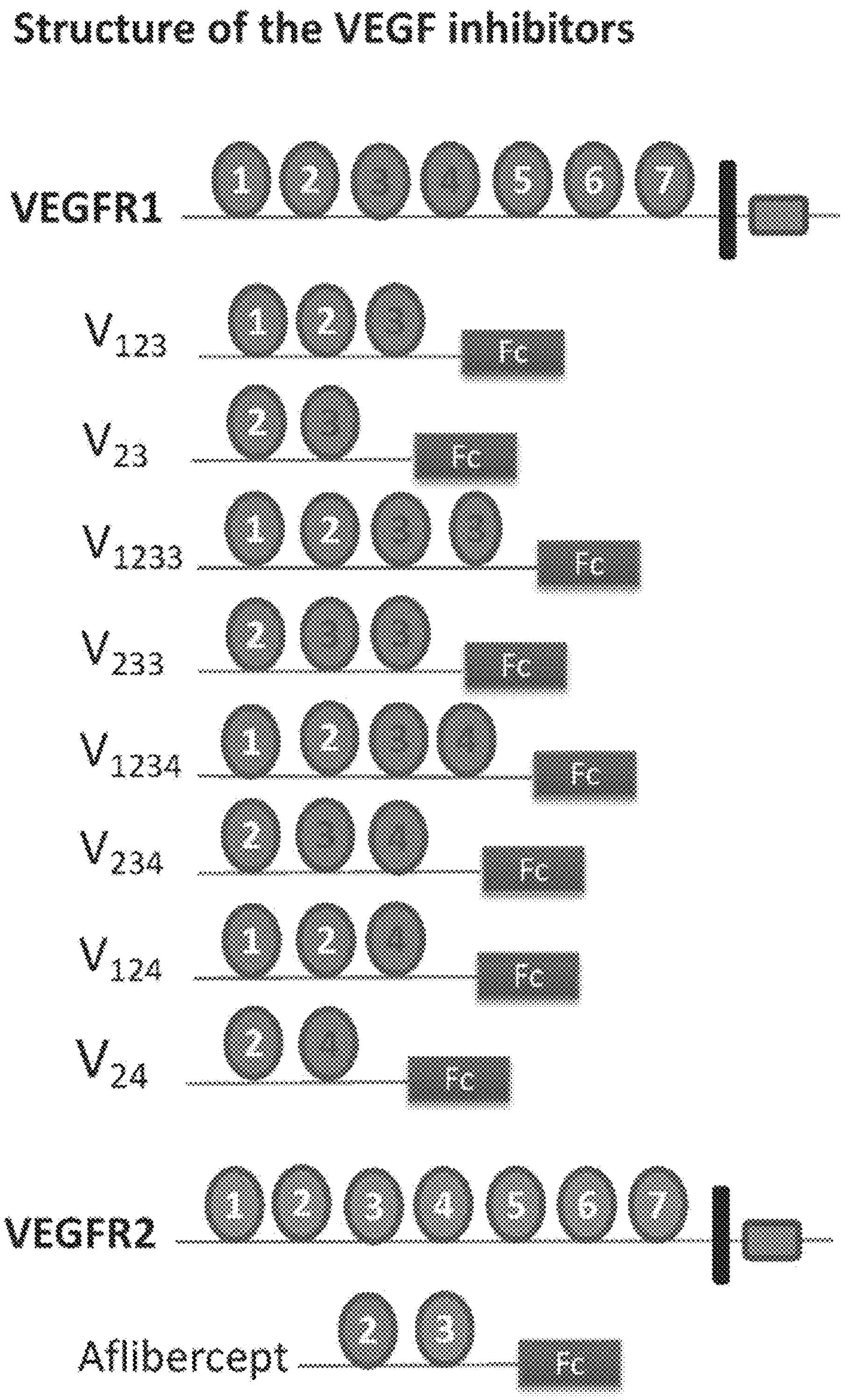
FIG. 1 shows Immunoglobulin (Ig)-like domain (D) organization of VEGFR1 and of the Fc-fusion constructs designed in our study. Red label denotes heparin-binding domain. D2 is an indispensable binding element for VEGF and P1GF, responsible for ligand specificity[27]. D3 plays an important role in binding affinity and stability[27 28 30]. D3 of VEGFR1, but not D3 of VEGFR2, is a major heparin-binding site. V23 and aflibercept (EYLEA) differ only in D3, which is from VEGFR2 in aflibercept. D4 is also a heparin-binding site, implicated in receptor dimerization and homotypic interactions[30]. Each construct is shown as a monomer for simplicity, but the recombinant proteins are dimers due the forced dimerization imposed by the Fc.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, $20^{th}$ ed., (Lippincott, Williams & Wilkins 2003), and Remington, The Science and Practice of Pharmacy, $22^{th}$ ed., (Pharmaceutical Press and Philadelphia College of Pharmacy at University of the Sciences 2012).

As used herein, the terms "comprises," "comprising," "includes," "including," "has," "having," "contains", "containing," "characterized by," or any other variation thereof, are intended to encompass a non-exclusive inclusion, subject to any limitation explicitly indicated otherwise, of the recited components. For example, a fusion protein, a pharmaceutical composition, and/or a method that "comprises" a list of elements (e.g., components, features, or steps) is not necessarily limited to only those elements (or components or steps), but may include other elements (or components or steps) not expressly listed or inherent to the fusion protein, pharmaceutical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a fusion protein, pharmaceutical composition, and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It is understood that aspects and embodiments of the invention described herein include "consisting" and/or "consisting essentially of" aspects and embodiments.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein, "patient" or "subject" means a human or animal subject to be treated.

As used herein the term "pharmaceutical composition" refers to pharmaceutically acceptable compositions, wherein the composition comprises a pharmaceutically active agent, and in some embodiments further comprises a pharmaceutically acceptable carrier. In some embodiments, the pharmaceutical composition may be a combination of pharmaceutically active agents and carriers.

The term "combination" refers to either a fixed combination in one dosage unit form, or a kit of parts for the combined administration where one or more active compounds and a combination partner (e.g., another drug as explained below, also referred to as "therapeutic agent" or "co-agent") may be administered independently at the same time or separately within time intervals. In some circumstances, the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein the term "pharmaceutically acceptable" means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

As used herein the term "pharmaceutically acceptable carrier" refers to an excipient, diluent, preservative, solubilizer, emulsifier, adjuvant, and/or vehicle with which demethylation compound(s), is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

As used herein, "therapeutically effective amount" refers to an amount of a pharmaceutically active compound(s) that is sufficient to treat or ameliorate, or in some manner reduce the symptoms associated with diseases and medical conditions. When used with reference to a method, the method is sufficiently effective to treat or ameliorate, or in some manner reduce the symptoms associated with diseases or conditions. For example, an effective amount in reference to diseases is that amount which is sufficient to block or prevent onset; or if disease pathology has begun, to palliate, ameliorate, stabilize, reverse or slow progression of the disease, or otherwise reduce pathological consequences of the disease. In any case, an effective amount may be given in single or divided doses.

As used herein, the terms "treat," "treatment," or "treating" embraces at least an amelioration of the symptoms associated with diseases in the patient, where amelioration is used in a broad sense to refer to at least a reduction in the magnitude of a parameter, e.g. a symptom associated with the disease or condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

As used herein, the term "therapeutic agent," "anti-VEGF agent," "fusion protein," "chimeric protein," or "recombinant protein" comprises a first polypeptide operatively linked to a second polypeptide, wherein the "therapeutic agent," "anti-VEGF agent," "fusion protein," "chimeric protein," or "recombinant protein" inhibits the activity of VEGF. Chimeric proteins may optionally comprise a third, fourth or fifth or other polypeptide operatively linked to a first or second polypeptide. Chimeric proteins may comprise two or more different polypeptides. Chimeric proteins may comprise multiple copies of the same polypeptide. Chimeric proteins may also comprise one or more mutations in one or more of the polypeptides. Methods for making chimeric proteins are well known in the art. In some embodiments the term "therapeutic agent," "fusion protein," "chimeric protein," or "recombinant protein" refers to any constructs expressed or synthesized, including but not limited to, peptides or proteins operatively linking one or more of the Ig-like domains or domain fragments of VEGFR-1 and/or VEGFR-2 with Fc-IgG.

The term "Ig-like domains" refers to Ig-like domains 1-7 of VEGFR-1 and VEGFR-2. The term "Ig-like domain fragments" comprise a portion of a full length domain, generally the heparin and/or VEGF binding or variable region thereof. Examples of domain fragments include amino acid sequences comprising a segment of at least 75%, more preferably at least 80%, 90%, 95%, and most preferably 99% of the full length domain with 100% sequence identity and variations thereof. Variations in the amino acid sequences of fusion proteins are contemplated as being encompassed by the present disclosure, providing that the variations in the amino acid sequence maintain at least 75%, more preferably at least 80%, 90%, 95%, and most preferably 99%. Certain percentages in between are included, such as 75%, 76%, 77%, 78%, 79% 80%, 81%, 82%, 83%, 84%, 85%, 86%, 87%, 88%, 89%, 90%, 91%, 92%, 93%, 94%, 95%, 96%, 97%, 98%, and 99% sequence identity. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional fusion protein can readily be determined by assaying the specific activity of the fusion protein derivative. Fragments or analogs of fusion proteins can be readily prepared by those of ordinary skill in the art. Preferred amino- and carboxy-termini of fragments or analogs occur near boundaries of functional domains.

As used herein, an "isolated" or "purified" fusion protein means the fusion protein is the predominant species present (i.e., on a molar basis it is more abundant than any other individual species in the composition), and preferably a substantially purified fraction is a composition wherein the fusion protein comprises at least about 50% (on a molar basis) of all macromolecular species present. Generally, a purified composition will comprise more than about 80% of all macromolecular species present in the composition, more preferably more than about 85%, 90%, 95%, and 99%. Most preferably, the fusion protein is purified to essential homogeneity (contaminant species cannot be detected in the composition by conventional detection methods) wherein the composition consists essentially of a single macromolecular species.

In one aspect the present invention discloses a composition comprising a therapeutic agent, where the therapeutic agent comprises one or more heparin binding domains of VEGFR-1 or VEGFR-2, and one or more VEGF binding domains, thereby inhibiting the binding of VEGF to its cognate receptor. In embodiments, the anti-VEGF agent comprises a VEGF binding portion operatively linked to a Fc-IgG, wherein the VEGF binding portion comprises at least one VEGF binding domain that is an IgG-like domain 2 of VEGFR-1.

In embodiments, the present invention provides compositions and methods for treating a VEGF-related ophthalmic disorder in a subject in need comprising, administering intravitreally to the subject a first therapeutically effective amount of an anti-VEGF agent, and administering intravitreally to the subject a second therapeutically effective amount of the anti-VEGF agent within more than 8 weeks, or within between 10 to 30 weeks of the earlier administration. In embodiments, the second therapeutically effective amount of the anti-VEGF agent is administered intravitreally within 16 to 24 weeks of the earlier administration. In embodiments, the method comprises subsequent administrations of the therapeutically effective amount of the anti-VEGF agent administered intravitreally within 10 to 30 weeks of a prior administration for a period of at least one year. The invention provides such dosing regimens as may be required for any particular individual subject in need thereof, wherein the second and subsequent administrations are less frequent than required for an equimolar amount of aflibercept due to a greater heparin binding efficiency than aflibercept. The invention further provides that following intraocular administration, plasma levels of the anti-VEGF agents in an individual are lower than plasma levels of aflibercept in an individual following intraocular administration of an equimolar amount of aflibercept, which avoids undesirable systemic effects, such as detrimental neurodevelopmental effects.

In embodiments, the therapeutically effective amount of the anti-VEGF agent is about 1 to 10 mg. In embodiments, the therapeutically effective amount of the anti-VEGF agent is about 3 to 6 mg. In embodiments, the first, second and subsequent therapeutically effective amounts are the same. In embodiments, the first, second and subsequent therapeutically effective amounts are different. The invention provides such dosages of therapeutically effective amounts as may be required for any particular anti-VEGF agent for any particular individual subject in need thereof.

In embodiments, the present invention provides an anti-VEGF agent comprising a VEGF binding portion operatively linked to a Fc-IgG, wherein the VEGF binding portion comprises at least one VEGF binding domain that is an IgG-like domain 2 of VEGFR-1, and wherein the anti-VEGF agent has a VEGF-stimulated mitogenesis-inhibiting ability greater than aflibercept. In embodiments, the present invention provides that the anti-VEGF agent has a vitreous binding ability greater than aflibercept. In embodiments, the present invention provides that the anti-VEGF agent has a vitreous bound VEGF-stimulated endothelial cell proliferation-inhibiting ability greater than aflibercept. In embodiments, the present invention provides that the agent has an increased half-life in vivo compared to aflibercept.

VEGFR VEGF binding domains are well known in the art. Exemplary amino acid sequences and nucleic acid sequences for the IgG-like domains $V_1$, $V_2$, $V_3$, and $V_4$ of VEGFR-1 are provided within FIGS. 14-20, respectively which present the entire human IgG1-Fc fragment and VEGFR-1 domains, as described. Amino acid sequences for the individual human IgG-like domains $V_1$, $V_2$, $V_3$, and $V_4$ of VEGFR-1 are also individually provided in SEQ ID Nos: 15-18, respectively. The amino acid sequence of $V_1$ is SEQ ID No: 15 (the yellow greyscale amino acid sequence in FIG. 14, which is within SEQ ID No: 1). The amino acid sequence of $V_2$ is SEQ ID No: 16 (the blue greyscale amino acid sequence in FIG. 14, which is within SEQ ID No: 1). The amino acid sequence of $V_3$ is SEQ ID No: 17 (the grey greyscale amino acid sequence in FIG. 14, which is within SEQ ID No: 1). The amino acid sequence of $V_4$ is SEQ ID No: 18 (the green greyscale amino acid sequence in FIG. 18, which is within SEQ ID No: 9)

In embodiments, the present invention provides that the VEGF binding portion consists essentially of IgG-like domains 1, 2, and 3 of VEGFR-1 ($V_{1-2-3}$). In embodiments, the anti-VEGF agent comprises amino acid sequence as defined in SEQ ID No: 1.

In embodiments, the present invention provides that the VEGF binding portion consists essentially of IgG-like domains 2 and 3 of VEGFR-1 ($V_{2-3}$). In embodiments, the anti-VEGF agent comprises amino acid sequence as defined in SEQ ID No: 3.

In embodiments, the present invention provides that the VEGF binding portion consists essentially of IgG-like domains 1, 2, 3 and 3 of VEGFR-1 ($V_{1-2-3-3}$). In embodiments, the anti-VEGF agent comprises amino acid sequence as defined in SEQ ID No: 5.

In embodiments, the present invention provides that the VEGF binding portion consists essentially of IgG-like domains 2, 3 and 3 of VEGFR-1 ($V_{2-3-3}$). In embodiments, the anti-VEGF agent comprises amino acid sequence as defined in SEQ ID No: 7.

In embodiments, the invention provides a pharmaceutical composition for use in treating a VEGF-related ophthalmic disorder in a subject in need, wherein the anti-VEGF agent is as defined herein. In embodiments, the present invention provides pharmaceutical compositions comprising a therapeutically effective amount of an anti-VEGF agent as defined claims and a pharmaceutically acceptable excipient. In embodiments, the present invention provides methods of treating a VEGF-related disorder in a subject in need comprising administering to the subject a therapeutically effective amount of an anti-VEGF agent as defined. The anti-VEGF agent can be directly injected into the affected tissue or organ, such as an eye.

In embodiments, the present invention provides a method for treating ocular disease, wherein an anti-VEGF agent is administered intravitreally more than once every 16 weeks. In embodiments, the anti-VEGF agent is administered intravitreally more than once every 16 to 24 weeks. In embodiments, the treatment is continued for a period of at least one year. In embodiments, the therapeutically effective amount of the anti-VEGF agent is about 1 to 10 mg. In embodiments, the therapeutically effective amount of the anti-VEGF agent is about 3 to 6 mg.

In embodiments the invention can be used to treat a wide variety of VEGF-related disorders including neovascular age related macular degeneration, choroidal neovascularization secondary to myopia, proliferative diabetic retinopathy, diabetic macular edema, retinal vascular obstruction such as retinal vein occlusion, ocular tumors, von Hippel Lindau syndrome, retinopathy of prematurity, polypoid choroidal vasculopathy, or non-neoplastic disorders that benefit from anti-VEGF therapy.

In some embodiments, the therapeutic agent is in an administrable dosage form, comprising the therapeutic agent, and an additional excipient, carrier, adjuvant, solvent, or diluent.

In some embodiments, the present invention discloses a pharmaceutical composition suitable for treating and/or preventatively treating a subject, wherein the anti-VEGF agent is contained in an amount effective to achieve its intended purpose.

In some embodiments, the therapeutic agent or compositions disclosed herein are administered by injection. In certain embodiments, the compositions or the therapeutic agent are injected directly into the diseased organ or tissue. In some embodiments, the therapeutic agent can be topically administered, for example, by patch or direct application to the diseased organ or tissue, or by iontophoresis. The therapeutic agents may be provided in sustained release compositions, such as those described in, for example, U.S. Pat. Nos. 5,672,659 and 5,595,760. The use of immediate or sustained release compositions depends on the nature of the condition being treated. If the condition consists of an acute or over-acute disorder, treatment with an immediate release form will be preferred over a prolonged release composition. Alternatively, for certain preventative or long-term treatments, a sustained released composition may be appropriate.

The anti-VEGF agent may also be delivered using an implant, such as but not limited to an intraocular implant. Such implants may be biodegradable and/or biocompatible implants, or may be non-biodegradable implants. The implants may be permeable or impermeable to the active agent. The specific implants for delivery of the therapeutic agent is dependent on both the affected tissue or organ as well as the nature of the condition being treated. The use of such implants is well known in the art.

The anti-VEGF agent described in this invention can be formulated in nanoparticles or other drug formulations in order to provide precise delivery to specific tissues and also provide controlled release therapy.

The anti-VEGF agent described in this application can be delivered not only as purified recombinant proteins but also by a gene therapy approach. Recombinant adeno-associated vectors (rAAVs) or other suitable vectors can be used to deliver the VEGF inhibitor by sub-retinal or intravitreal delivery[43,44].

In a related aspect, the present invention provides a method for treating a VEGF-related or neovascular disorder in a subject, wherein the method involves administering to the subject: (a) an effective amount of a fusion protein capable of binding heparin and diminishing or preventing the development of unwanted neovasculature. The fusion protein may be combined with other anti-VEGF agents including, but are not limited to: antibodies or antibody fragments specific to VEGF; antibodies specific to VEGF receptors; compounds that inhibit, regulate, and/or modulate tyrosine kinase signal transduction; VEGF polypeptides; oligonucleotides that inhibit VEGF expression at the nucleic acid level, for example antisense RNAs; and various organic compounds and other agents with angiogenesis inhibiting activity.

The invention provides that heparin-binding mediated by D3 (or other Ig-like domain) of VEGFR1[28], while a disadvantage for systemic administration, can confer important advantages for intravitreal (or other local) administration. Indeed, the ability to bind HGPSG, key components of the extracellular matrix[29], promotes accumulation in the vitreous as well as retinal penetration[30]. The invention provides a series of VEGFR-1 Fc fusion constructs having differential abilities to interact with HSPGs. This enables election of VEGF inhibitors with different duration/half-life in the eye, which are useful under difference clinical conditions.

The features and other details of the invention will now be more particularly described and pointed out in the following examples describing preferred techniques and experimental results. The examples are provided for the purpose of illustrating the invention and should not be construed as limiting.

EXAMPLES

To identify more effective and longer-lasting VEGF inhibitors for intraocular use, the diversity of heparin-binding in VEGFR1 Ds was studied. To this end, eight VEGFR1-Fc fusion constructs were designed having differential heparin binding, thus providing a spectrum of HPSG affinity. FIG. 1 illustrates the domain structure of these protein and highlights heparin-binding domains. All proteins include D2, the key determinant of ligand specificity[27]. Two constructs (V1233 and V233) have a duplicated D3. The domain structure of aflibercept is also shown.

In initial experiments, the expression levels of several of constructs were low; V1234, V1233, V234 and V124 were detectable at low levels in the conditioned media. Interestingly, earlier studies had shown that VEGF isoforms with high affinity for heparin (VEGF189 or VEGF206) are almost undetectable in the conditioned media of transfected cells, being largely bound to the cells surface or the extracellular matrix[38 9]. However, they could be released in a soluble form by the addition of heparin or heparinase, indicating that the binding site consisted of HSPG[38 9]. Thus, it was determined whether the addition of heparin may also affect the levels of recombinant VEGFR-1 fusion proteins. Indeed, adding heparin to the media of transfected cells resulted in dose-dependent increases in the concentrations of recombinant protein in the medium (data not shown).

Figure 2A:
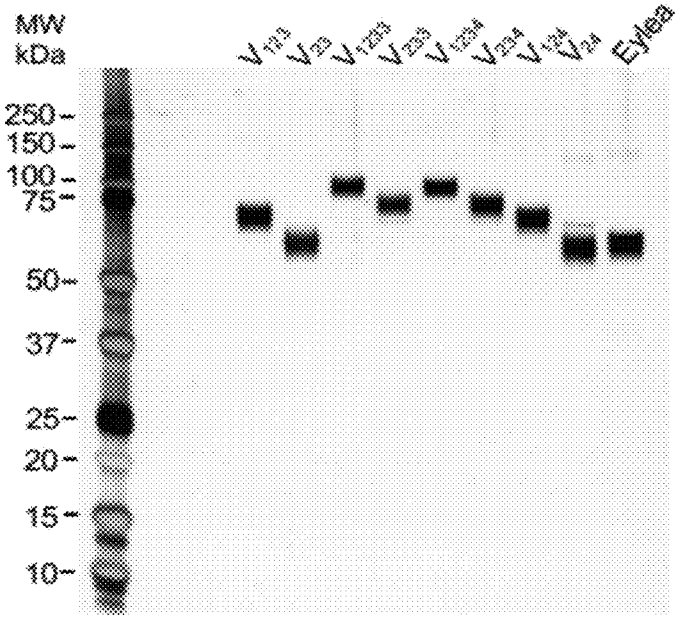
FIGS. 2A-2B show characterization of purified recombinant proteins.
Figure 2B:
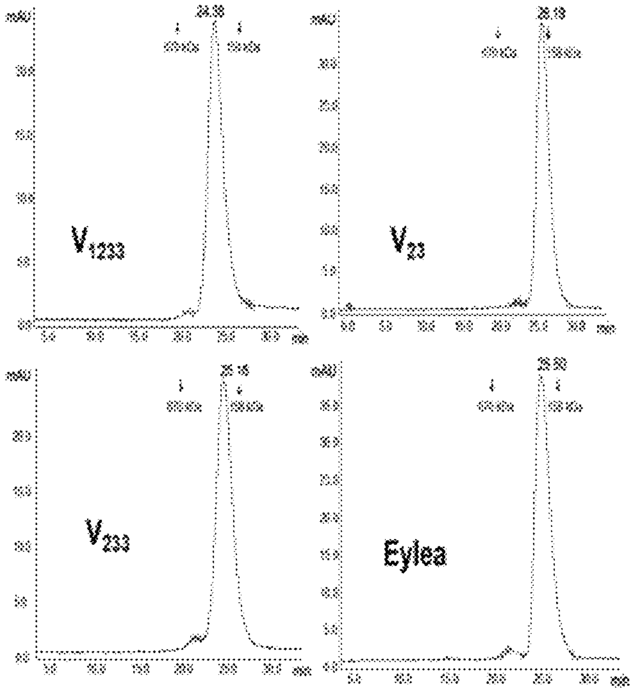

Purification of the recombinant proteins simply by conventional protein A (PA) affinity chromatography was attempted. However, this method yielded a major band of the expected mass and numerous other minor bands, likely reflecting the interaction of the strongly basic, heparin-binding, recombinant proteins with host cell-derived HSPGs and other anionic molecules. Therefore, a protocol was developed that removed such impurities, as described in Methods. A wash at high pH (9.2), in the presence of 1.2 M NaCl, while the protein is bound to PA, resulted in release of numerous contaminants. The next step, anion exchange chromatography, was very effective at removing the bulk of contaminants and aggregates, while the purified protein was in the flow-through. The LPS levels in the final purified preparations were <0.1 EU/mg (range 0.02-0.08), a very low level compatible with preclinical studies[39]. As shown in FIG. 2A, the purity of the recombinant proteins was >95%, as assessed by silver-stained SDS/PAGE and was similar to that of the FDA-approved drug EYLEA. FIG. 2B shows analytical SEC profiles of the three most promising candidates, V23, V1233 and V233, next to EYLEA. Similar to EYLEA, the three proteins eluted as a single peak at the expected retention time, without significant aggregation.

Figure 3:
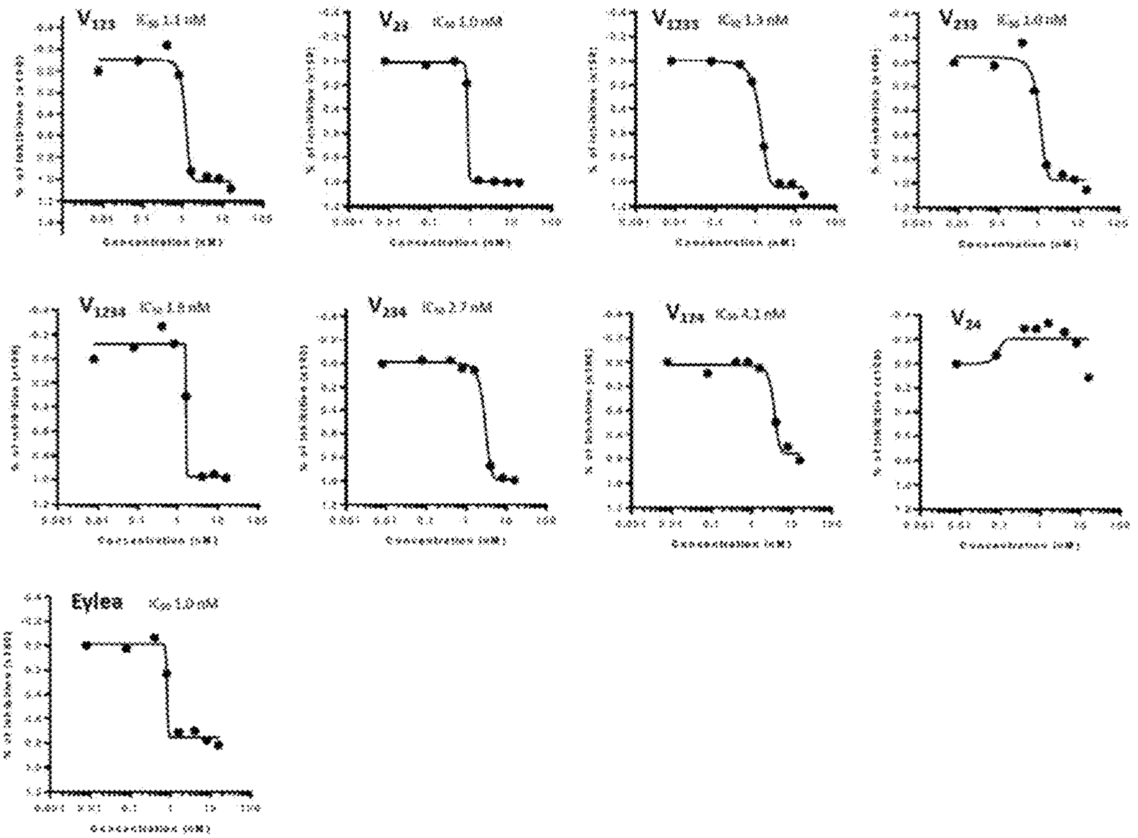
FIG. 3 shows $IC_{50}$ values of the inhibitors. Bovine choroidal endothelial cells were maintained as described in Approach For assays, cells are plated at low density. Inhibitors are then added at various concentrations as indicated in the figure. VEGF is added at the final concentration of 10 ng/ml. Cell densities are evaluated after 5 days. IC50 values were calculated using GraphPad Prism 5 (GraphPad Software, CA). Data shown are based on two independent experiments obtained with highly purified proteins and are consistent with numerous previous assays.
Figure 7:
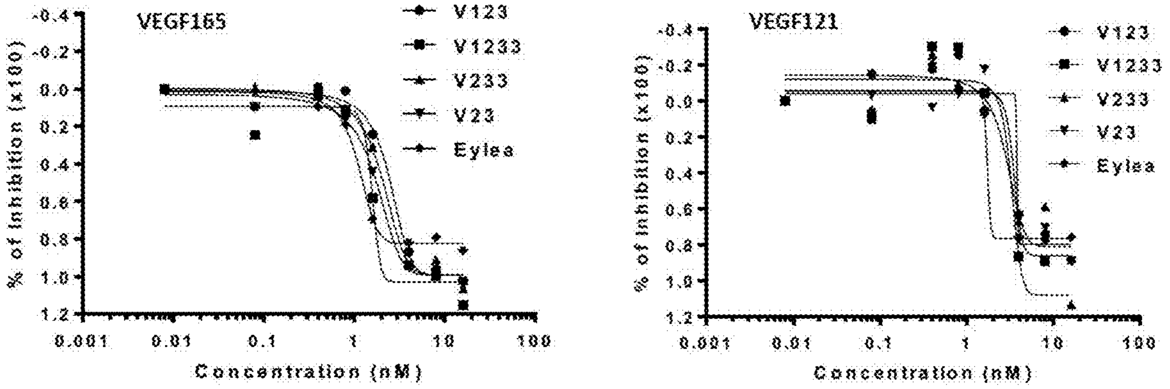
FIG. 7 shows inhibitory effects of fusion protein on BCEC proliferation stimulated by VEGF165 or VEGF121. Results are expressed as % of inhibition of VEGF-stimulated proliferation relative to control. Cell numbers were determined by relative fluorescence unit (RFU) 530/590 (Excitation/Emission), average of triplicates.
Figure 8:
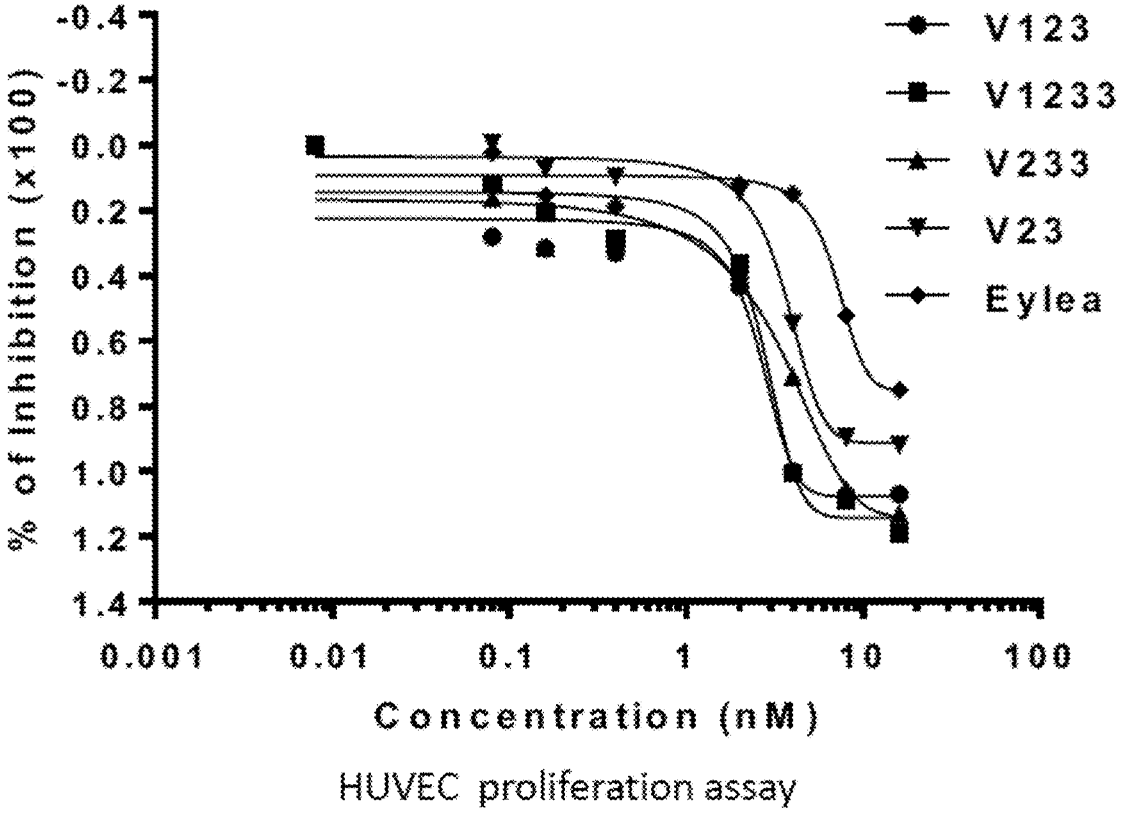
FIG. 8 shows inhibitory effects of recombinant VEGF receptor Fc-fusion proteins on HUVEC proliferation. V123, V1233, V233, V23 or EYLEA (10-2000 ng/ml) was added along with VEGFI65 (10 ng/ml) for 3 days, and cell viability was determined. Results are expressed as % of inhibition of VEGF-stimulated proliferation relative to control. Cell numbers were determined by relative fluorescence unit (RFU) 530/590 (Excitation/Emission), average of triplicates. Statistical analysis was performed by 2-Way ANOVA in GraphPad Prism software. Statistical significance *p<0.001, **p<0.0001 was calculated by comparing with VEGF alone.
Figure 9:
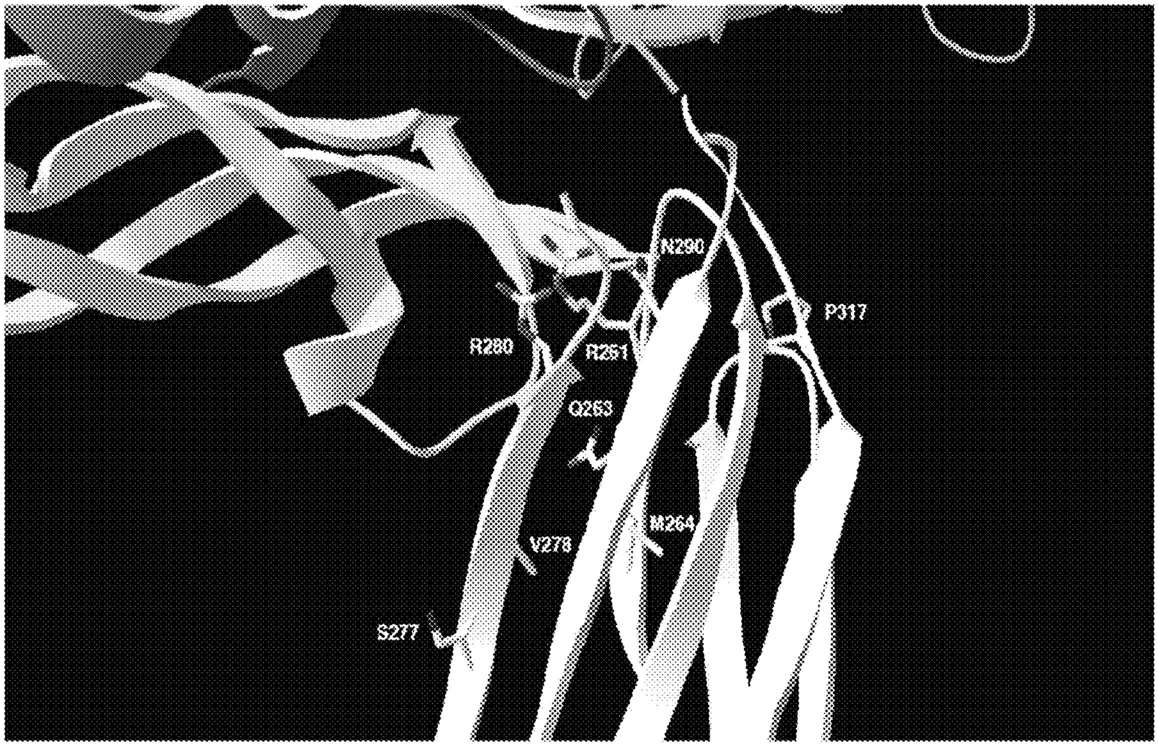
FIG. 9 shows crystal structure of VEGF/VEGFR2 complex (3V2A) was superimposed on the crystal structure of the VEGF/VEGFR1 complex (5T89). VEGFR1 residues that can potentially interact with VEGF and that differ between VEGFR1 and VEGFR2 are labeled. Yellow and blue greyscales: VEGF. Green greyscale: VEGFR1 D2. White: VEGFR1 D3. Analysis points to a more extensive interaction between VEGF and VEGFR1 D3 compared to VEGFR2 D3.

The recombinant proteins were tested for their ability to inhibit mitogenesis induced by VEGF165 (10 ng/ml) in BCEC. As illustrated in Fig., they had inhibitory effects, with $IC_{50}$ values were in the range of ~1 nM, except for V124 and V24, which were less potent (FIG. 3). We also documented their ability to inhibit BCEC mitogenesis stimulated by VEGF121 (FIG. 7). Interestingly, EYLEA, in nearly all experiments performed (>10) was potent, being active at low concentrations, with $IC_{50}$ of ~1 nM, but inhibited no more than ~80% of VEGF-stimulated proliferation even at the highest concentrations tested. Similar results were obtained using HUVEC proliferation assays (FIG. 8). In contrast, the VEGFR1 constructs, (except, V124 and V24), completely blocked VEGF-induced proliferation. The ability to detect such differences likely reflects the relatively high dynamic range of our BCEC proliferation assay in response to VEGF stimulation (~4-fold increase). VEGFR1 D3 may provide a better interactive surface than D3 from VEGFR2, especially considering that VEGFR1 binds VEGF significantly more effectively than VEGFR2[40 41] To test this hypothesis, a comparison was performed of Protein Data Bank Files of the VEGFR1/VEGF complex (5T89)[30] and VEGFR2/VEGF complex (3V2A)[42] and superimposed D2-D3 from each receptor. This analysis supports the hypothesis. For example, Arg280 in VEGFR1-D3 interacts with the sidechain of VEGF Phe36, whereas VEGFR2 has an Asp there. Likewise, in VEGFR1 both Arg261 and Asn290 interact with VEGF Glu64; in VEGFR2 the Arg261 is replaced by Gly and hence in VEGFR2 only the Lys replacing Asn290 can interact with VEGF Glu64. FIG. 9 illustrates the VEGFR1 residues that can potentially interact with VEGF and that differ between VEGFR1 and VEGFR2.

Figure 4:
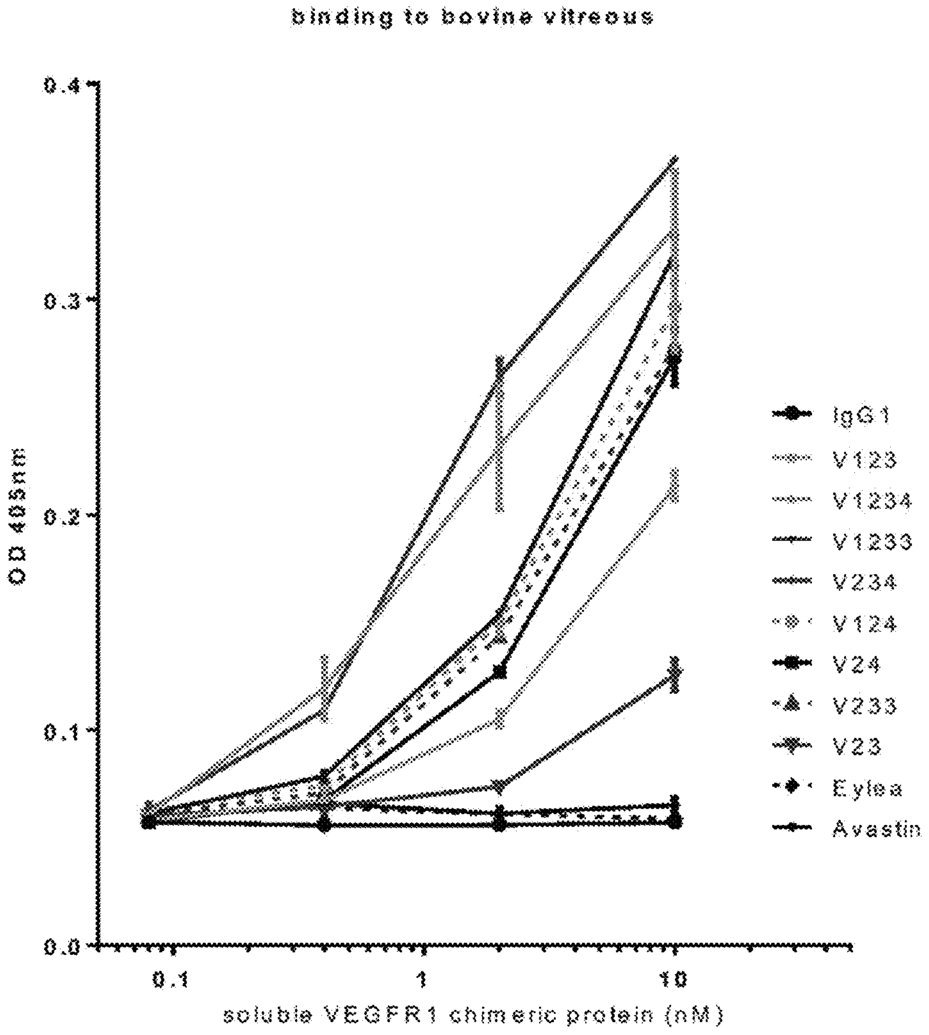
FIG. 4 shows binding to bovine vitreous.

To further define therapeutically relevant interactions, it was assessed whether the recombinant proteins bind bovine vitreous in vitro. As illustrated in FIG. 4, while EYLEA, control IgG or bevacizumab had little or no binding, our proteins showed significant binding. The strongest binders were V1233, V233 and V1234, followed by V123. V23 had intermediate binding characteristics, between EYLEA (or control IgG) and V1233. Vitreous binding was displaced by heparin in a dose-dependent manner.

Figure 5A:
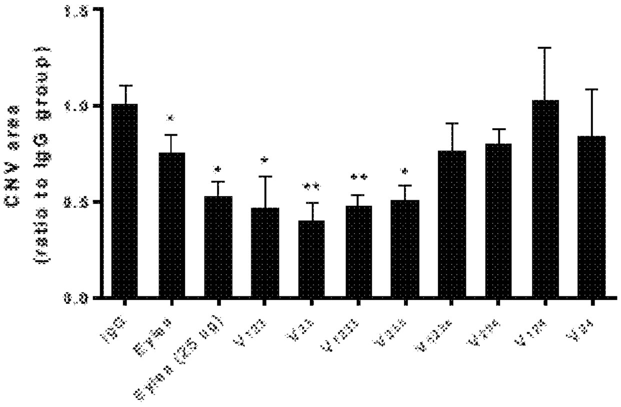
FIGS. 5A-5D show effects of control IgG, EYLEA or VEGFR1 Fc fusion proteins on laser-induced choroidal neovascularization (CNV) in adult mice.

Recombinant proteins were tested in the mouse CNV model and compared to control IgG or EYLEA. An extensive literature documents the ability of anti-VEGF agents to suppress neovascularization in this model[43 44 45]. Relatively low doses were chosen for proof-of-concept studies, being best suited to reveal potency and durability differences among the various proteins. Also, it has been reported that intravitreal administration of high doses of antibodies of the IgG1 isotype may have off-target angio-inhibitory effects, mediated by Fc signaling through FcgRI and c-Cbl, leading to impaired macrophage migration[46]. These effects might potentially confound the interpretation of the data. The doses employed are efficacious and at the same time should avoid such off-target effects. Initially, each protein was injected intravitreally at the dose of 2.5 μg one day before laser treatment. EYLEA was tested also at 25 μg. As illustrated in FIG. 5A, EYLEA resulted in an approximately 30% inhibition at the dose of 2.5 μg and ~50% inhibition at the dose of 25 μg. These findings are largely consistent with the published literature. For example, Saishin et al. reported that the intravitreal injection of ~5 μg of aflibercept resulted in ~30% inhibition of CNV area in the mouse[44]. Indeed, the dose of 40 μg is commonly used to achieve maximal inhibitory effects of aflibercept in the mouse CNV model[47].

An unexpected finding was the greater potency of some of the constructs: V123, V23, V1233 and V233. Administering 2.5 μg of these proteins, one day before the injury, matched or even exceeded the level of inhibition achieved with 25 μg of EYLEA. However, none of the constructs that included D4 demonstrated significant CNV inhibition (FIG. 5A).

Figure 5B:
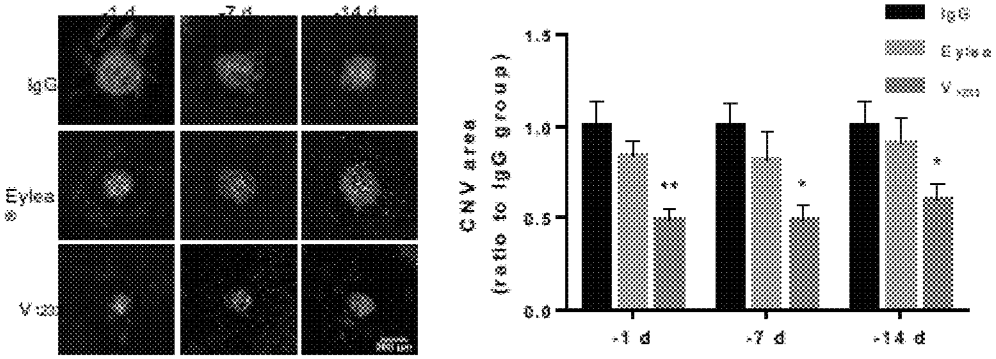

To determine whether heparin-binding may translate in durable therapeutic effects following a single administration, V1233, EYLEA or control IgG, were injected intravitreally (2.5 μg) 1 day, 7 days or 14 days before the laser-induced injury. As shown in FIG. 5B, EYLEA resulted in a significant inhibition only when administered 1 day before the injury. In contrast, V1233 resulted in a significant inhibition also when administered 7 days or 14 days prior to the injury.

Figure 5C:
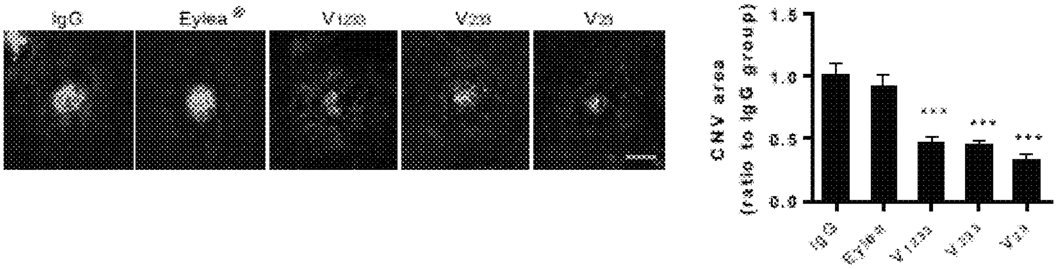
Figure 5D:
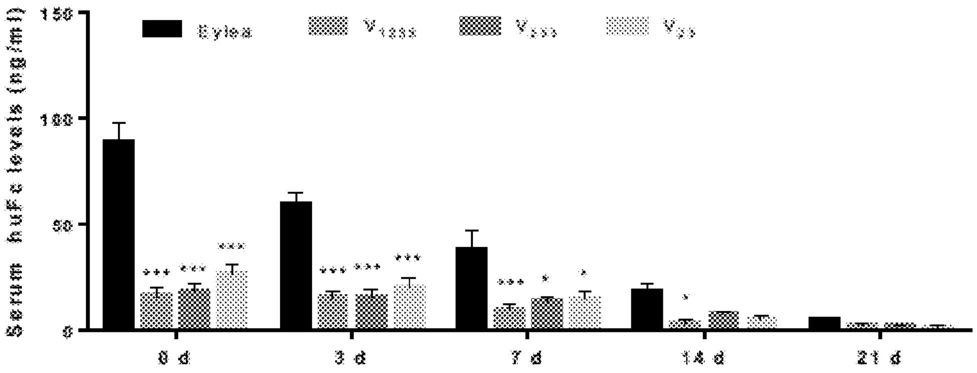

In a subsequent study, equimolar amounts of EYLEA, V23, V1233 and V233, (4.8 μg of EYLEA and V23, 6.3 μg of V233 and 7.2 μg of V1233) were administered 14 days prior to the injury. FIG. 5C shows that, at the dose tested, EYLEA had very little effect on CNV. In contrast, V23, V1233 and V233 resulted in a significant CNV inhibition. A prediction of the hypothesis is that inhibitors with strong heparin-binding characteristics will have lower systemic exposure compared to EYLEA. Both eyes were injected intravitreally with equimolar amounts of EYLEA, V23, V233 or V1233 and human Fc serum levels were measured at different time points up to 21 days after intravitreal administration, as shown in FIG. 5D. EYLEA administration resulted in the highest serum levels throughout the experiment. V23, which has a single heparin binding domain, resulted in lower serum levels than EYLEA, but trended higher than V1233 or V233.

Figures 6A, 6B, 6C:
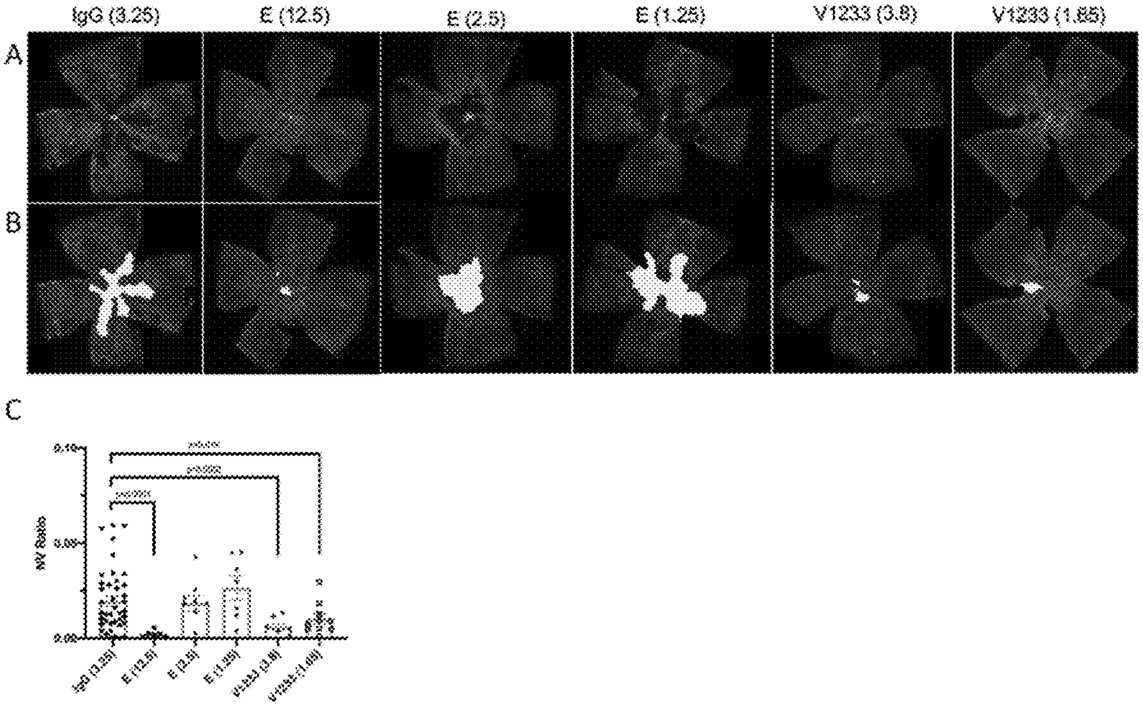
FIGS. 6A-6C show intravitreal injections of V1233 inhibit neovascularization in the OIR model.

Finally, we compared multiple doses of V1233 and EYLEA in the OIR model. In agreement with the findings in the CNV model, V1233 was more potent than EYLEA at inhibiting neovascularization FIG. 6.

FIG. 7 shows inhibitory effects of fusion protein on BCEC proliferation stimulated by VEGF165 or VEGF121. Results are expressed as % of inhibition of VEGF-stimulated proliferation relative to control. Cell numbers were determined by relative fluorescence unit (RFU) 530/590 (Excitation/Emission), average of triplicates.

FIG. 8 shows inhibitory effects of recombinant VEGF receptor Fc-fusion proteins on HUVEC proliferation. V123, V1233, V233, V23 or EYLEA (10-2000 ng/ml) was added along with VEGFI65 (10 ng/ml) for 3 days, and cell viability was determined. Results are expressed as % of inhibition of VEGF-stimulated proliferation relative to control. Cell numbers were determined by relative fluorescence unit (RFU) 530/590 (Excitation/Emission), average of triplicates. Statistical analysis was performed by 2-Way ANOVA in GraphPad Prism software. Statistical significance *$p<0.001$, **$p<0.0001$ was calculated by comparing with VEGF alone.

FIG. 9 shows crystal structure of VEGF/VEGFR2 complex (3V2A) was superimposed on the crystal structure of the VEGF/VEGFR1 complex (5T89). VEGFR1 residues that can potentially interact with VEGF and that differ between VEGFR1 and VEGFR2 are labeled. Yellow and blue greyscales: VEGF. Green greyscale: VEGFR1 D2. White: VEGFR1 D3. Analysis points to a more extensive interaction between VEGF and VEGFR1 D3 compared to VEGFR2 D3.

Figure 10:
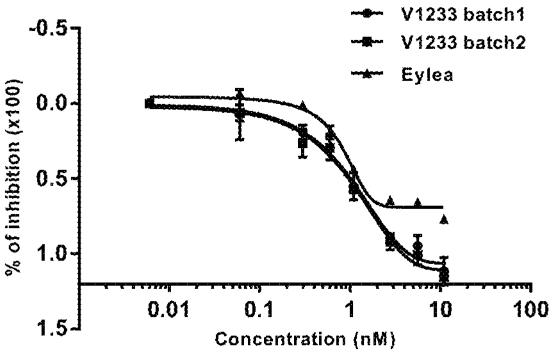
FIG. 10 shows effects of V1233 on bovine endothelial cell proliferation. Bovine choroidal microvascular endothelial cells (BCECs, VEC Technologies) were seeded in 96-well plates in low glucose DMEM supplemented with 10% bovine calf serum and incubated with serial dilutions of V1233 (batch1 and batch2) and EYLEA (Regeneron Pharmaceuticals) in the presence of 10 ng/ml of hVEGF165 (R&D system). After 5 or 6 days, cells were incubated with Alamar Blue for 4 h. Fluorescence was measured at 530 nm excitation wavelength and 590 nm emission wavelength.
Figure 11:
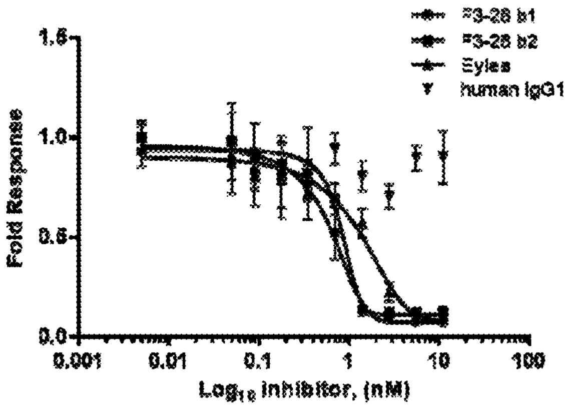
FIG. 11 shows inhibition of VEGF-induced VEGFR2 activation in Promega VEGF. The Promega VEGF Bioassay (GA2001, Promega) was used to measure the ability of V1233, to inhibit stimulation induced by VEGF165 in KDR/NFAT-RE HEK293 Cells were incubated with serial dilutions of V1233 (batch1 and batch2), EYLEA and Human IgG1 (BE0297, BioXcell) in the presence of 20 ng/ml of hVEGF165. After a 6-hour incubation, Bio-Glo80 Reagent was added, and luminescence was quantified using SpectraMax M5 microplate reader. Data were fitted to a 4PLx®curve using GraphPad Prism software.

The activity of purified CHO-expressed V1233 was tested in two independent bioassays: BCEC proliferation (FIG. 10) and the Promega VEGF Bioassays (FIG. 11). Both assays show that two independent batches of purified V1233 inhibit VEGF-stimulated growth or receptor activation with similar (if not greater) potency as EYLEA.

Figure 12:
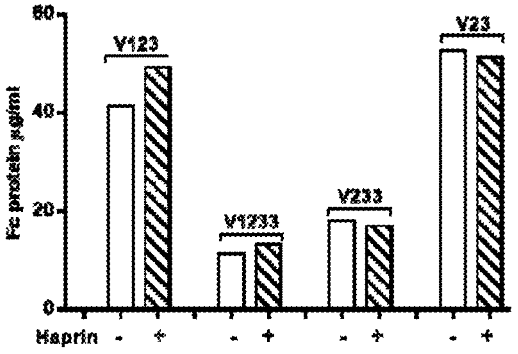
FIG. 12 shows effects of heparin on VEGFR1 constructs concentrations in CHO cells culture media. Split pool cells (V123, V1233, V233 and V23) into CD FortiCHO media with or without 100 μg/ml heparin (#H3149, Sigma) and incubate at 37° C. with 5% CO2 with humidified atmosphere and 125 rpm for 96 hours. The culture media were collected and the expression of VEGFR1 ECDs was evaluated by ELISA.
Figure 13:
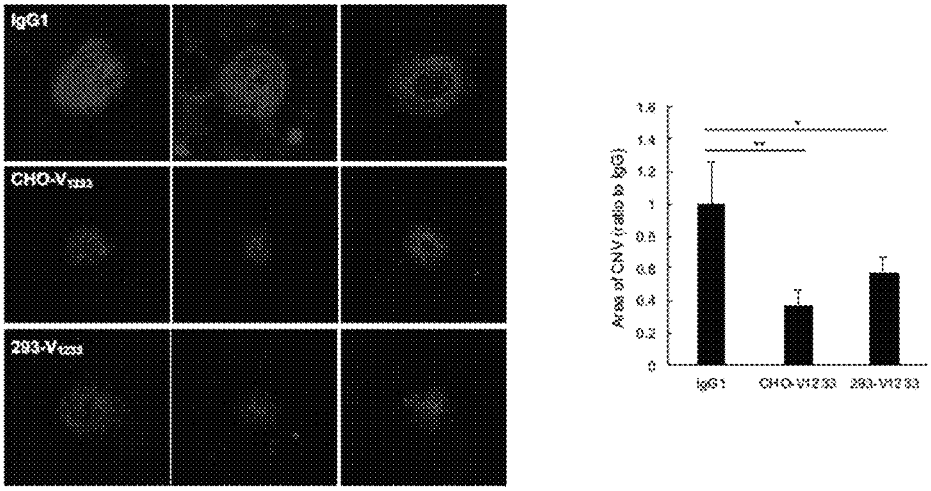
FIG. 13 shows CHO-expressed V1233 is fully active in the mouse CNV model. 6-8 week male C57/B16 mice were used (n=6). After laser induction, ~5 μg of CHO cells-derived and 293 cells-derived V1233 were injected intravitreally (1 μl) in each eye. 10 days later, choroid-sclera complex was harvested and fixed. Neovascular area was indicated by CD31 immunofluorescent whole mount staining. Figure shows three representative neovascular areas in each group.

It was also determined that, in contrast to 293 cells (Expi-293 system), in CHO cells expression of the constructs is not dependent on the addition of heparin to the medium (FIG. 12), a considerable advantage. In addition, we determined that CHO-derived V1233 is fully active in the mouse CNV model and is no less potent than 293 expressed V1233 (FIG. 13).

Discussion

Interaction of D3 with the HPSG has been long considered a limitation of VEGFR1-based anti-VEGF strategies due to sequestration in various tissues, resulting in reduced systemic half-life. To overcome such issue, Holash et al. replaced VEGFR1 D3 with VEGFR2 D3[21]. To the same aim, Lee et al. more recently introduced a glycosylation site in VEGFR1 D3, effectively neutralizing positive charges and thus eliminating D3-mediated HSPG binding[48]. In both cases, systemic half-life was increased relative to the original VEGFR1 construct[21 48].

The present study designed a series of VEGFR-1 Fc fusion constructs having differential abilities to interact with HSPGs. The premise was that heparin-binding, mediated by VEGFR1 D3 (or other Ig-like D such as D4[49]), while a disadvantage for systemic treatment, might confer unique advantages on a VEGF inhibitor to be used for intravitreal administration, since a) it should anchor the inhibitors to HPSGs or other anionic molecules in the vitreous or other structure in the eye, thus increasing its half-life; b) such inhibitor does not need to be uniformly distributed or to deeply penetrate into the eye structures in order to effectively bind and block VEGF. A variety of studies have shown that VEGF can diffuse to a considerable distance from its production site in response to biochemical gradients determined by HPSG or receptor distributions in the vasculature or other sites[50 8 9]. For example, although VEGF is produced by tumor cells even at a significant distance from the vasculature, it diffuses and accumulates in the blood vessels by virtue of its high affinity for the VEGF receptors,[51-53]. Therefore, vitreous-bound VEGFR1 variants are expected to generate strong gradients, capable of attracting and neutralizing VEGF.

Given the challenges in obtaining accurate affinity measurements using sensor platforms such as SPR with very tight binders (Kd<100 pm)[54], the conflicting data regarding the affinity of aflibercept versus other VEGF inhibitors[21 55] and the poor correlation between binding affinity and therapeutic potency/efficacy among neutralizing antibodies to VEGF and other targets[56 57], this study chose to focus on biological $IC_{50}$ data, being more physiologically relevant. As illustrated in FIG. 4, the recombinant proteins had inhibitory effects, with $IC_{50}$ values in the range of ~1 nM, except V124 and V24, which were significantly less potent.

These proteins bind to bovine vitreous. The strongest binders were, V1233, V1234, followed by V123. V23 had significant but lower vitreous binding. Control IgG, EYLEA, or AVASTIN had instead minimal binding.

An unexpected finding of our study was the greater potency of some of the constructs: V123, V23, V1233 and V233. Administering 2.5 μg of these constructs one day before the injury matched or even exceeded the level of inhibition achieved with 25 μg of EYLEA. The finding that V1233, but not EYLEA, has significant effect in preventing CNV when administered 7 days or 14 days before the injury, documents the durability of the effects and the therapeutic value.

Also, it was found that intravitreal injection of these heparin-binding proteins results in much lower systemic levels than EYLEA. This property might be particularly useful, for example, for the treatment of ROP, since it has been reported that treatment with anti-VEGF agents with significant systemic exposure may have detrimental neurodevelopmental effects[58 59].

Interestingly, none of the constructs containing D4 (V1234, V234, V124, V24) resulted in marked inhibition in vivo (at least at the dose tested), in spite of the fact that these molecules (with the exception of $V_{2-4}$) demonstrated an ability to inhibit VEGF-stimulated mitogenesis in vitro. However, all of these constructs demonstrated a propensity to form oligomers or aggregates, as assessed by SDS/PAGE under non-reducing conditions and size exclusion chromatography (data not shown). Although earlier work[60] identified D4 (together with D7) as a requirement for VEGFR-1 dimerization, such effect has been known to be ligand-dependent. Crystal structure studies revealed a loop in D4 responsible for such homotypic interactions[39]. It is conceivable that high concentrations and/or the forced dimerization imposed by the Fc construct may result in ligand-independent interactions, resulting in aggregation. In any event, aggregates are not desirable pharmaceuticals given the possibility of inflammation and immunogenicity[61, 62]. Importantly, the lack of significant efficacy of our D4-including proteins argues against the possibility that a contaminant may be responsible for the observed efficacy, since all proteins were purified by the same methodology and have strong heparin-binding properties.

In conclusion, aflibercept was designed to eliminate the heparin-binding heparin domain in order to improve systemic half-life for oncological indications. The constructs described in the present study are instead designed to promote binding and retention in the vitreous to ensure more sustained and therapeutically relevant interactions.

In experiments in which CHO cells were employed as an expression system, the requirement for adding heparin to the media of transfected cells was greatly diminished, such that adding heparin to the media resulted in very small increases in the recombinant protein concentrations. This is likely explained by differences in HSPG composition/concentrations between 293 and CHO cells.

Methods

For construction of VEGFR-Fc expression plasmids, the nucleic acid fragments encoding the signal peptide and a combination of extracellular Ig-like domains one to four of VEGRF127 (Gene ID: 2321) were synthesized by GenScript USA Inc. The following constructs were done: V123, D1, D2 and D3; V23, D2 and D3; V1233, D1, D2, D3 and D3; V233 D2, D3 and D3; V1234, D1, D2, D3 and D4; V234, D2, D3 and D4; V124, D1, D2 and D4; V24, D2 and D4. The synthesized fragments were inserted into pFUSE-hIgGl-Fc1 vector (InvivoGen, #pfuse-hgifc1) at EcoRI and BglII sites, generating the plasmids containing the various VEGFR1 ECDs. Then, using PrimeSTAR Mutagenesis Basal Kit (Takara, R046A), the interval amino acids R and S (BglII site) between the ECDs and the Fc fragment were removed, generating the plasmids expressing the fusion proteins of VEGFR1 ECDs with a 227-amino acid human IgG1-Fc.

Transfection and Conditioned Media Preparation

The Expi293 expression system (Life technologies, A14524) was used to generate the conditioned media for purification, according to the manufacturer's instructions. In brief, Expi293F™ Cells (ThermoFisher) were suspension-cultured in Expi293™ expression medium at 37° C. in a humidified atmosphere with 8% CO2. When the cell density reached to 2.5 million/ml, plasmids DNA and Expi-Fectamine™ 293 reagent was mixed, incubated 5 min and added to the cells. The final concentration of the DNA and transfected reagent was 1 μg and 2.7 μl per milliliter respectively. Five hours after transfection, 100 μg/ml Heparin (Sigma, H3149) and protease inhibitor cocktail, 1:400 (Sigma, P1860), were added to the cells. 16 hours after transfection, enhancer reagents 1 and 2 were added. Ninety-six hours after transfection, conditioned media were harvested. Aliquots were tested for Fc fusion proteins concentrations using a human Fc ELISA Kit (Syd Labs, EK000095-HUFC-2) according to the manufacturer's instructions. Protease inhibitors were added (1:500) to the bulk, which was stored at −80° C. until further use.

Purification of Recombinant Proteins

Pyrogen-free reagents were employed. Prior to use, columns and equipment (Akta Explorer System) were sanitized by exposure to 0.5 N NaOH. Conditioned media from transfected cells were adjusted to PBS, 0.01% polysorbate (PS) 20. PS20 was added to buffers at all steps. After centrifugation at 20,000×g for 30 minutes, supernatants were subjected to protein A (PA) affinity chromatography using a Hi-Trap MabSelect SuRe (5 ml, GE Healthcare). After loading, the column was washed with 20 mM diethanolamine, pH 9.2, 1.2 M NaCl, prior to elution with 0.1 M citric acid, pH 3.0, which was immediately neutralized. The PA elution pool was then diluted in 20 mM diethanolamine, pH 9.2, and applied to Hi-Trap Q (GE Healthcare) anion-exchange column. The bound material was eluted with a gradient of NaCl. The flow-through, which contained the purified recombinant protein, was immediately adjusted to 20 mM Tris, pH 6.8, and then concentrated through binding to heparin-sepharose (Hi-Trap™-HS). After a wash with 0.2-0.45 M NaCl (depending on the construct), the recombinant VEGFR1 fusion protein was eluted with 1 M NaCl. The final polishing step consisted of size-exclusion chromatography (SEC). Finally, the proteins were buffer-exchanged by dialysis into 10 mM Tris, pH 6.8, 10 mM histidine, 5-7% threalose, 40 mM NaCl, 0.01% PS20. The goal is obtaining a close to iso-osmolar formulation (~300 mOsm). To determine endotoxin levels, ToxinSensor Chromogenic LAL Endotoxin Assay Kit (GenScript, L00350) was used according to the manufacturer's protocol.

Cell Proliferation Assays

Endothelial cell proliferation assays were performed essentially as previously described[63 64]. Primary bovine choroidal endothelial cells (BCEC) (passage <10) (VEC Technologies Rensselaer, N.Y., Cat #BCME-4) were trypsinized, re-suspended and seeded in 96-well plates (no coating) in low glucose DMEM supplemented with 10% bovine calf serum, 2 mM glutamine, and antibiotics, at a density of 1000 cells per well in 200 μl volume. $rhVEGF_{165}$ (R& D Systems, Cat #293-VE-010) or $rhVEGF_{121}$ (R& D Systems Cat. #4644-VS010) was added at the concentration of 10 ng/ml. Aflibercept (EYLEA) was purchased from a pharmacy. The inhibitors were added to cell at various concentrations, as indicated in the figures., before adding the ligands. After 5 or 6 days, cells were incubated with Alamar Blue for 4 hr. Fluorescence was measured at 530 nm excitation wavelength and 590 nm emission wavelength.

Primary human umbilical vein endothelial cells (HUVEC), from pooled donors (Lonza Cat #C2519A), passage 5-9, were cultured on 0.1% gelatin coated plates in EGM-2 endothelial cell growth media (Lonza). Cells were maintained at 37° C. in a humidified atmosphere with 5% CO2. To measure cell proliferation, 1800 HUVECs suspended in 200 ul of endothelial basal growth media EBM-2 (Lonza) containing 0.5% PBS, were seeded in 96-well plate. Four hours later recombinant Fc-fusion proteins and EYLEA at concentrations of 10, 20, 50, 250, 500, 1000 and 2000 ng/ml were added to cells along with 10 ng/ml of VEGF165. Cells were cultured for 3 days, and cell viability was determined by alamarBlue Cell viability reagent (Thermo Fisher Scientific), following the manufacturer's instruction.

In Vitro Binding to Bovine Vitreous

Bovine vitreous samples (InVision BioResource, Seattle, Wash.) were thawed at 4° C. and then diluted 1:1 with PBS, filtered through 0.22 pm filter, aliquoted and stored at −80° C. Total protein concentrations were measured by the Pierce BCA protein assay. Costar 96-well EIA/RIA stripwells were coated with vitreous (1 pg/well) for 4 hr at RT, followed by one wash with PBS-0.1% Tween 20 (PBS-T). To each well, 0.08 to 10 nM chimeric VEGF receptor protein was added in a 50 pl volume and incubated overnight at 4° C. Plates were be then washed with PBS-T, and incubated with AP-conjugated goat anti-human Fc (1:2000, Invitrogen, #A18832) for 1 hr at RT. Plates were washed with PBS-T before 1 step PNPP substrate (Thermo Scientific, Rockford, Ill., #37621) for 15-30 min at RT. Absorbance will be measured at 405 nm. S Laser-Induced Choroidal Neovascularization (CNV)

Male C57BL/6J mice (6-8 week) were anesthetized with ketamine/Xylazine cocktail before laser treatment. CNV lesions were induced by laser photocoagulation using a diode laser (IRIDEX, Oculight GL) and a slit lamp (Zeiss) with a spot size of 50 um, power of 180 mW and exposure duration of 100 ms.[47, 65] Four laser burns were typically induced at 3, 6, 9 and 12 o'clock position around the optic disc in each eye. Different constructs or IgG isotype control were injected intravitreally, at the dose of 2.5 μg per eye, in a 1 pl volume. EYLEA was used as a positive control at 2.5 or 25 μg. One day after injection, laser treatment was conducted and eyes were enucleated and fixed in 4% paraformaldehyde (PFA) for 15 min, 7 days after laser treatment. In a separate set of studies, selected constructs were injected once 1 day, 7 days or 14 days prior to laser treatment. Choroid-sclera complexes and retinas were separated and anti-CD31 immunofluorescence (IF) was performed to evidence the vasculature by whole mount staining of both retina and choroidal tissues. For CD31 IF, rat anti-mouse antibody BD 550274 was diluted 1:100 and incubated overnight at 4° C. After 4-hour incubation with a secondary anti-rat antibody (Life Technologies A11006), whole mounts were imaged at 488 nm. Quantification of neovascularization in lesion area and vascular density in retina was carried out by Image J. P values were assessed by Student's t test (significant change, $p<0.05$).

Oxygen-Induced Retinopathy Model

The Oxygen Induced Retinopathy (OIR) mouse model is a well-established method that has proven useful in delineating the molecular changes in ischemic vascular eye disease[66 67] Using an enclosed chamber, neonatal mice are exposed to 75% oxygen from postnatal day 7 (P7) until P12, and then returned to 21% oxygen (room air). This exposure to hyperoxia causes vessel regression in the central retina and the cessation of normal radial vessel growth, mimicking the vaso-obliterative phase of ischemic vasculopathies. Upon return to room air, the avascular areas of retina become hypoxic[68 69]. This hypoxia induces the expression of angiogenic factors, especially VEGF70, resulting in the growth of aberrant retinal neovascularization at the junctions of vascular and avascular retina. To test the effects of inhibitors, intravitreal injections will be performed prior to exposure to hyperoxia in an effort to test inhibition of the neovascular phase. Wild-type C57BL/6j mice at P7 will be anesthetized using isoflurane flowing through a rodent face-mask. The eyelids will be opened using a Vannas microdissection scissors and pulled back to expose the eye. Next, 0.5 pl of solution will be injected using pulled glass micropipettes attached to a picospritzer III (Parker Hannifin) into the vitreous cavity. The needle will be left in the eye for 30 seconds after injection and withdrawn slowly to minimize leakage. This procedure will be repeated in the fellow eye with injection of equimolar human IgG1 as control (Bio X Cell, West Labanon, N.H.). EYLEA, various constructs will be tested versus control IgG1 at various doses. The eyelids were covered with antibiotic ointment. Litters will then be placed in a 75% hyperoxic chamber from P7-P12 to generate the OIR phenotype. At P17, the peak time for neovascularization, the animals will be sacrificed, and the eyes will be enucleated, dissected, and the vessels will be stained with BSL-FITC. The retinas were flat-mounted and imaged by confocal microscopy. The extent of neovascularization was quantified by measuring the volume of pre-retinal vascular buds[67 70-72]. Vaso-obliteration and neovascularization were analyzed using automated software, as described[73].

CHO Cell Studies

Plasmid Construction and Expression

Nucleic acid fragments encoding extracellular Ig-like domains (ECDs) one to three with the signal peptide of VEGFR1 (Gene ID: 2321) and a human IgG1 Fc domains (Gene ID: 3500) were synthesized by GenScript USA Inc. The fragments were inserted into pD2535nt-HDP Dual EF1a-promoter vector (ATUM) at XbaI and ECoR1 sites, generating the plasmids expressing the fusion proteins of VEGFR1 ECDs with a 227-amino acid human IgG1-Fc. The VEGFR1 ECDs constructs are as follows: V123 contains ECD1, 2 and 3; V1233 contains ECD1, 2, 3 and 3; V233 contains ECD 2, 3 and 3 and V23 contains ECD 2 and 3. The authenticity of all constructs was verified by sequence analysis.

CHO K1 Glutamine Synthetase (GS) null cells (HD-BIOP3, Horizon) were used for stable expression and transfections were carried out using Neon™ Transfection System (#MPK10096, ThermoFisher). Briefly, linearized construct DNA was transfected by electroporation into HD-BIOP3 cells according to the protocol provided by Horizon Discovery, then the cells were cultured in CD FortiCHO media (#A1148301, ThermoFisher) containing 4 mM L-glutamine (#25030081, ThermoFisher) at 37° C. with humidified atmosphere of 5% $CO_2$ for 48 h. After the 2 day recovery, the media were changed with selection media, CD FortiCHO containing 50 μM MSX (#76078, Sigma). For up to 20 days culture, four pools of VEGFR1 ECDs were selected and banked. The expression of VEGFR1 fusion protein in the culture media was evaluated by human Fc ELISA Kit (EK000095-HUFC-2, Syd Lab Inc.) and western blotting with anti-human IgG1 Fc antibody (A-10648, Invitrogen). The expression levels for the four pools were from 1.9 to 13 μg per 1 million cells (7.1 for V123, 1.98 for V1233, 4.7 for V233 and 12.7 for V23 in the average).

For single cell clone screening, the pool cells were diluted and selected according to the protocol (Horizon). After about 60 days' culture, total 39 clones, 8 for V123, 11 for V1233, 9 for V233 and 11 for V23, were selected and stocked. The expression of VEGFR1 fusion protein in the culture media for each clone was evaluated by ELISA and western blot. The expression level is from 3.0 to 18.3 μg per 1 million cells (12 for V123, 3.7 for V1233, 6.5 for V233 and 13 for V23 in the average).

For large scale of culture media preparation, the cells (single cell clone) were seeded at the density of $0.5\times10^6$/ml into the spinner flask and cultured in the media of CD FortiCHO supplemented with 1:1000 Anti-clumping agent (#0010057AE, ThermoFisher) and 1:200 Protease Inhibitor Cocktail (p1860, Sigma) at 37° C. with 5% CO2 with humidified atmosphere and 125 rpm (Orbital shaker with a 25 mm orbit). Cell viability and density were monitored each day, and the culture media were collected after 5-7 days' incubation (the cell density is 7.0-10×106/ml, viability is >90%). Clones, V1233-26, V233-52/67 and V23-5 were used for large culture media preparation. The expression of VEGFR1 fusion proteins in the media was verified by ELISA and western blot and media were stored at −80° C. for further purification. The expression level was from 20 to 115 μg/ml (23 μg/ml for V1233, 47 μg/ml for V233 and 105 μg/ml for V23 in the average).

Purification

Horizon Discovery (HD)-BIOP3 CHO cells expressing higher levels of V1233 protein (20-30 ug/ml) clones 14, 26, 44 and 46 were subjected to purification. All four clones yielded similar end product, thus for subsequent purification we used clone 26. Condition media equivalent to roughly 10 mg from V1233-26 was performed as follows: Conditioned media thawed at 37° C. was adjusted to 5% PBS and 0.01% (v/v) Tween20, and was centrifuged at 20,000 g for 30 min at 4° C. The clarified extract was applied to a Protein A column (HiTrap™ MabSelect™Sure 5 ml) (GE Healthcare) equilibrated in 1×PBS and 0.01% Tween20. The column was washed with high pH, high salt buffer (5 CV: 20 mM ethanolamine, pH 9.2, 1.2 M Nacl, 0.01% Tween 20), and the bound proteins were eluted by 0.1M citric acid, pH 3.0, and were neutralized immediately by adding ⅕ the volume of 1M Tris, pH 9.5. Fractions containing Flt1 protein were pooled, diluted 10× in 20 mM ethanolamine, pH 9.2, 0.01% Tween20, and applied to HiTrap™Q HP 5 ml (GE Healthcare) anion exchange column. Flt1 protein present in Flow through was adjusted to pH 6.8 by adding 10% v/v 0.5M Tris, pH 6.8, and was applied to HiTrap™Heparin HP 1 ml column equilibrated in 20 mM Tris, pH 6.8, 0.01% Tween20. The column was washed with 0.45M NaCl in buffer, followed by final elution in 1M NaCl. Fractions positive for Flt1 were pooled, and was subjected to gel filtration chromatography in HiLoad Superdex 16×600 column (GE Healthcare) in 10 mM Tris, pH 7.2, 0.4M NaCl, 0.01% Tween20. Fractions excluding the high molecular weight aggregates were pooled, concentrated after binding to HiTrap™Heparin HP 1 ml column followed by 1M NaCl elution as mentioned before.

The eluted proteins were dialyzed using Float-A-Lyzer®G2 dialysis Device, MWCO 100 kD or 50 kD (Spectrum Laboratories), and concentrated by using Amicon centrifugal filters UltraCel 50k.

For large scale purification (condition media equivalent to 50 mg protein), the method was modified as follows; Protein A chromatography was done using HiTrapPrismA 5 ml column with two wash steps using buffer 1 (50 mM Tris, pH 8.5, 1.2M NaCl, 0.5M Arginine, 0.01% Tween20) and buffer 2 (25 mM sodium phosphate, pH 6.5, 200 mM NaCl, 0.01% Tween20) before final elution in 0.1M citric acid. HiTrapQ was performed using 20 mM Tris, pH 8.5, and slightly higher salt (0.55M) was used to wash HiTrap heparin column. Gel filtration step was performed in a wider column (HiLoad 26×600) in buffer 10 mM Histidine, pH 6.0, 80 mM NaCl, 0.01% Tween20. Instead of dialysis, PD10 column was used for buffer exchange, and the final protein was stored in 10 mM sodium acetate, pH 5.0, 7% trehalose and 0.01% Tween20.

Chromatography was carried out in FPLC system AKTA Avant (GE Healthcare). Column and the instrument were sanitized (cleaning in place) by 0.5N NaOH before each run. Purity of the protein was determined by SDS-PAGE and silver staining after each step. The quality of final protein preparation was determined by analytical gel filtration.

Total protein estimation was done by Protein assay dye reagent (Bio-Rad), and by Fc ELISA kit for human Fc proteins and human IgGs (Syd Labs). Overall protein recovery was roughly 10%, and the final protein achieved the level of endotoxin around 0.004 EU/mg, and HCP 150 ng/mg.

REFERENCES

[1] Folkman J, Klagsbrun M: Angiogenic factors. Science 1987, 235:442-7.

[2] Klagsbrun M, D'Amore P A: Regulators of angiogenesis. Annu Rev Physiol 1991, 53:217-39.

[3] Ferrara N, Adamis A P: Ten years of anti-vascular endothelial growth factor therapy. Nat Rev Drug Discov 2016, 15:385-403.

[4] Ferrara N, Gerber H P, LeCouter J: The biology of VEGF and its receptors. Nature Med 2003, 9:669-76.

[5] Houck K A, Ferrara N, Winer J, Cachianes G, Li B, Leung D W: The vascular endothelial growth factor family: identification of a fourth molecular species and characterization of alternative splicing of RNA. Molecular Endocrinology 1991, 5:1806-14.

[6] Tischer E, Mitchell R, Hartman T, Silva M, Gospodarowicz D, Fiddes J C, Abraham J A: The human gene for vascular endothelial growth factor. Multiple protein forms are encoded through alternative exon splicing. Journal of Biological Chemistry 1991, 266:11947-54.

[7] Park J E, Keller G-A, Ferrara N: The vascular endothelial growth factor isoforms (VEGF): Differential deposition into the subepithelial extracellular matrix and bioactivity of extracellular matrix-bound VEGF. Molecular Biology of the Cell 1993, 4:1317-26.

[8] Ruhrberg C, Gerhardt H, Golding M, Watson R, Ioannidou S, Fujisawa H, Betsholtz C, Shima D T: Spatially restricted patterning cues provided by heparin-binding VEGF-A control blood vessel branching morphogenesis. Genes Dev 2002, 16:2684-98.

[9] Ferrara N: Binding to the extracellular matrix and proteolytic processing: two key mechanisms regulating vascular endothelial growth factor action. Mol Biol Cell 2010 21:687-90.

[10] de Vries C, Escobedo J A, Ueno H, Houck K, Ferrara N, Williams L T: The fms-like tyrosine kinase, a receptor for vascular endothelial growth factor. Science 1992, 255:989-91.

[11] Terman B I, Dougher Vermazen M, Carrion M E, Dimitrov D, Armellino D C, Gospodarowicz D, Bohlen P: Identification of the KDR tyrosine kinase as a receptor for vascular endothelial cell growth factor. Biochem-Biophys-Res-Commun 1992, 187:1579-86 issn: 0006-291x.

[12] Joukov V, Pajusola K, Kaipainen A, Chilov D, Lahtinen I, Kukk E, Saksela O, Kalkkinen N, Alitalo K: A novel vascular endothelial growth factor, VEGF-C, is a ligand for the Flt4 (VEGFR-3) and KDR (VEGFR-2) receptor tyrosine kinases. EMBO-J 1996, 15:1751 issn: 0261-4189.

[13] Alitalo K, Tammela T, Petrova T V: Lymphangiogenesis in development and human disease. Nature 2005, 438: 946-53.

[14] Olsson A K, Dimberg A, Kreuger J, Claesson-Welsh L: VEGF receptor signalling—in control of vascular function. Nat Rev Mol Cell Biol 2006, 7:359-71.

[15] Ferrara N: VEGF and the quest for tumour angiogenesis factors. Nat Rev Cancer 2002, 2:795-803.

[16] Miller J W, Le Couter J, Strauss E C, Ferrara N: Vascular endothelial growth factor a in intraocular vascular disease. Ophthalmology 2013, 120:106-14.

[17] Apte R S, Chen D S, Ferrara N: VEGF in Signaling and Disease: Beyond Discovery and Development. Cell 2019, 176:1248-64.

[18] Presta L G, Chen H, O'Connor S J, Chisholm V, Meng Y G, Krummen L, Winkler M, Ferrara N: Humanization of an Anti-Vascular Endothelial Growth Factor Monoclonal Antibody for the Therapy of Solid Tumors and Other Disorders. Cancer Res 1997, 57:4593-9.

[19] Chen Y, Wiesmann C, Fuh G, Li B, Christinger H W, McKay P, de Vos A M, Lowman H B: Selection and analysis of an optimized anti-VEGF antibody: crystal structure of an affinity-matured Fab in complex with antigen. Journal of Molecular Biology 1999, 293:865-81.

[20] Chamow S M, Ryll T, Lowman H B, Farson D: Therapeutic Fc-Fusion Proteins. Wiley Blackwell, 2014.

[21] Holash J, Davis S, Papadopoulos N, Croll S D, Ho L, Russell M, Boland P, Leidich R, Hylton D, Burova E, Ioffe E, Huang T, Radziejewski C, Bailey K, Fandl J P, Daly T, Wiegand S J, Yancopoulos G D, Rudge J S: VEGF-Trap: a VEGF blocker with potent antitumor effects. Proc Natl Acad Sci USA 2002, 99:11393-8.

[22] Comparison of Age-related Macular Degeneration Treatments Trials Research G, Maguire M G, Martin D F, Ying G S, Jaffe G J, Daniel E, Grunwald J E, Toth C A, Ferris F L, 3rd, Fine S L: Five-Year Outcomes with Anti-Vascular Endothelial Growth Factor Treatment of Neovascular Age-Related Macular Degeneration: The Comparison of Age-Related Macular Degeneration Treatments Trials. Ophthalmology 2016, 123:1751-61.

[23] Holz F G, Tadayoni R, Beatty S, Berger A, Cereda M G, Cortez R, Hoyng C B, Hykin P, Staurenghi G, Heldner S, Bogumil T, Heah T, Sivaprasad S: Multi-country real-life experience of anti-vascular endothelial growth factor therapy for wet age-related macular degeneration. Br J Ophthalmol 2015, 99:220-6.

[24] Regula J T, Lundh von Leithner P, Foxton R, Barathi V A, Cheung C M, Bo Tun S B, Wey Y S, Iwata D, Dostalek M, Moelleken J, Stubenrauch K G, Nogoceke E, Widmer G, Strassburger P, Koss M J, Klein C, Shima D T, Hartmann G: Targeting key angiogenic pathways with a bispecific CrossMAb optimized for neovascular eye diseases. EMBO Mol Med 2016, 8:1265-88.

[25] Rodrigues G A, Mason M, Christie L A, Hansen C, Hernandez L M, Burke J, Luhrs K A, Hohman T C: Functional Characterization of Abicipar-Pegol, an Anti-VEGF DARPin Therapeutic That Potently Inhibits Angiogenesis and Vascular Permeability. Invest Ophthalmol Vis Sci 2018, 59:5836-46.

[26] Vorum H, Olesen T K, Zinck J, Hedegaard M: Real world evidence of use of anti-VEGF therapy in Denmark. Curr Med Res Opin 2016:1-32.

[27] Davis-Smyth T, Chen H, Park J, Presta L G, Ferrara N: The second immunoglobulin-like domain of the VEGF tyrosine kinase receptor Flt-1 determines ligand binding and may initiate a signal transduction cascade. EMBO Journal 1996, 15:4919-27.

[28] Wiesmann C, Fuh G, Christinger H W, Eigenbrot C, Wells J A, de Vos A M: Crystal structure at 1.7 A resolution of VEGF in complex with domain 2 of the Flt-1 receptor. Cell 1997, 91:695-704.

[29] Christinger H W, Fuh G, de Vos A M, Wiesmann C: The Crystal Structure of Placental Growth Factor in Complex with Domain 2 of Vascular Endothelial Growth Factor Receptor-1. J Biol Chem 2004, 279:10382-8.

[30] Markovic-Mueller S, Stuttfeld E, Asthana M, Weinert T, Bliven S, Goldie K N, Kisko K, Capitani G, Ballmer-Hofer K: Structure of the Full-length VEGFR-1 Extracellular Domain in Complex with VEGF-A. Structure 2017, 25:341-52.

[31] Ferrara N, Chen H, Davis-Smyth T, Gerber H-P, Nguyen T-N, Peers D, Chisholm V, Hillan K J, Schwall R H: Vascular endothelial growth factor is essential for corpus luteum angiogenesis. Nature Medicine 1998, 4:336-40.

[32] Gerber H P, Vu T H, Ryan A M, Kowalski J, Werb Z, Ferrara N: VEGF couples hypertrophic cartilage remodeling, ossification and angiogenesis during endochondral bone formation. Nature Med 1999, 5:623-8.

[33] Gerber H P, Hillan K J, Ryan A M, Kowalski J, Keller G-A, Rangell L, Wright B D, Radtke F, Aguet M, Ferrara N: VEGF is required for growth and survival in neonatal mice. Development 1999, 126:1149-59.

[34] Gerber H P, Kowalski J, Sherman D, Eberhard D A, Ferrara N: Complete inhibition of rhabdomyosarcoma xenograft growth and neovascularization requires blockade of both tumor and host vascular endothelial growth factor. Cancer Res 2000, 60:6253-8.

[35] Lissbrant I F, Hammarsten P, Lissbrant E, Ferrara N, Rudolfsson S H, Bergh A: Neutralizing VEGF bioactivity with a soluble chimeric VEGF-receptor protein flt(1-3) IgG inhibits testosterone-stimulated prostate growth in castrated mice. Prostate 2004, 58:57-65.

[36] Zheng M, Deshpande S, Lee S, Ferrara N, Rouse B T: Contribution of vascular endothelial growth factor in the neovascularization process during the pathogenesis of herpetic stromal keratitis. J Virol 2001, 75:9828-35.

[37] Kim E S, Serur A, Huang J, Manley C A, McCrudden K W, Frischer J S, Soffer S Z, Ring L, New T, Zabski S, Rudge J S, Holash J, Yancopoulos G D, Kandel J J, Yamashiro D J: Potent VEGF blockade causes regression of coopted vessels in a model of neuroblastoma. Proc Natl Acad Sci USA 2002, 99:11399-404.

[38] Houck K A, Leung D W, Rowland A M, Winer J, Ferrara N: Dual regulation of vascular endothelial growth factor bioavailability by genetic and proteolytic mechanisms. J-Biol-Chem 1992, 267:26031-7.

[39] Malyala P, Singh M: Endotoxin limits in formulations for preclinical research. J Pharm Sci 2008, 97:2041-4.

[40] Shibuya M: VEGFR and type-V RTK activation and signaling. Cold Spring Harb Perspect Biol 2013, 5:a009092.

[41] Park J E, Chen H H, Winer J, Houck K A, Ferrara N: Placenta growth factor. Potentiation of vascular endothelial growth factor bioactivity, in vitro and in vivo, and high affinity binding to Flt-1 but not to Flk-1/KDR. J-Biol-Chem 1994, 269:25646-54 issn: 0021-9258.

[42] Brozzo M S, Bjelic S, Kisko K, Schleier T, Leppanen V M, Alitalo K, Winkler F K, Ballmer-Hofer K: Thermodynamic and structural description of allosterically regulated VEGFR-2 dimerization. Blood 2012, 119:1781-8.

[43] Kwak N, Okamoto N, Wood J M, Campochiaro P A: VEGF is major stimulator in model of choroidal neovascularization. Invest Ophthalmol Vis Sci 2000, 41:3158-64.

[44] Saishin Y, Takahashi K, Lima e Silva R, Hylton D, Rudge J S, Wiegand S J, Campochiaro P A: VEGF-TRAP (R1R2) suppresses choroidal neovascularization and VEGF-induced breakdown of the blood-retinal barrier. J Cell Physiol 2003, 195:241-8.

[45] Campa C, Kasman I, Ye W, Lee W P, Fuh G, Ferrara N: Effects of an anti-VEGF-A monoclonal antibody on laser-induced choroidal neovascularization in mice: optimizing methods to quantify vascular changes. Invest Ophthalmol Vis Sci 2008, 49:1178-83.

[46] Bogdanovich S, Kim Y, Mizutani T, Yasuma R, Tudisco L, Cicatiello V, Bastos-Carvalho A, Kerur N, Hirano Y, Baffi J Z, Tarallo V, Li S, Yasuma T, Arpitha P, Fowler B J, Wright C B, Apicella I, Greco A, Brunetti A, Ruvo M, Sandomenico A, Nozaki M, Ijima R, Kaneko H, Ogura Y, Terasaki H, Ambati B K, Leusen J H, Langdon W Y, Clark M R, Armour K L, Bruhns P, Verbeek J S, Gelfand B D, De Falco S, Ambati J: Human IgG1 antibodies suppress angiogenesis in a target-independent manner Signal Transduct Target Ther 2016, 1.

[47] Silva R L E, Kanan Y, Mirando A C, Kim J, Shmueli R B, Lorenc V E, Fortmann S D, Sciamanna J, Pandey N B, Green J J, Popel A S, Campochiaro P A: Tyrosine kinase blocking collagen IV-derived peptide suppresses ocular neovascularization and vascular leakage. Sci Transl Med 2017, 9.

[48] Lee J E, Kim C, Yang H, Park I, Oh N, Hua S, Jeong H, An H J, Kim S C, Lee G M, Koh G Y, Kim H M: Novel glycosylated VEGF decoy receptor fusion protein, VEGF-Grab, efficiently suppresses tumor angiogenesis and progression. Mol Cancer Ther 2015, 14:470-9.

[49] Park M, Lee S T: The fourth immunoglobulin-like loop in the extracellular domain of FLT-1, a VEGF receptor, includes a major heparin-binding site. Biochem Biophys Res Commun 1999, 264:730-4.

[50] Gerhardt H, Golding M, Fruttiger M, Ruhrberg C, Lundkvist A, Abramsson A, Jeltsch M, Mitchell C, Alitalo K, Shima D, Betsholtz C: VEGF guides angiogenic sprouting utilizing endothelial tip cell filopodia. J Cell Biol 2003, 161:1163-77.

[51] Dvorak H F, Sioussat T M, Brown L F, Berse B, Nagy J A, Sotrel A, Manseau E J, Van de Water L, Senger D R: Distribution of vascular permeability factor (vascular endothelial growth factor) in tumors: concentration in tumor blood vessels. Journal of Experimental Medicine 1991, 174:1275-8.

[52] Plate K H, Breier G, Weich H A, Risau W: Vascular endothelial growth factor is a potential tumour angiogenesis factor in human gliomas in vivo. Nature 1992, 359:845-8.

[53] Qu H, Nagy J A, Senger D R, Dvorak H F, Dvorak A M: Ultrastructural localization of vascular permeability factor/vascular endothelial growth factor (VPF/VEGF) to the abluminal plasma membrane and vesiculovacuolar organelles of tumor microvascular endothelium. Journal of Histochemistry & Cytochemistry 1995, 43:381-9.

[54] Yang D, Singh A, Wu H, Kroe-Barrett R: Comparison of biosensor platforms in the evaluation of high affinity antibody-antigen binding kinetics. Anal Biochem 2016, 508:78-96.

[55] Yang J, Wang X, Fuh G, Yu L, Wakshull E, Khosraviani M, Day E S, Demeule B, Liu J, Shire S J, Ferrara N, Yadav S: Comparison of binding characteristics and in vitro activities of three inhibitors of vascular endothelial growth factor a. Mol Pharm 2014, 11:3421-30.

[56] Gerber H P, Wu X, Yu L, Weissman C, Liang X H, Lee C V, Fuh G, Olsson C, Damico L, Xie D, Meng Y G, Gutierrez J, Corpuz R, Li B, Hall L, Rangell L, Ferrando R, Lowman H, Peale F, Ferrara N: Mice expressing a humanized form of VEGF-A may provide insights into safety and efficacy of anti-VEGF antibodies. Proc Natl Acad Sci USA 2007, 104:3478-83.

[57] Bachmann M F, Kalinke U, Althage A, Freer G, Burkhart C, Roost H, Aguet M, Hengartner H, Zinkernagel R M: The role of antibody concentration and avidity in antiviral protection. Science 1997, 276:2024-7.

[58] Morin J, Luu T M, Superstein R, Ospina L H, Lefebvre F, Simard M N, Shah V, Shah P S, Kelly E N, Canadian Neonatal N, the Canadian Neonatal Follow-Up Network I: Neurodevelopmental Outcomes Following Bevacizumab Injections for Retinopathy of Prematurity. Pediatrics 2016, 137.

[59] Sankar M J, Sankar J, Chandra P: Anti-vascular endothelial growth factor (VEGF) drugs for treatment of retinopathy of prematurity. Cochrane Database Syst Rev 2018, 1:CD009734.

[60] Barleon B, Totzke F, Herzog C, Blanke S, Kremmer E, Siemeister G, Marme D, Martiny-Baron G: Mapping of the sites for ligand binding and receptor dimerization at the extracellular domain of the vascular endothelial growth factor receptor FLT-1. Journal of Biological Chemistry 1997, 272:10382-8.

[61] Roberts C J: Therapeutic protein aggregation: mechanisms, design, and control. Trends Biotechnol 2014, 32:372-80.

[62] Ratanji K D, Derrick J P, Dearman R J, Kimber F Immunogenicity of therapeutic proteins: influence of aggregation. J Immunotoxicol 2014, 11:99-109.

[63] Yu L, Wu X, Cheng Z, Lee C V, Lecouter J, Campa C, Fuh G, Lowman H, Ferrara N: Interaction between Bevacizumab and Murine VEGF-A: A Reassessment. Invest Ophthalmol Vis Sci 2008, 49:522-7.

[64] Xin H, Thong C, Nudleman E, Ferrara N: Evidence for Pro-angiogenic Functions of VEGF-Ax. Cell 2016, 167:275-84 e6.

[65] Lambert V, Lecomte J, Hansen S, Blacher S, Gonzalez M L, Struman I, Sounni N E, Rozet E, de Tullio P, Foidart J M, Rakic J M, Noel A: Laser-induced choroidal neovascularization model to study age-related macular degeneration in mice. Nat Protoc 2013, 8:2197-211.

[66] Smith L E, Kopchick J J, Chen W, Knapp J, Kinose F, Daley D, Foley E, Smith R G, Schaeffer J M: Essential role of growth hormone in ischemia-induced retinal neovascularization. Science 1997, 276:1706-9.

[67] Chen J, Connor K M, Aderman C M, Smith L E: Erythropoietin deficiency decreases vascular stability in mice. J Clin Invest 2008, 118:526-33.

[68] Gardiner T A, Gibson D S, de Gooyer T E, de la Cruz V F, McDonald D M, Stitt A W: Inhibition of tumor necrosis factor-alpha improves physiological angiogenesis and reduces pathological neovascularization in ischemic retinopathy. Am J Pathol 2005, 166:637-44.

[69] Chen J, Connor K M, Aderman C M, Willett K L, Aspegren O P, Smith L E: Suppression of retinal neovascularization by erythropoietin siRNA in a mouse model of proliferative retinopathy. Invest Ophthalmol Vis Sci 2009, 50:1329-35.

[70] Aiello L P, Pierce E A, Foley E D, Takagi H, Chen H, Riddle L, Ferrara N, King G L, Smith L E: Suppression of retinal neovascularization in vivo by inhibition of vascular endothelial growth factor (VEGF) using soluble VEGF-receptor chimeric proteins. Proc-Natl-Acad-Sci-U-S-A 1995, 92:10457-61 issn: 0027-8424.

[71] Smith L E, Shen W, Perruzzi C, Soker S, Kinose F, Xu X, Robinson G, Driver S, Bischoff J, Zhang B, Schaeffer J M, Senger D R: Regulation of vascular endothelial growth factor-dependent retinal neovascularization by insulin-like growth factor-1 receptor. Nature Medicine 1999, 5:1390-5.

[72] Lange C, Ehlken C, Martin G, Konzok K, Moscoso Del Prado J, Hansen L L, Agostini H T: Intravitreal injection of the heparin analog 5-amino-2-naphthalenesulfonate reduces retinal neovascularization in mice. Exp Eye Res 2007, 85:323-7.

[73] Xiao S, Bucher F, Wu Y, Rokem A, Lee C S, Marra K V, Fallon R, Diaz-Aguilar S, Aguilar E, Friedlander M, Lee A Y: Fully automated, deep learning segmentation of oxygen-induced retinopathy images. JCI Insight 2017, 2.

What is claimed is:

1. A method of treating a VEGF related condition in an eye of a subject comprising: administering to the eye an anti-VEGF agent consisting of the amino acid residues 27 to 459 of SEQ ID NO: 3.

2. The method of claim 1, wherein the administering comprises an intravitreal injection.

3. The method of claim 1, wherein the VEGF related condition comprises neovascularization.

4. The method of claim 3, wherein the neovascularization is choroidal neovascularization.

5. The method of claim 3, wherein the neovascularization is retinal neovascularization.

6. The method of claim 3, wherein the VEGF related condition is age-related macular degeneration.

* * * * *

SEQUENCE LISTING

```
<160> NUMBER OF SEQ ID NOS: 18

<210> SEQ ID NO 1
<211> LENGTH: 558
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45
```

-continued

```
Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Asp Lys Thr His Thr
                325                 330                 335

Cys Pro Pro Cys Pro Ala Pro Glu Leu Leu Gly Gly Pro Ser Val Phe
            340                 345                 350

Leu Phe Pro Pro Lys Pro Lys Asp Thr Leu Met Ile Ser Arg Thr Pro
        355                 360                 365

Glu Val Thr Cys Val Val Val Asp Val Ser His Glu Asp Pro Glu Val
    370                 375                 380

Lys Phe Asn Trp Tyr Val Asp Gly Val Glu Val His Asn Ala Lys Thr
385                 390                 395                 400

Lys Pro Arg Glu Glu Gln Tyr Asn Ser Thr Tyr Arg Val Val Ser Val
                405                 410                 415

Leu Thr Val Leu His Gln Asp Trp Leu Asn Gly Lys Glu Tyr Lys Cys
            420                 425                 430

Lys Val Ser Asn Lys Ala Leu Pro Ala Pro Ile Glu Lys Thr Ile Ser
        435                 440                 445

Lys Ala Lys Gly Gln Pro Arg Glu Pro Gln Val Tyr Thr Leu Pro Pro
    450                 455                 460
```

-continued

Ser Arg Glu Glu Met Thr Lys Asn Gln Val Ser Leu Thr Cys Leu Val
465 470 475 480

Lys Gly Phe Tyr Pro Ser Asp Ile Ala Val Glu Trp Glu Ser Asn Gly
485 490 495

Gln Pro Glu Asn Asn Tyr Lys Thr Thr Pro Pro Val Leu Asp Ser Asp
500 505 510

Gly Ser Phe Phe Leu Tyr Ser Lys Leu Thr Val Asp Lys Ser Arg Trp
515 520 525

Gln Gln Gly Asn Val Phe Ser Cys Ser Val Met His Glu Ala Leu His
530 535 540

Asn His Tyr Thr Gln Lys Ser Leu Ser Leu Ser Pro Gly Lys
545 550 555

<210> SEQ ID NO 2
<211> LENGTH: 1674
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2
atggtcagct actgggacac cggggtcctg ctgtgcgcgc tgctcagctg tctgcttctc 60
acaggatcta gttcaggttc aaaattaaaa gatcctgaac tgagtttaaa aggcacccag 120
cacatcatgc aagcaggcca gacactgcat ctccaatgca ggggggaagc agcccataaa 180
tggtctttgc ctgaaatggt gagtaaggaa agcgaaaggc tgagcataac taaatctgcc 240
tgtggaagaa atggcaaaca attctgcagt actttaacct tgaacacagc tcaagcaaac 300
cacactggct tctacagctg caaatatcta gctgtaccta cttcaaagaa gaaggaaaca 360
gaatctgcaa tctatatatt tattagtgat acaggtagac ctttcgtaga gatgtacagt 420
gaaatccccg aaattataca catgactgaa ggaagggagc tcgtcattcc ctgccgggtt 480
acgtcaccta acatcactgt tactttaaaa aagtttccac ttgacacttt gatccctgat 540
ggaaaacgca taatctggga cagtagaaag ggcttcatca tatcaaatgc aacgtacaaa 600
gaaatagggc ttctgacctg tgaagcaaca gtcaatgggc atttgtataa gacaaactat 660
ctcacacatc gacaaaccaa tacaatcata gatgtccaaa taagcacacc acgcccagtc 720
aaattactta gaggccatac tcttgtcctc aattgtactg ctaccactcc cttgaacacg 780
agagttcaaa tgacctggag ttaccctgat gaaaaaaata agagagcttc cgtaaggcga 840
cgaattgacc aaagcaattc ccatgccaac atattctaca gtgttcttac tattgacaaa 900
atgcagaaca aagacaaagg actttatact tgtcgtgtaa ggagtggacc atcattcaaa 960
tctgttaaca cctcagtgca tatatatgat aaagacaaaa ctcacacatg cccaccgtgc 1020
ccagcacctg aactcctggg gggaccgtca gtcttcctct tccccccaaa acccaaggac 1080
accctcatga tctcccggac ccctgaggtc acatgcgtgg tggtggacgt gagccacgaa 1140
gaccctgagg tcaagttcaa ctggtacgtg gacggcgtgg aggtgcataa tgccaagaca 1200
aagccgcggg aggagcagta caacagcacg taccgtgtgg tcagcgtcct caccgtcctg 1260
caccaggact ggctgaatgg caaggagtac aagtgcaagg tctccaacaa agccctccca 1320
gcccccatcg agaaaaccat ctccaaagcc aaagggcagc cccgagaacc acaggtgtac 1380
accctgcccc catcccggga ggagatgacc aagaaccagg tcagcctgac ctgcctggtc 1440
aaaggcttct atcccagcga catcgccgtg gagtgggaga gcaatgggca gccggagaac 1500

-continued aactacaaga ccacgcctcc cgtgctggac tccgacggct ccttcttcct ctacagcaag 1560
ctcaccgtgg acaagagcag gtggcagcag gggaacgtct tctcatgctc cgtgatgcac 1620
gaggctctgc acaaccacta cacgcagaag agcctctccc tgtctccggg taaa 1674

<210> SEQ ID NO 3
<211> LENGTH: 459
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

Met Val Ser Tyr Trp Asp Thr Gly Val Leu Leu Cys Ala Leu Leu Ser
1 5 10 15

Cys Leu Leu Leu Thr Gly Ser Ser Ser Gly Ile Phe Ile Ser Asp Thr
20 25 30

Gly Arg Pro Phe Val Glu Met Tyr Ser Glu Ile Pro Glu Ile Ile His
35 40 45

Met Thr Glu Gly Arg Glu Leu Val Ile Pro Cys Arg Val Thr Ser Pro
50 55 60

Asn Ile Thr Val Thr Leu Lys Lys Phe Pro Leu Asp Thr Leu Ile Pro
65 70 75 80

Asp Gly Lys Arg Ile Ile Trp Asp Ser Arg Lys Gly Phe Ile Ile Ser
85 90 95

Asn Ala Thr Tyr Lys Glu Ile Gly Leu Leu Thr Cys Glu Ala Thr Val
100 105 110

Asn Gly His Leu Tyr Lys Thr Asn Tyr Leu Thr His Arg Gln Thr Asn
115 120 125

Thr Ile Ile Asp Val Gln Ile Ser Thr Pro Arg Pro Val Lys Leu Leu
130 135 140

Arg Gly His Thr Leu Val Leu Asn Cys Thr Ala Thr Thr Pro Leu Asn
145 150 155 160

Thr Arg Val Gln Met Thr Trp Ser Tyr Pro Asp Glu Lys Asn Lys Arg
165 170 175

Ala Ser Val Arg Arg Arg Ile Asp Gln Ser Asn Ser His Ala Asn Ile
180 185 190

Phe Tyr Ser Val Leu Thr Ile Asp Lys Met Gln Asn Lys Asp Lys Gly
195 200 205

Leu Tyr Thr Cys Arg Val Arg Ser Gly Pro Ser Phe Lys Ser Val Asn
210 215 220

Thr Ser Val His Ile Tyr Asp Lys Asp Lys Thr His Thr Cys Pro Pro
225 230 235 240

Cys Pro Ala Pro Glu Leu Leu Gly Gly Pro Ser Val Phe Leu Phe Pro
245 250 255

Pro Lys Pro Lys Asp Thr Leu Met Ile Ser Arg Thr Pro Glu Val Thr
260 265 270

Cys Val Val Val Asp Val Ser His Glu Asp Pro Glu Val Lys Phe Asn
275 280 285

Trp Tyr Val Asp Gly Val Glu Val His Asn Ala Lys Thr Lys Pro Arg
290 295 300

Glu Glu Gln Tyr Asn Ser Thr Tyr Arg Val Val Ser Val Leu Thr Val
305 310 315 320

Leu His Gln Asp Trp Leu Asn Gly Lys Glu Tyr Lys Cys Lys Val Ser
325 330 335

-continued

Asn Lys Ala Leu Pro Ala Pro Ile Glu Lys Thr Ile Ser Lys Ala Lys
340 345 350

Gly Gln Pro Arg Glu Pro Gln Val Tyr Thr Leu Pro Pro Ser Arg Glu
355 360 365

Glu Met Thr Lys Asn Gln Val Ser Leu Thr Cys Leu Val Lys Gly Phe
370 375 380

Tyr Pro Ser Asp Ile Ala Val Glu Trp Glu Ser Asn Gly Gln Pro Glu
385 390 395 400

Asn Asn Tyr Lys Thr Thr Pro Pro Val Leu Asp Ser Asp Gly Ser Phe
405 410 415

Phe Leu Tyr Ser Lys Leu Thr Val Asp Lys Ser Arg Trp Gln Gln Gly
420 425 430

Asn Val Phe Ser Cys Ser Val Met His Glu Ala Leu His Asn His Tyr
435 440 445

Thr Gln Lys Ser Leu Ser Leu Ser Pro Gly Lys
450 455

<210> SEQ ID NO 4
<211> LENGTH: 1377
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4
atggtcagct actgggacac cggggtcctg ctgtgcgcgc tgctcagctg tctgcttctc 60
acaggatcta gttcaggtat atttattagt gatacaggta gacctttcgt agagatgtac 120
agtgaaatcc ccgaaattat acacatgact gaaggaaggg agctcgtcat tccctgccgg 180
gttacgtcac ctaacatcac tgttacttta aaaaagtttc cacttgacac tttgatccct 240
gatggaaaac gcataatctg ggacagtaga aagggcttca tcatatcaaa tgcaacgtac 300
aaagaaatag ggcttctgac ctgtgaagca acagtcaatg ggcatttgta taagacaaac 360
tatctcacac atcgacaaac caatacaatc atagatgtcc aaataagcac accacgccca 420
gtcaaattac ttagaggcca tactcttgtc ctcaattgta ctgctaccac tcccttgaac 480
acgagagttc aaatgacctg gagttaccct gatgaaaaaa ataagagagc ttccgtaagg 540
cgacgaattg accaaagcaa ttcccatgcc aacatattct acagtgttct tactattgac 600
aaaatgcaga acaaagacaa aggactttat acttgtcgtg taaggagtgg accatcattc 660
aaatctgtta acacctcagt gcatatatat gataaagaca aaactcacac atgcccaccg 720
tgcccagcac ctgaactcct ggggggaccg tcagtcttcc tcttcccccc aaaacccaag 780
gacaccctca tgatctcccg gacccctgag gtcacatgcg tggtggtgga cgtgagccac 840
gaagaccctg aggtcaagtt caactggtac gtggacggcg tggaggtgca taatgccaag 900
acaaagccgc gggaggagca gtacaacagc acgtaccgtg tggtcagcgt cctcaccgtc 960
ctgcaccagg actggctgaa tggcaaggag tacaagtgca aggtctccaa caaagccctc 1020
ccagccccca tcgagaaaac catctccaaa gccaaagggc agccccgaga accacaggtg 1080
tacaccctgc ccccatcccg ggaggagatg accaagaacc aggtcagcct gacctgcctg 1140
gtcaaaggct tctatcccag cgacatcgcc gtggagtggg agagcaatgg gcagccggag 1200
aacaactaca agaccacgcc tcccgtgctg gactccgacg gctccttctt cctctacagc 1260
aagctcaccg tggacaagag caggtggcag caggggaacg tcttctcatg ctccgtgatg 1320

-continued

```
cacgaggctc tgcacaacca ctacacgcag aagagcctct ccctgtctcc gggtaaa      1377


<210> SEQ ID NO 5
<211> LENGTH: 659
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Val Gln Ile Ser
                325                 330                 335

Thr Pro Arg Pro Val Lys Leu Leu Arg Gly His Thr Leu Val Leu Asn
            340                 345                 350
```

-continued

```
Cys Thr Ala Thr Thr Pro Leu Asn Thr Arg Val Gln Met Thr Trp Ser
        355                 360                 365

Tyr Pro Asp Glu Lys Asn Lys Arg Ala Ser Val Arg Arg Arg Ile Asp
    370                 375                 380

Gln Ser Asn Ser His Ala Asn Ile Phe Tyr Ser Val Leu Thr Ile Asp
385                 390                 395                 400

Lys Met Gln Asn Lys Asp Lys Gly Leu Tyr Thr Cys Arg Val Arg Ser
                405                 410                 415

Gly Pro Ser Phe Lys Ser Val Asn Thr Ser Val His Ile Tyr Asp Lys
            420                 425                 430

Asp Lys Thr His Thr Cys Pro Pro Cys Pro Ala Pro Glu Leu Leu Gly
        435                 440                 445

Gly Pro Ser Val Phe Leu Phe Pro Pro Lys Pro Lys Asp Thr Leu Met
    450                 455                 460

Ile Ser Arg Thr Pro Glu Val Thr Cys Val Val Val Asp Val Ser His
465                 470                 475                 480

Glu Asp Pro Glu Val Lys Phe Asn Trp Tyr Val Asp Gly Val Glu Val
                485                 490                 495

His Asn Ala Lys Thr Lys Pro Arg Glu Glu Gln Tyr Asn Ser Thr Tyr
            500                 505                 510

Arg Val Val Ser Val Leu Thr Val Leu His Gln Asp Trp Leu Asn Gly
        515                 520                 525

Lys Glu Tyr Lys Cys Lys Val Ser Asn Lys Ala Leu Pro Ala Pro Ile
    530                 535                 540

Glu Lys Thr Ile Ser Lys Ala Lys Gly Gln Pro Arg Glu Pro Gln Val
545                 550                 555                 560

Tyr Thr Leu Pro Pro Ser Arg Glu Glu Met Thr Lys Asn Gln Val Ser
                565                 570                 575

Leu Thr Cys Leu Val Lys Gly Phe Tyr Pro Ser Asp Ile Ala Val Glu
            580                 585                 590

Trp Glu Ser Asn Gly Gln Pro Glu Asn Asn Tyr Lys Thr Thr Pro Pro
        595                 600                 605

Val Leu Asp Ser Asp Gly Ser Phe Phe Leu Tyr Ser Lys Leu Thr Val
    610                 615                 620

Asp Lys Ser Arg Trp Gln Gln Gly Asn Val Phe Ser Cys Ser Val Met
625                 630                 635                 640

His Glu Ala Leu His Asn His Tyr Thr Gln Lys Ser Leu Ser Leu Ser
                645                 650                 655

Pro Gly Lys


<210> SEQ ID NO 6
<211> LENGTH: 1977
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

atggtcagct actgggacac cggggtcctg ctgtgcgcgc tgctcagctg tctgcttctc      60

acaggatcta gttcaggttc aaaattaaaa gatcctgaac tgagtttaaa aggcacccag     120

cacatcatgc aagcaggcca gacactgcat ctccaatgca gggggggaagc agcccataaa     180

tggtctttgc ctgaaatggt gagtaaggaa agcgaaaggc tgagcataac taaatctgcc     240
```

-continued

```
tgtggaagaa atggcaaaca attctgcagt actttaacct tgaacacagc tcaagcaaac    300

cacactggct tctacagctg caaatatcta gctgtaccta cttcaaagaa gaaggaaaca    360

gaatctgcaa tctatatatt tattagtgat acaggtagac ctttcgtaga gatgtacagt    420

gaaatccccg aaattataca catgactgaa ggaagggagc tcgtcattcc ctgccgggtt    480

acgtcaccta acatcactgt tactttaaaa aagtttccac ttgacacttt gatccctgat    540

ggaaaacgca taatctggga cagtagaaag ggcttcatca tatcaaatgc aacgtacaaa    600

gaaatagggc ttctgacctg tgaagcaaca gtcaatgggc atttgtataa gacaaactat    660

ctcacacatc gacaaaccaa tacaatcata gatgtccaaa taagcacacc acgcccagtc    720

aaattactta gaggccatac tcttgtcctc aattgtactg ctaccactcc cttgaacacg    780

agagttcaaa tgacctggag ttaccctgat gaaaaaaata agagagcttc cgtaaggcga    840

cgaattgacc aaagcaattc ccatgccaac atattctaca gtgttcttac tattgacaaa    900

atgcagaaca aagacaaagg actttatact tgtcgtgtaa ggagtggacc atcattcaaa    960

tctgttaaca cctcagtgca tatatatgat aaagcagtcc aaataagcac accacgccca   1020

gtcaaattac ttagaggcca tactcttgtc ctcaattgta ctgctaccac tcccttgaac   1080

acgagagttc aaatgacctg gagttaccct gatgaaaaaa ataagagagc ttccgtaagg   1140

cgacgaattg accaaagcaa ttcccatgcc aacatattct acagtgttct tactattgac   1200

aaaatgcaga acaaagacaa aggactttat acttgtcgtg taaggagtgg accatcattc   1260

aaatctgtta acacctcagt gcatatatat gataaagaca aaactcacac atgcccaccg   1320

tgcccagcac ctgaactcct ggggggaccg tcagtcttcc tcttcccccc aaaacccaag   1380

gacaccctca tgatctcccg gacccctgag gtcacatgcg tggtggtgga cgtgagccac   1440

gaagaccctg aggtcaagtt caactggtac gtggacggcg tggaggtgca taatgccaag   1500

acaaagccgc gggaggagca gtacaacagc acgtaccgtg tggtcagcgt cctcaccgtc   1560

ctgcaccagg actggctgaa tggcaaggag tacaagtgca aggtctccaa caaagccctc   1620

ccagccccca tcgagaaaac catctccaaa gccaaagggc agccccgaga accacaggtg   1680

tacaccctgc ccccatcccg ggaggagatg accaagaacc aggtcagcct gacctgcctg   1740

gtcaaaggct tctatcccag cgacatcgcc gtggagtggg agagcaatgg gcagccggag   1800

aacaactaca agaccacgcc tcccgtgctg gactccgacg gctccttctt cctctacagc   1860

aagctcaccg tggacaagag caggtggcag caggggaacg tcttctcatg ctccgtgatg   1920

cacgaggctc tgcacaacca ctacacgcag aagagcctct ccctgtctcc gggtaaa      1977
```

```
<210> SEQ ID NO 7
<211> LENGTH: 560
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ile Phe Ile Ser Asp Thr
            20                  25                  30

Gly Arg Pro Phe Val Glu Met Tyr Ser Glu Ile Pro Glu Ile Ile His
        35                  40                  45

Met Thr Glu Gly Arg Glu Leu Val Ile Pro Cys Arg Val Thr Ser Pro
```

-continued

```
    50                  55                  60

Asn Ile Thr Val Thr Leu Lys Lys Phe Pro Leu Asp Thr Leu Ile Pro
65                  70                  75                  80

Asp Gly Lys Arg Ile Ile Trp Asp Ser Arg Lys Gly Phe Ile Ile Ser
                85                  90                  95

Asn Ala Thr Tyr Lys Glu Ile Gly Leu Leu Thr Cys Glu Ala Thr Val
            100                 105                 110

Asn Gly His Leu Tyr Lys Thr Asn Tyr Leu Thr His Arg Gln Thr Asn
        115                 120                 125

Thr Ile Ile Asp Val Gln Ile Ser Thr Pro Arg Pro Val Lys Leu Leu
    130                 135                 140

Arg Gly His Thr Leu Val Leu Asn Cys Thr Ala Thr Thr Pro Leu Asn
145                 150                 155                 160

Thr Arg Val Gln Met Thr Trp Ser Tyr Pro Asp Glu Lys Asn Lys Arg
                165                 170                 175

Ala Ser Val Arg Arg Arg Ile Asp Gln Ser Asn Ser His Ala Asn Ile
            180                 185                 190

Phe Tyr Ser Val Leu Thr Ile Asp Lys Met Gln Asn Lys Asp Lys Gly
        195                 200                 205

Leu Tyr Thr Cys Arg Val Arg Ser Gly Pro Ser Phe Lys Ser Val Asn
    210                 215                 220

Thr Ser Val His Ile Tyr Asp Lys Ala Val Gln Ile Ser Thr Pro Arg
225                 230                 235                 240

Pro Val Lys Leu Leu Arg Gly His Thr Leu Val Leu Asn Cys Thr Ala
                245                 250                 255

Thr Thr Pro Leu Asn Thr Arg Val Gln Met Thr Trp Ser Tyr Pro Asp
            260                 265                 270

Glu Lys Asn Lys Arg Ala Ser Val Arg Arg Arg Ile Asp Gln Ser Asn
        275                 280                 285

Ser His Ala Asn Ile Phe Tyr Ser Val Leu Thr Ile Asp Lys Met Gln
    290                 295                 300

Asn Lys Asp Lys Gly Leu Tyr Thr Cys Arg Val Arg Ser Gly Pro Ser
305                 310                 315                 320

Phe Lys Ser Val Asn Thr Ser Val His Ile Tyr Asp Lys Asp Lys Thr
                325                 330                 335

His Thr Cys Pro Pro Cys Pro Ala Pro Glu Leu Leu Gly Gly Pro Ser
            340                 345                 350

Val Phe Leu Phe Pro Pro Lys Pro Lys Asp Thr Leu Met Ile Ser Arg
        355                 360                 365

Thr Pro Glu Val Thr Cys Val Val Val Asp Val Ser His Glu Asp Pro
    370                 375                 380

Glu Val Lys Phe Asn Trp Tyr Val Asp Gly Val Glu Val His Asn Ala
385                 390                 395                 400

Lys Thr Lys Pro Arg Glu Glu Gln Tyr Asn Ser Thr Tyr Arg Val Val
                405                 410                 415

Ser Val Leu Thr Val Leu His Gln Asp Trp Leu Asn Gly Lys Glu Tyr
            420                 425                 430

Lys Cys Lys Val Ser Asn Lys Ala Leu Pro Ala Pro Ile Glu Lys Thr
        435                 440                 445

Ile Ser Lys Ala Lys Gly Gln Pro Arg Glu Pro Gln Val Tyr Thr Leu
    450                 455                 460

Pro Pro Ser Arg Glu Glu Met Thr Lys Asn Gln Val Ser Leu Thr Cys
465                 470                 475                 480
```

-continued

```
Leu Val Lys Gly Phe Tyr Pro Ser Asp Ile Ala Val Glu Trp Glu Ser
                485                 490                 495

Asn Gly Gln Pro Glu Asn Asn Tyr Lys Thr Thr Pro Pro Val Leu Asp
            500                 505                 510

Ser Asp Gly Ser Phe Phe Leu Tyr Ser Lys Leu Thr Val Asp Lys Ser
        515                 520                 525

Arg Trp Gln Gln Gly Asn Val Phe Ser Cys Ser Val Met His Glu Ala
    530                 535                 540

Leu His Asn His Tyr Thr Gln Lys Ser Leu Ser Leu Ser Pro Gly Lys
545                 550                 555                 560


<210> SEQ ID NO 8
<211> LENGTH: 1680
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

atggtcagct actgggacac cggggtcctg ctgtgcgcgc tgctcagctg tctgcttctc     60

acaggatcta gttcaggtat atttattagt gatacaggta gacctttcgt agagatgtac    120

agtgaaatcc ccgaaattat acacatgact gaaggaaggg agctcgtcat tccctgccgg    180

gttacgtcac ctaacatcac tgttacttta aaaaagtttc cacttgacac tttgatccct    240

gatggaaaac gcataatctg ggacagtaga aagggcttca tcatatcaaa tgcaacgtac    300

aaagaaatag ggcttctgac ctgtgaagca acagtcaatg ggcatttgta taagacaaac    360

tatctcacac atcgacaaac caatacaatc atagatgtcc aaataagcac accacgccca    420

gtcaaattac ttagaggcca tactcttgtc ctcaattgta ctgctaccac tcccttgaac    480

acgagagttc aaatgacctg gagttaccct gatgaaaaaa ataagagagc ttccgtaagg    540

cgacgaattg accaaagcaa ttcccatgcc aacatattct acagtgttct tactattgac    600

aaaatgcaga acaaagacaa aggactttat acttgtcgtg taaggagtgg accatcattc    660

aaatctgtta acacctcagt gcatatatat gataaagcag tccaaataag cacaccacgc    720

ccagtcaaat tacttagagg ccatactctt gtcctcaatt gtactgctac cactcccttg    780

aacacgagag ttcaaatgac ctggagttac cctgatgaaa aaaataagag agcttccgta    840

aggcgacgaa ttgaccaaag caattcccat gccaacatat tctacagtgt tcttactatt    900

gacaaaatgc agaacaaaga caaaggactt tatacttgtc gtgtaaggag tggaccatca    960

ttcaaatctg ttaacacctc agtgcatata tatgataaag acaaaactca cacatgccca   1020

ccgtgcccag cacctgaact cctgggggga ccgtcagtct tcctcttccc cccaaaaccc   1080

aaggacaccc tcatgatctc ccggacccct gaggtcacat gcgtggtggt ggacgtgagc   1140

cacgaagacc ctgaggtcaa gttcaactgg tacgtggacg gcgtggaggt gcataatgcc   1200

aagacaaagc cgcgggagga gcagtacaac agcacgtacc gtgtggtcag cgtcctcacc   1260

gtcctgcacc aggactggct gaatggcaag gagtacaagt gcaaggtctc caacaaagcc   1320

ctcccagccc ccatcgagaa aaccatctcc aaagccaaag ggcagccccg agaaccacag   1380

gtgtacaccc tgcccccatc ccgggaggag atgaccaaga accaggtcag cctgacctgc   1440

ctggtcaaag gcttctatcc cagcgacatc gccgtggagt gggagagcaa tgggcagccg   1500

gagaacaact acaagaccac gcctcccgtg ctggactccg acggctcctt cttcctctac   1560
```

agcaagctca ccgtggacaa gagcaggtgg cagcagggga acgtcttctc atgctccgtg 1620
atgcacgagg ctctgcacaa ccactacacg cagaagagcc tctccctgtc tccgggtaaa 1680

<210> SEQ ID NO 9
<211> LENGTH: 655
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
```

```
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Asp Lys Thr His
            420                 425                 430

Thr Cys Pro Pro Cys Pro Ala Pro Glu Leu Leu Gly Gly Pro Ser Val
        435                 440                 445

Phe Leu Phe Pro Pro Lys Pro Lys Asp Thr Leu Met Ile Ser Arg Thr
    450                 455                 460

Pro Glu Val Thr Cys Val Val Val Asp Val Ser His Glu Asp Pro Glu
465                 470                 475                 480

Val Lys Phe Asn Trp Tyr Val Asp Gly Val Glu Val His Asn Ala Lys
                485                 490                 495

Thr Lys Pro Arg Glu Glu Gln Tyr Asn Ser Thr Tyr Arg Val Val Ser
            500                 505                 510

Val Leu Thr Val Leu His Gln Asp Trp Leu Asn Gly Lys Glu Tyr Lys
        515                 520                 525

Cys Lys Val Ser Asn Lys Ala Leu Pro Ala Pro Ile Glu Lys Thr Ile
    530                 535                 540

Ser Lys Ala Lys Gly Gln Pro Arg Glu Pro Gln Val Tyr Thr Leu Pro
545                 550                 555                 560

Pro Ser Arg Glu Glu Met Thr Lys Asn Gln Val Ser Leu Thr Cys Leu
                565                 570                 575

Val Lys Gly Phe Tyr Pro Ser Asp Ile Ala Val Glu Trp Glu Ser Asn
            580                 585                 590

Gly Gln Pro Glu Asn Asn Tyr Lys Thr Thr Pro Pro Val Leu Asp Ser
        595                 600                 605

Asp Gly Ser Phe Phe Leu Tyr Ser Lys Leu Thr Val Asp Lys Ser Arg
    610                 615                 620

Trp Gln Gln Gly Asn Val Phe Ser Cys Ser Val Met His Glu Ala Leu
625                 630                 635                 640

His Asn His Tyr Thr Gln Lys Ser Leu Ser Leu Ser Pro Gly Lys
                645                 650                 655


<210> SEQ ID NO 10
<211> LENGTH: 1965
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

atggtcagct actgggacac cggggtcctg ctgtgcgcgc tgctcagctg tctgcttctc      60

acaggatcta gttcaggttc aaaattaaaa gatcctgaac tgagtttaaa aggcacccag     120

cacatcatgc aagcaggcca gacactgcat ctccaatgca ggggggaagc agcccataaa     180

tggtctttgc ctgaaatggt gagtaaggaa agcgaaaggc tgagcataac taaatctgcc     240

tgtggaagaa atggcaaaca attctgcagt actttaacct tgaacacagc tcaagcaaac     300
```

-continued

```
cacactggct tctacagctg caaatatcta gctgtaccta cttcaaagaa gaaggaaaca    360

gaatctgcaa tctatatatt tattagtgat acaggtagac ctttcgtaga gatgtacagt    420

gaaatccccg aaattataca catgactgaa ggaagggagc tcgtcattcc ctgccgggtt    480

acgtcaccta acatcactgt tactttaaaa aagtttccac ttgacacttt gatccctgat    540

ggaaaacgca taatctggga cagtagaaag ggcttcatca tatcaaatgc aacgtacaaa    600

gaaatagggc ttctgacctg tgaagcaaca gtcaatgggc atttgtataa gacaaactat    660

ctcacacatc gacaaaccaa tacaatcata gatgtccaaa taagcacacc acgcccagtc    720

aaattactta gaggccatac tcttgtcctc aattgtactg ctaccactcc cttgaacacg    780

agagttcaaa tgacctggag ttaccctgat gaaaaaaata agagagcttc cgtaaggcga    840

cgaattgacc aaagcaattc ccatgccaac atattctaca gtgttcttac tattgacaaa    900

atgcagaaca aagacaaagg actttatact tgtcgtgtaa ggagtggacc atcattcaaa    960

tctgttaaca cctcagtgca tatatatgat aaagcattca tcactgtgaa acatcgaaaa   1020

cagcaggtgc ttgaaaccgt agctggcaag cggtcttacc ggctctctat gaaagtgaag   1080

gcatttccct cgccggaagt tgtatggtta aaagatgggt tacctgcgac tgagaaatct   1140

gctcgctatt tgactcgtgg ctactcgtta attatcaagg acgtaactga agaggatgca   1200

gggaattata caatcttgct gagcataaaa cagtcaaatg tgtttaaaaa cctcactgcc   1260

actctaattg tcaatgtgaa acccgacaaa actcacacat gcccaccgtg cccagcacct   1320

gaactcctgg ggggaccgtc agtcttcctc ttccccccaa aacccaagga caccctcatg   1380

atctcccgga cccctgaggt cacatgcgtg gtggtggacg tgagccacga agaccctgag   1440

gtcaagttca actggtacgt ggacggcgtg gaggtgcata atgccaagac aaagccgcgg   1500

gaggagcagt acaacagcac gtaccgtgtg gtcagcgtcc tcaccgtcct gcaccaggac   1560

tggctgaatg gcaaggagta caagtgcaag gtctccaaca aagccctccc agcccccatc   1620

gagaaaacca tctccaaagc caaagggcag ccccgagaac cacaggtgta caccctgccc   1680

ccatcccggg aggagatgac caagaaccag gtcagcctga cctgcctggt caaaggcttc   1740

tatcccagcg acatcgccgt ggagtgggag agcaatgggc agccggagaa caactacaag   1800

accacgcctc ccgtgctgga ctccgacggc tccttcttcc tctacagcaa gctcaccgtg   1860

gacaagagca ggtggcagca ggggaacgtc ttctcatgct ccgtgatgca cgaggctctg   1920

cacaaccact acacgcagaa gagcctctcc ctgtctccgg gtaaa                   1965
```

```
<210> SEQ ID NO 11
<211> LENGTH: 556
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ile Phe Ile Ser Asp Thr
            20                  25                  30

Gly Arg Pro Phe Val Glu Met Tyr Ser Glu Ile Pro Glu Ile Ile His
        35                  40                  45

Met Thr Glu Gly Arg Glu Leu Val Ile Pro Cys Arg Val Thr Ser Pro
    50                  55                  60
```

```
Asn Ile Thr Val Thr Leu Lys Lys Phe Pro Leu Asp Thr Leu Ile Pro
65                  70                  75                  80

Asp Gly Lys Arg Ile Ile Trp Asp Ser Arg Lys Gly Phe Ile Ile Ser
                85                  90                  95

Asn Ala Thr Tyr Lys Glu Ile Gly Leu Leu Thr Cys Glu Ala Thr Val
            100                 105                 110

Asn Gly His Leu Tyr Lys Thr Asn Tyr Leu Thr His Arg Gln Thr Asn
        115                 120                 125

Thr Ile Ile Asp Val Gln Ile Ser Thr Pro Arg Pro Val Lys Leu Leu
    130                 135                 140

Arg Gly His Thr Leu Val Leu Asn Cys Thr Ala Thr Thr Pro Leu Asn
145                 150                 155                 160

Thr Arg Val Gln Met Thr Trp Ser Tyr Pro Asp Glu Lys Asn Lys Arg
                165                 170                 175

Ala Ser Val Arg Arg Arg Ile Asp Gln Ser Asn Ser His Ala Asn Ile
            180                 185                 190

Phe Tyr Ser Val Leu Thr Ile Asp Lys Met Gln Asn Lys Asp Lys Gly
        195                 200                 205

Leu Tyr Thr Cys Arg Val Arg Ser Gly Pro Ser Phe Lys Ser Val Asn
    210                 215                 220

Thr Ser Val His Ile Tyr Asp Lys Ala Phe Ile Thr Val Lys His Arg
225                 230                 235                 240

Lys Gln Gln Val Leu Glu Thr Val Ala Gly Lys Arg Ser Tyr Arg Leu
                245                 250                 255

Ser Met Lys Val Lys Ala Phe Pro Ser Pro Glu Val Val Trp Leu Lys
            260                 265                 270

Asp Gly Leu Pro Ala Thr Glu Lys Ser Ala Arg Tyr Leu Thr Arg Gly
        275                 280                 285

Tyr Ser Leu Ile Ile Lys Asp Val Thr Glu Glu Asp Ala Gly Asn Tyr
    290                 295                 300

Thr Ile Leu Leu Ser Ile Lys Gln Ser Asn Val Phe Lys Asn Leu Thr
305                 310                 315                 320

Ala Thr Leu Ile Val Asn Val Lys Pro Asp Lys Thr His Thr Cys Pro
                325                 330                 335

Pro Cys Pro Ala Pro Glu Leu Leu Gly Gly Pro Ser Val Phe Leu Phe
            340                 345                 350

Pro Pro Lys Pro Lys Asp Thr Leu Met Ile Ser Arg Thr Pro Glu Val
        355                 360                 365

Thr Cys Val Val Val Asp Val Ser His Glu Asp Pro Glu Val Lys Phe
    370                 375                 380

Asn Trp Tyr Val Asp Gly Val Glu Val His Asn Ala Lys Thr Lys Pro
385                 390                 395                 400

Arg Glu Glu Gln Tyr Asn Ser Thr Tyr Arg Val Val Ser Val Leu Thr
                405                 410                 415

Val Leu His Gln Asp Trp Leu Asn Gly Lys Glu Tyr Lys Cys Lys Val
            420                 425                 430

Ser Asn Lys Ala Leu Pro Ala Pro Ile Glu Lys Thr Ile Ser Lys Ala
        435                 440                 445

Lys Gly Gln Pro Arg Glu Pro Gln Val Tyr Thr Leu Pro Pro Ser Arg
    450                 455                 460

Glu Glu Met Thr Lys Asn Gln Val Ser Leu Thr Cys Leu Val Lys Gly
465                 470                 475                 480
```

-continued

```
Phe Tyr Pro Ser Asp Ile Ala Val Glu Trp Glu Ser Asn Gly Gln Pro
                485                 490                 495

Glu Asn Asn Tyr Lys Thr Thr Pro Pro Val Leu Asp Ser Asp Gly Ser
            500                 505                 510

Phe Phe Leu Tyr Ser Lys Leu Thr Val Asp Lys Ser Arg Trp Gln Gln
        515                 520                 525

Gly Asn Val Phe Ser Cys Ser Val Met His Glu Ala Leu His Asn His
    530                 535                 540

Tyr Thr Gln Lys Ser Leu Ser Leu Ser Pro Gly Lys
545                 550                 555


<210> SEQ ID NO 12
<211> LENGTH: 1668
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

atggtcagct actgggacac cggggtcctg ctgtgcgcgc tgctcagctg tctgcttctc     60

acaggatcta gttcaggtat atttattagt gatacaggta gacctttcgt agagatgtac    120

agtgaaatcc ccgaaattat acacatgact gaaggaaggg agctcgtcat tccctgccgg    180

gttacgtcac ctaacatcac tgttacttta aaaaagtttc cacttgacac tttgatccct    240

gatggaaaac gcataatctg ggacagtaga aagggcttca tcatatcaaa tgcaacgtac    300

aaagaaatag ggcttctgac ctgtgaagca acagtcaatg ggcatttgta taagacaaac    360

tatctcacac atcgacaaac caatacaatc atagatgtcc aaataagcac accacgccca    420

gtcaaattac ttagaggcca tactcttgtc ctcaattgta ctgctaccac tcccttgaac    480

acgagagttc aaatgacctg gagttaccct gatgaaaaaa ataagagagc ttccgtaagg    540

cgacgaattg accaaagcaa ttcccatgcc aacatattct acagtgttct tactattgac    600

aaaatgcaga acaaagacaa aggactttat acttgtcgtg taaggagtgg accatcattc    660

aaatctgtta acacctcagt gcatatatat gataaagcat tcatcactgt gaaacatcga    720

aaacagcagg tgcttgaaac cgtagctggc aagcggtctt accggctctc tatgaaagtg    780

aaggcatttc cctcgccgga agttgtatgg ttaaaagatg ggttacctgc gactgagaaa    840

tctgctcgct atttgactcg tggctactcg ttaattatca aggacgtaac tgaagaggat    900

gcagggaatt atacaatctt gctgagcata aaacagtcaa atgtgtttaa aaacctcact    960

gccactctaa ttgtcaatgt gaaacccgac aaaactcaca catgcccacc gtgcccagca   1020

cctgaactcc tggggggacc gtcagtcttc ctcttccccc caaaacccaa ggacaccctc   1080

atgatctccc ggacccctga ggtcacatgc gtggtggtgg acgtgagcca cgaagaccct   1140

gaggtcaagt tcaactggta cgtggacggc gtggaggtgc ataatgccaa gacaaagccg   1200

cgggaggagc agtacaacag cacgtaccgt gtggtcagcg tcctcaccgt cctgcaccag   1260

gactggctga atggcaagga gtacaagtgc aaggtctcca acaaagccct cccagccccc   1320

atcgagaaaa ccatctccaa agccaaaggg cagccccgag aaccacaggt gtacaccctg   1380

cccccatccc gggaggagat gaccaagaac caggtcagcc tgacctgcct ggtcaaaggc   1440

ttctatccca gcgacatcgc cgtggagtgg gagagcaatg ggcagccgga gaacaactac   1500

aagaccacgc ctcccgtgct ggactccgac ggctccttct tcctctacag caagctcacc   1560

gtggacaaga gcaggtggca gcaggggaac gtcttctcat gctccgtgat gcacgaggct   1620
```

```
ctgcacaacc actacacgca gaagagcctc tccctgtctc cgggtaaa              1668


<210> SEQ ID NO 13
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ile Phe Ile Ser Asp Thr
            20                  25                  30

Gly Arg Pro Phe Val Glu Met Tyr Ser Glu Ile Pro Glu Ile Ile His
        35                  40                  45

Met Thr Glu Gly Arg Glu Leu Val Ile Pro Cys Arg Val Thr Ser Pro
    50                  55                  60

Asn Ile Thr Val Thr Leu Lys Lys Phe Pro Leu Asp Thr Leu Ile Pro
65                  70                  75                  80

Asp Gly Lys Arg Ile Ile Trp Asp Ser Arg Lys Gly Phe Ile Ile Ser
                85                  90                  95

Asn Ala Thr Tyr Lys Glu Ile Gly Leu Leu Thr Cys Glu Ala Thr Val
            100                 105                 110

Asn Gly His Leu Tyr Lys Thr Asn Tyr Leu Thr His Arg Gln Thr Asn
        115                 120                 125

Thr Ile Ile Asp Val Phe Ile Thr Val Lys His Arg Lys Gln Gln Val
    130                 135                 140

Leu Glu Thr Val Ala Gly Lys Arg Ser Tyr Arg Leu Ser Met Lys Val
145                 150                 155                 160

Lys Ala Phe Pro Ser Pro Glu Val Val Trp Leu Lys Asp Gly Leu Pro
                165                 170                 175

Ala Thr Glu Lys Ser Ala Arg Tyr Leu Thr Arg Gly Tyr Ser Leu Ile
            180                 185                 190

Ile Lys Asp Val Thr Glu Glu Asp Ala Gly Asn Tyr Thr Ile Leu Leu
        195                 200                 205

Ser Ile Lys Gln Ser Asn Val Phe Lys Asn Leu Thr Ala Thr Leu Ile
    210                 215                 220

Val Asn Val Lys Pro Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350
```

-continued

```
Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455
```

<210> SEQ ID NO 14
<211> LENGTH: 1368
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
atggtcagct actgggacac cggggtcctg ctgtgcgcgc tgctcagctg tctgcttctc     60

acaggatcta gttcaggtat atttattagt gatacaggta gacctttcgt agagatgtac    120

agtgaaatcc ccgaaattat acacatgact gaaggaaggg agctcgtcat tccctgccgg    180

gttacgtcac ctaacatcac tgttacttta aaaaagtttc cacttgacac tttgatccct    240

gatggaaaac gcataatctg ggacagtaga aagggcttca tcatatcaaa tgcaacgtac    300

aaagaaatag ggcttctgac ctgtgaagca acagtcaatg ggcatttgta taagacaaac    360

tatctcacac atcgacaaac caatacaatc atagatgtct tcatcactgt gaaacatcga    420

aaacagcagg tgcttgaaac cgtagctggc aagcggtctt accggctctc tatgaaagtg    480

aaggcatttc cctcgccgga agttgtatgg ttaaaagatg ggttacctgc gactgagaaa    540

tctgctcgct atttgactcg tggctactcg ttaattatca aggacgtaac tgaagaggat    600

gcagggaatt atacaatctt gctgagcata aaacagtcaa atgtgtttaa aaacctcact    660

gccactctaa ttgtcaatgt gaaacccgac aaaactcaca catgcccacc gtgcccagca    720

cctgaactcc tggggggacc gtcagtcttc ctcttccccc caaaacccaa ggacaccctc    780

atgatctccc ggacccctga ggtcacatgc gtggtggtgg acgtgagcca cgaagaccct    840

gaggtcaagt tcaactggta cgtggacggc gtggaggtgc ataatgccaa gacaaagccg    900

cgggaggagc agtacaacag cacgtaccgt gtggtcagcg tcctcaccgt cctgcaccag    960

gactggctga atggcaagga gtacaagtgc aaggtctcca acaaagccct cccagccccc   1020

atcgagaaaa ccatctccaa agccaaaggg cagccccgag aaccacaggt gtacaccctg   1080

cccccatccc gggaggagat gaccaagaac caggtcagcc tgacctgcct ggtcaaaggc   1140

ttctatccca gcgacatcgc cgtggagtgg gagagcaatg ggcagccgga gaacaactac   1200

aagaccacgc ctcccgtgct ggactccgac ggctccttct tcctctacag caagctcacc   1260

gtggacaaga gcaggtggca gcaggggaac gtcttctcat gctccgtgat gcacgaggct   1320

ctgcacaacc actacacgca gaagagcctc tccctgtctc cgggtaaa                1368
```

<210> SEQ ID NO 15
<211> LENGTH: 97
<212> TYPE: PRT
<213> ORGANISM: Homo sapiens

<400> SEQUENCE: 15

```
Pro Glu Leu Ser Leu Lys Gly Thr Gln His Ile Met Gln Ala Gly Gln
1               5                   10                  15

Thr Leu His Leu Gln Cys Arg Gly Glu Ala Ala His Lys Trp Ser Leu
            20                  25                  30

Pro Glu Met Val Ser Lys Glu Ser Glu Arg Leu Ser Ile Thr Lys Ser
        35                  40                  45

Ala Cys Gly Arg Asn Gly Lys Gln Phe Cys Ser Thr Leu Thr Leu Asn
    50                  55                  60

Thr Ala Gln Ala Asn His Thr Gly Phe Tyr Ser Cys Lys Tyr Leu Ala
65                  70                  75                  80

Val Pro Thr Ser Lys Lys Lys Glu Thr Glu Ser Ala Ile Tyr Ile Phe
                85                  90                  95

Ile
```

<210> SEQ ID NO 16
<211> LENGTH: 93
<212> TYPE: PRT
<213> ORGANISM: Homo sapiens

<400> SEQUENCE: 16

```
Pro Phe Val Glu Met Tyr Ser Glu Ile Pro Glu Ile Ile His Met Thr
1               5                   10                  15

Glu Gly Arg Glu Leu Val Ile Pro Cys Arg Val Thr Ser Pro Asn Ile
            20                  25                  30

Thr Val Thr Leu Lys Lys Phe Pro Leu Asp Thr Leu Ile Pro Asp Gly
        35                  40                  45

Lys Arg Ile Ile Trp Asp Ser Arg Lys Gly Phe Ile Ile Ser Asn Ala
    50                  55                  60

Thr Tyr Lys Glu Ile Gly Leu Leu Thr Cys Glu Ala Thr Val Asn Gly
65                  70                  75                  80

His Leu Tyr Lys Thr Asn Tyr Leu Thr His Arg Gln Thr
                85                  90
```

<210> SEQ ID NO 17
<211> LENGTH: 100
<212> TYPE: PRT
<213> ORGANISM: Homo sapiens

<400> SEQUENCE: 17

```
Val Gln Ile Ser Thr Pro Arg Pro Val Lys Leu Leu Arg Gly His Thr
1               5                   10                  15

Leu Val Leu Asn Cys Thr Ala Thr Thr Pro Leu Asn Thr Arg Val Gln
            20                  25                  30

Met Thr Trp Ser Tyr Pro Asp Glu Lys Asn Lys Arg Ala Ser Val Arg
        35                  40                  45

Arg Arg Ile Asp Gln Ser Asn Ser His Ala Asn Ile Phe Tyr Ser Val
    50                  55                  60

Leu Thr Ile Asp Lys Met Gln Asn Lys Asp Lys Gly Leu Tyr Thr Cys
65                  70                  75                  80

Arg Val Arg Ser Gly Pro Ser Phe Lys Ser Val Asn Thr Ser Val His
                85                  90                  95
```

-continued

```
Ile Tyr Asp Lys
            100


<210> SEQ ID NO 18
<211> LENGTH: 96
<212> TYPE: PRT
<213> ORGANISM: Homo sapiens

<400> SEQUENCE: 18

Phe Ile Thr Val Lys His Arg Lys Gln Gln Val Leu Glu Thr Val Ala
1               5                   10                  15

Gly Lys Arg Ser Tyr Arg Leu Ser Met Lys Val Lys Ala Phe Pro Ser
            20                  25                  30

Pro Glu Val Val Trp Leu Lys Asp Gly Leu Pro Ala Thr Glu Lys Ser
        35                  40                  45

Ala Arg Tyr Leu Thr Arg Gly Tyr Ser Leu Ile Ile Lys Asp Val Thr
    50                  55                  60

Glu Glu Asp Ala Gly Asn Tyr Thr Ile Leu Leu Ser Ile Lys Gln Ser
65                  70                  75                  80

Asn Val Phe Lys Asn Leu Thr Ala Thr Leu Ile Val Asn Val Lys Pro
                85                  90                  95
```